United States Patent
Pena Serrada et al.

(10) Patent No.: US 11,478,639 B2
(45) Date of Patent: Oct. 25, 2022

(54) SYSTEMS AND METHODS FOR DELIVERING FOCALIZED NEUROSTIMULATION

(71) Applicants: Andres E. Pena Serrada, Miami, FL (US); Ranu Jung, Miami, FL (US); James Abbas, Scottsdale, AZ (US); Kenneth Horch, Miami, FL (US)

(72) Inventors: Andres E. Pena Serrada, Miami, FL (US); Ranu Jung, Miami, FL (US); James Abbas, Scottsdale, AZ (US); Kenneth Horch, Miami, FL (US)

(73) Assignees: THE FLORIDA INTERNATIONAL UNIVERSITY BOARD OF TRUSTEES, Miami, FL (US); ARIZONA BOARD OF REGENTS ON BEHALF OF ARIZONA STATE UNIVERSITY, Scottsdale, AZ (US)

( * ) Notice: Subject to any disclaimer, the term of this patent is extended or adjusted under 35 U.S.C. 154(b) by 0 days.

(21) Appl. No.: 17/592,646

(22) Filed: Feb. 4, 2022

(65) Prior Publication Data
US 2022/0257945 A1    Aug. 18, 2022

Related U.S. Application Data

(60) Provisional application No. 63/149,015, filed on Feb. 12, 2021.

(51) Int. Cl.
| | |
|---|---|
| *A61N 1/36* | (2006.01) |
| *G06F 3/01* | (2006.01) |
| *A61N 1/04* | (2006.01) |
| *A61F 2/72* | (2006.01) |

(52) U.S. Cl.
CPC ............ *A61N 1/36034* (2017.08); *A61F 2/72* (2013.01); *A61N 1/0456* (2013.01); *G06F 3/015* (2013.01)

(58) Field of Classification Search
CPC ...... A61N 1/36034; A61N 1/0456; A61F 2/72
USPC ........................................................ 600/595
See application file for complete search history.

(56) References Cited

U.S. PATENT DOCUMENTS

2006/0149337 A1*  7/2006  John ................... A61N 1/37235
                                                    607/45

OTHER PUBLICATIONS

Emma K. Brunton et al., Temporal Modulation of the Response of Sensory Fibers to Paired-Pulse Stimulation, IEEE Transactions on Neural Systems and Rehabilitation Engineering, vol. 27, No. 9, Sep. 2019, 1676-1683, 9 pages.

(Continued)

*Primary Examiner* — Nadia A Mahmood
(74) *Attorney, Agent, or Firm* — Saliwanchik, Lloyd & Eisenschenk

(57) ABSTRACT

Systems and methods for delivering targeted neurostimulation therapies to the nervous system of a subject are provided. A set of electrodes can be strategically distributed around a target nerve, and the nerve can be activated though the electrodes using a channel-hopping interleaved pulse scheduling (CHIPS) stimulation strategy. The systems and methods can leverage the spatiotemporal summation of short, sub-threshold current pulses interleaved across two or more independent stimulation channels (hopping from channel to channel) and delivered across electrodes strategically placed in an interfering configuration around the target neural tissue.

18 Claims, 20 Drawing Sheets

(56) References Cited

OTHER PUBLICATIONS

Bo Geng et al., Impacts of selected stimulation patterns on the perception threshold in electrocutaneous stimulation, Journal of NeuroEngineering and Rehabilitation 2011, 8:9, 11 pages.

* cited by examiner

FIG. 2

Q1  Please indicate the modality of the sensations you feel by checking the appropriate boxes below

| Fist closed | Pressure | Hot | Deep Pain |
| Fist open | Needle Prick | Sharp Pain | Other |
| Finger bent | Tingling | Diffuse Pain | (Describe) |
| Fingers spread | Cool | Numb | |
| Light Touch | Warm | Unnatural | |

Q2  Please describe the quality of the sensations you feel by checking the appropriate boxes below

| Comfortable | Sharp | Soft | Strong |
| Uncomfortable | Blunt | Mild | Other (Describe) |

Q3  Please indicate the location of the sensations you feel by checking the appropriate boxes below Local    Spreading    Referred    Other (Describe)

Q4  Please illustrate in the diagrams below the areas where you feel the sensation

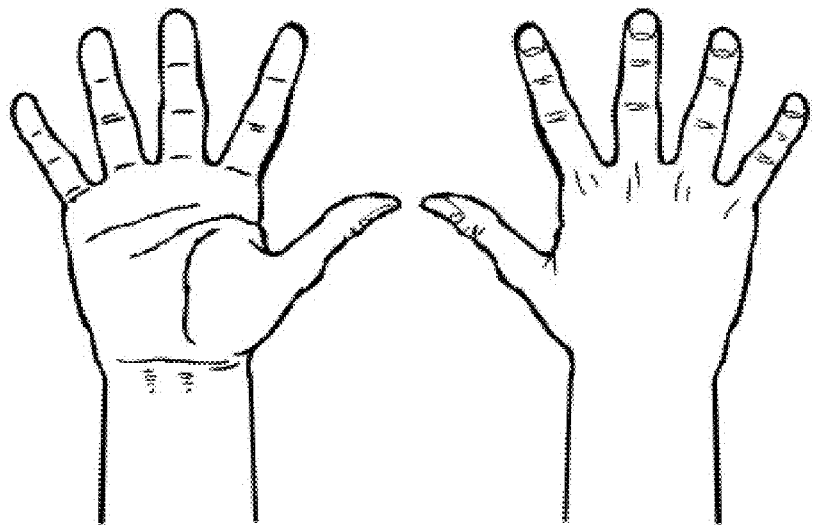

FIG 10

SYSTEMS AND METHODS FOR DELIVERING FOCALIZED NEUROSTIMULATION

CROSS-REFERENCE TO RELATED APPLICATION

This application claims the benefit of U.S. Provisional Application Ser. No. 63/149,015, filed Feb. 12, 2021, which is hereby incorporated by reference herein in its entirety, including any figures, tables, and drawings.

BACKGROUND

Sensory feedback plays an integral role in everyday function, including planning and control of even simple movements, such as grasping an object [1]. Loss of sensory function caused by a life-changing event such as amputation after limb trauma or peripheral neuropathies after nerve injury can have substantial effects on work, leisure, social life, and daily living activities as well as on psychological well-being. People rely on sensory feedback for everyday function, including planning and control of even simple movements, such as reaching for an object. In 2005, in the United States of America, approximately 541,000 Americans had some level of upper limb loss and over 30% of them experienced some level of depression and/or anxiety. This number is expected to double by the year 2050. Individuals with upper limb amputation may use a myoelectric prosthesis. However, despite recent technological advances, the prostheses are still limited in their ability to provide direct sensory feedback to users, thereby requiring an increased reliance on visual cues and attentional demand from the user and resulting in substantial functional deficits. Because of this, sensory feedback is one of the most desired design priorities independent of the type of prosthesis and level of limb loss.

The provision of sensory feedback may enable the user to better control the prosthesis and perform precise tasks with lower attentional demands thereby improving quality of life. It also has the potential to promote prosthesis embodiment.

For decades, the development of artificial sensory feedback systems has mostly centered on the activation of cutaneous mechanoreceptors through mechanical or electro-tactile stimulation to convey somatotopically-mismatched information (sensory substitution), and the activation of sensory fibers in peripheral nerves to evoke somatotopically-matched, distally referred sensations in the phantom hand. Non-invasive mechanical and electro-tactile sensory substitution approaches encode the missing sensory information (e.g. grasp force) through an alternate sensory channel by delivering tactile information at specific locations on the user's skin. Although these approaches offer an opportunity for conveying some information about prosthesis usage, they are often unable to evoke intuitive sensations due to percept modality and location mismatch. This limits the efficacy of the sensory feedback and increases the user's cognitive load and response time.

Alternatively, electrical stimulation of peripheral nerve sensory fibers has shown potential for delivering somatotopically-matched feedback. Implantable neuromodulation systems have been used to activate sensory fibers in the median and ulnar nerves to evoke graded distally referred tactile and proprioceptive sensations in the phantom hand of individuals with amputation. These direct stimulation methods are characterized by high selectivity and sensation quality features that facilitate the delivery of more intuitive sensory feedback from prosthetic limbs. However, the invasive nature of device implantation procedures is not acceptable to all.

BRIEF SUMMARY

Embodiments of the subject invention provide novel and advantageous systems and methods for delivering targeted neurostimulation therapies to the nervous system of a subject (e.g., a human subject). A set of electrodes can be (strategically) distributed around a target nerve, and the nerve can be activated though the electrodes (of the set of electrodes) using a channel-hopping interleaved pulse scheduling (CHIPS) stimulation strategy. The systems and methods can leverage the spatiotemporal summation of short, sub-threshold current pulses interleaved across two or more independent stimulation channels (hopping from channel to channel) and delivered across electrodes strategically placed in an interfering configuration around the target neural tissue. During CHIPS, stimulation pulses can be scheduled to be delivered sequentially from different sources, with no overlap or additional temporal separation (i.e., one right after the other). By leveraging the combined influence of the interleaved current pulses, each independent channel is set to stimulate at relatively short pulse widths (e.g., less than 1 millisecond (ms), such as 0.25 ms or 0.5 ms), thus keeping the total charge per pulse delivered by any given electrode low, while maintaining net charge delivery to the target nerve at functional levels. In other words, as short pulses are delivered sequentially at different locations around or within the neural tissue, the target nerve fibers experience one longer pulse. As a result, the stimulation can be sub-threshold near each electrode, but supra-threshold at the target due to the spatiotemporal summation of the interleaved pulses. This increases selectivity while avoiding the localized charge densities associated with undesired outcomes such as discomfort, tissue damage, and electrode degradation.

Related work by the inventors is presented in U.S. application Ser. No. 17/214,533, filed Mar. 26, 2021, which is hereby incorporated by reference herein in its entirety, including any figures, tables, and drawings.

It is an object of the subject invention to develop, characterize, and test a non-invasive neurostimulation approach capable of selectively eliciting comfortable distally referred tactile percepts, with a wide range of graded intensities, that could be used to complete functional tasks. It is a further object of the subject invention to achieve an enhanced surface electrical neurostimulation (eSENS) platform.

Embodiments may provide a non-invasive electrical neurostimulation strategy capable of evoking comfortable distally referred tactile percepts while avoiding the local sensations and skin discomfort associated with localized charge densities in traditional methods. Embodiments may leverage the combined influence of the shorter, sub-threshold pulses interleaved across two independent channels to activate sensory fibers with percept thresholds comparable to those from traditional single-channel stimulation; enable the use of small electrodes to increase selectivity while avoiding the larger charge densities associated with them; and elicit enhanced tactile percepts while avoiding the distracting sensations and discomfort.

Embodiments may convey a wide range of discriminable levels of tactile intensities for haptic feedback by implementing a charge-rate encoding strategy within the neurostimulation platform. Embodiments provide the first evaluation of activation charge-rate to enhance the percept intensity mapping with surface electrical neurostimulation. The charge-rate relationship may be leveraged to enable fast and accurate stimulation parameter fitting with minimal intervention from the experimenter. Implementation of charge-rate encoding within the eSENS platform showed that it is possible to artificially influence the intensity code transcutaneously with psychophysical responses comparable to intrafascicular stimulation Embodiments have been used to successfully integrate charge-rate encoding via surface stimulation. Psychophysical studies have demonstrated discrimination performance (gradation) and intensity estimation (range). Parameter ranges for charge-rate modulation (QRM) include (1) modulation of charge above activation threshold (e.g., from the point the stimuli produces a sensation, to the point right before it becomes uncomfortable), and (2) modulation of frequency (e.g., from point where individual pulses feel fused (fusion), to the point where frequency no longer increases intensity (saturation).)

Embodiments have been used to assess the ability of the neurostimulation platform to deliver intuitive haptic feedback that can be utilized to complete functional tasks. Embodiments leverage the combined influence of the shorter, sub-threshold pulses interleaved across two independent channels to activate sensory fibers with percept thresholds comparable to those from traditional single-channel stimulation. Embodiments may further enable the use of small electrodes to increase selectivity while avoiding the larger charge densities associated with them; and elicit enhanced tactile percepts while avoiding the distracting sensations and discomfort.

In one example subjects received task-related feedback from the stimulation platform, enhanced by the novel CHIPS strategy and charge-rate intensity encoding. The feedback was used to complete functional tasks without the need for visual feedback. The feedback provided relevant information to inform their control actions. The subjects' grasping action was guided by the sensory feedback while exploring the object's characteristics. Subjects used sensory feedback to correct their error when moving past the target during graded control tasks.

In one embodiment, the channel-hopping interleaved pulse scheduling strategy was able to elicit enhanced tactile percepts while avoiding the distracting sensations and discomfort associated with localized charge densities. Implementation of a charge-rate encoding strategy within the eSENS platform resulted in fine intensity discrimination and a wider dynamic range of percept intensities than frequency modulation alone. The tactile percepts delivered by the eSENS platform, with the implementation of the CHIPS strategy and charge-rate encoding, could be readily utilized by able-bodied subjects to complete functional tasks without the need for visual feedback.

Embodiments may provide (alone or in combination) eSENS Strategies and Features for Pulse Scheduling, Sensory Encoding, and Stimulation Parameter Fitting. In certain embodiments employing a Pulse Scheduling Strategy, Channel-hopping Interleaved Pulse Scheduling (CHIPS) produced comfortable referred-only percepts while preventing high current densities under the electrodes so that cutaneous receptors are not activated.

In certain embodiments employing a Sensory Encoding Strategy, Charge-rate Modulation (QRM) produced Wide range of graded percept intensities expanding the dynamic range of intensities by using a bio-inspired encoding approach.

In certain embodiments employing a Stimulation Parameter Fitting Strategy, User-in-the-loop (UiTL) Calibration Routines produced fast and effective stimulation parameter fitting process.

In an embodiment, delivering stimulation pulses in an interleaved fashion across multiple strategically distributed electrodes reduces the charge density under each individual electrode, lowering the chances of skin discomfort while maintaining net charge delivery at functional levels; and leverages the "RC recovery time interval" as the membrane momentarily contains the charge of the leading pulse, making it easier for the fiber to depolarize after the trailing pulse.

Embodiments provide a system for delivering targeted focal neurostimulation with reduced charge density and increased selectivity to a target nerve. The system may comprise a first channel comprising a first alternating current (AC) source connected to a first stimulating electrode and a first receiving electrode, the first stimulating electrode radially spaced from the target nerve, and the first receiving electrode being in opposition to the first stimulating electrode such that a first signal path defined therebetween stimulates the target nerve. The system may comprise a second channel comprising a second AC source connected to a second stimulating electrode and a second receiving electrode, the second stimulating electrode radially spaced from the target nerve, and the second receiving electrode being in opposition to the second stimulating electrode such that a second signal path defined therebetween crosses the first signal path and stimulates the target nerve. The system may comprise a processor in operable communication with the first channel and the second channel and a machine-readable medium in operable communication with the processor and having instructions stored thereon that, when executed by the processor, perform a series of steps. The steps may comprise delivering through the first channel a first stimulation pulse (SP1) having a first stimulation pulse width (SP1W) and delivering through the second channel a second stimulation pulse (SP2) after delivery of the SP1, the SP2 having a second stimulation pulse width (SP2W). The SP1 and the SP2 may each contribute to an effective net stimulation pulse (ESP) having an effective net stimulation pulse width (ESPW) sufficient to effectively stimulate the target nerve, the ESPW being greater than at least one of the SP1W and the SP2W, thereby delivering the targeted focal neurostimulation with reduced charge density and increased selectivity to the target nerve.

In an embodiment, the machine-readable medium in operable communication with the processor may have further instructions stored thereon that, when executed by the processor, perform the following additional steps: delivering through one of the first channel or the second channel a first charge-balancing pulse (BP1) after delivery of the SP2, the BP1 having a first balancing pulse width (BP1W); and delivering through the other of the first channel or the second channel a second charge-balancing pulse (BP2) after delivery of the BP1, the BP2 having a second balancing pulse width (BP2W). The BP1 and the BP2 each contributing to an effective net charge-balancing pulse (EBP) having an effective net charge-balancing pulse width (EBPW) sufficient to effectively reduce a residual local charge created by the ESP in or around the target nerve, and the EBPW being greater than at least one of the BP1W and the BP2W.

In an embodiment, each of the SP1, the SP2, the BP1, and the BP2, respectively, may have a start time and an end time, and the start time of the BP1 may follow by an inter-phase gap (IPG) having a value between 0 microseconds and 500 microseconds after the end time of the SP2.

It should be understood that an IPG of 0 microseconds is equivalent to having no IPG at all. Reference to an IPG of 0 milliseconds may be useful to discuss and consider cases of small IPG or reducing IPG together with the case of no IPG or one pulse following immediately after another. The IPG may also have a value that is near, about, or approaching 0 microseconds as the IPG grows very small.

Embodiments may also provide overlapping pulses, for example where a second or trailing pulse (e.g., BP1) may have a start time which may lead by an inter-phase overlap (IPO) having a value between 0 microseconds and 500 microseconds before the end time of a first or leading pulse (e.g., SP2).

It should be understood that an IPO of 0 microseconds is equivalent to having no IPO at all. Reference to an IPO of 0 milliseconds may be useful to discuss and consider cases of small IPO or reducing IPO together with the case of no IPO or one pulse following immediately after another. The IPO may also have a value that is near, about, or approaching 0 microseconds as the IPO grows very small.

In an embodiment, the start time of the SP2 may follow by a first interleaved stimulation pulse delay (DS1) having a value between 0 microseconds and 500 microseconds after the end time of either (a) the SP1, or (b) an optional additional interleaved stimulation pulse (SP3), the SP3, if present, being delivered after delivery of the SP1, and before the delivery of the SP2.

In an embodiment, the start time of the BP2 may follow by a first interleaved charge-balancing pulse delay (DB1) having a value between 0 microseconds and 500 microseconds after the end time of either (a) the BP1, or (b) an optional additional interleaved charge-balancing pulse (BP3), the BP3, if present, being delivered after delivery of the BP1, and before the delivery of the BP2.

It should be understood that DS1 or DB1 or any other "delay" value of 0 microseconds is equivalent to having no delay at all. Reference to a delay of 0 milliseconds may be useful to discuss and consider cases of small delay or reducing delay together with the case of no delay or one pulse following immediately after another. The DS1 or DB1 may also have a value that is near, about, or approaching 0 microseconds as the DS1 or DB1 grows very small.

In an alternative embodiment, the start time of the SP2 may lead by a first interleaved stimulation pulse overlap (OS1) having a value between 0 microseconds and 500 microseconds before the end time of either (a) the SP1, or (b) an optional additional interleaved stimulation pulse (SP3), the SP3, if present, being delivered after delivery of the SP1, and before the delivery of the SP2.

In another alternative embodiment, the start time of the BP2 may lead by a first interleaved charge-balancing pulse overlap (GB1) having a value between 0 microseconds and 500 microseconds before the end time of either (a) the BP1, or (b) an optional additional interleaved charge-balancing pulse (BP3), the BP3, if present, being delivered after delivery of the BP1, and before the delivery of the BP2.

It should be understood that OS1 or OB1 or any other "overlap" value of 0 microseconds is equivalent to having no overlap at all. Reference to an overlap of 0 milliseconds may be useful to discuss and consider cases of small overlap or reducing overlap together with the case of no overlap or one pulse following immediately after another. The OS1 or OB1 may also have a value that is near, about, or approaching 0 microseconds as the OS1 or OB1 grows very small.

While some examples and discussions within this disclosure refer to square waves which may transition rapidly, nearly instantaneously, or instantaneously from one amplitude to another (e.g., a pulse changing immediately from zero to PA or −PA at a prescribed start time and from PA or −PA back to zero immediately at a prescribed end time), it should be understood that start and end times are still properly defined for all pulse forms (including, without limitation, square waves, imperfect square waves, and perfect or imperfect forms of pulse, sine triangle, sawtooth, or other wave forms) as the point at which a first or last measurable change, respectively, is observed in the pulse. Alternatively, an effective start or stop of a pulse may be defined as the point at which the change in signal is first or last observable at a particular point in a given system (e.g., when a voltage or current is first measurable at a target nerve in a subject.) In some embodiments, pulses, voltages, currents, and other stimulation parameters may also be measured relative to a specified non-zero reference.

In an embodiment, the machine-readable medium in operable communication with the processor may have further instructions stored thereon that, when executed by the processor, perform the following additional steps: delivering through one of the first channel or the second channel a fourth stimulation pulse (SP4) after delivery of the BP2, the SP4 having a fourth stimulation pulse width (SP4W); and delivering through the other of the first channel or the second channel a fifth stimulation pulse (SP5) after delivery of the SP4, the SP5 having a fifth stimulation pulse width (SP5W). The SP4 and the SP5 each contributing to a second effective net stimulation pulse (ESP2) having a second effective net stimulation pulse width (ESP2W) sufficient to effectively stimulate the target nerve, the ESP2W being greater than at least one of the SP4W and the SP5W.

In an embodiment, each of the SP4, and the SP5, respectively, having a start time and an end time; the start time of the SP5 may follow by a second interleaved stimulation pulse delay (DS2) having a value between 0 microseconds and 500 microseconds after the end time of either (a) the SP4, or (b) an optional additional interleaved stimulation pulse (SP6), the SP6, if present, being delivered after delivery of the SP4, and before the delivery of the SP5.

The first stimulating electrode and the first receiving electrode may be positioned to stimulate the target nerve transversely.

The second stimulating electrode and the second receiving electrode may be positioned to stimulate the target nerve transversely and being generally aligned longitudinally with each other and with the first stimulating electrode and the first receiving electrode. It is contemplated that in certain embodiments, individual electrodes or electrode pairs may be aligned or distributed in a radial direction, a longitudinal direction, or directions measured in one or more alternative frames of reference. Electrodes are said to be generally aligned in one or more directions when there exists any measurable overlap between the electrodes in the measurement direction. Electrodes are said to be adjacent in one or more directions when separated by a distance equal to or less than the width of one of the electrodes existing between the electrodes in the measurement direction (e.g., a radial separation of 5 mm between two electrodes having diameters of 4 mm and 6 mm, respectively.) Electrodes are said to be distributed in one or more directions when separated by a distance greater than the width of one of the electrodes existing between the electrodes in the measurement direction (e.g., a longitudinal separation of 7 mm between two electrodes having diameters of 4 mm and 6 mm, respectively.)

In an embodiment, the SP1 and the BP1 may form an anode-first biphasic pulse on the first channel, the SP2 and the BP2 may form an anode-first biphasic pulse on the second channel, and the SP1, the SP2, the BP1, and the BP2 each may contribute to delivering an effective anode-first biphasic pulse to the target nerve.

Embodiments provide a method for delivering targeted focal neurostimulation with reduced charge density and increased selectivity to a target nerve. The method may comprise providing a first channel comprising a first alternating current (AC) source connected to a first stimulating electrode and a first receiving electrode, the first stimulating electrode radially spaced from the target nerve, and the first receiving electrode being in opposition to the first stimulating electrode such that a first signal path defined therebetween stimulates the target nerve; providing a second channel comprising a second AC source connected to a second stimulating electrode and a second receiving electrode, the second stimulating electrode radially spaced from the target nerve, and the second receiving electrode being in opposition to the second stimulating electrode such that a second signal path defined therebetween crosses the first signal path and stimulates the target nerve; delivering (e.g., via a processor in operable communication with the first channel and the second channel) through the first channel a first stimulation pulse (SP1) having a leading stimulation pulse width (SP1W); and delivering (e.g., via the processor) through the second channel a second stimulation pulse (SP2) after delivery of the SP1, the SP2 having a trailing stimulation pulse width (SP2W). The SP1 and the SP2 each may contribute to an effective net stimulation pulse (ESP) having an effective net stimulation pulse width (ESPW) sufficient to effectively stimulate the target nerve, the ESPW being greater than at least one of the SP1W and the SP2W, thereby delivering the targeted focal neurostimulation with reduced charge density and increased selectivity to the target nerve.

While certain embodiments may be discussed in terms of a simple two channel configuration, it is contemplated within the scope of the subject invention to utilize any number of channels within limitations such as subject anatomy and physiology, electrical control, connectivity, and electrode technology (e.g., 2, 3, 4, 5, 6, or more channels are currently feasible with external transdermal electrodes placed on or around the wrist of a subject, while higher numbers of channels may be feasible using intrafascicular stimulation.) It is also contemplated within the scope of the subject invention that channels may be either defined and allocated to a single physical electrode pair, or mapped and distributed dynamically over time, during a pulse, between pulses, on a predetermined schedule, or in response to subject feedback or sensor values. It is further contemplated that a channel may be directed across more than one electrode, that multiple stimulating electrodes may be paired with one or more receiving electrode, that one or more stimulating electrodes may be paired with multiple receiving electrodes, and that pairings or mappings of channels and electrodes may be changed over time. Certain non-limiting examples of electrode pairings and mappings are illustrated in FIGS. 16A-16D.

In an embodiment, the machine-readable medium in operable communication with the processor may have further instructions stored thereon that, when executed by the processor, perform the following additional steps: delivering through one of the first channel or the second channel a first charge-balancing pulse (BP1) after delivery of the SP2, the BP1 having a first balancing pulse width (BP1W); and delivering through the other of the first channel or the second channel a second charge-balancing pulse (BP2) after delivery of the BP1, the BP2 having a second balancing pulse width (BP2W); the BP1 and the BP2 each contributing to an effective net charge-balancing pulse (EBP) having an effective net charge-balancing pulse width (EBPW) sufficient to effectively reduce a residual local charge created by the ESP in or around the target nerve, the EBPW being greater than at least one of the BP1W and the BP2W.

In an embodiment, each of the SP1, the SP2, the BP1, and the BP2, respectively, having a start time and an end time, the start time of the BP1 may follow by an inter-phase gap (IPG) having a value between 0 microseconds and 500 microseconds behind the end time of the SP2. The start time of the SP2 may follow by a first interleaved stimulation pulse delay (DS1) having a value between 0 microseconds and 500 microseconds after the end time of either (a) the SP1, or (b) an optional additional interleaved stimulation pulse (SP3), the SP3, if present, being delivered after delivery of the SP1, and before the delivery of the SP2. The start time of the BP2 may follow by a first interleaved charge-balancing pulse delay (DB1) having a value between 0 microseconds and 500 microseconds after the end time of either (a) the BP1, or (b) an optional additional interleaved charge-balancing pulse (BP3), the BP3, if present, being delivered after delivery of the BP1, and before the delivery of the BP2.

In an embodiment, the machine-readable medium in operable communication with the processor may have further instructions stored thereon that, when executed by the processor, perform the following additional steps: delivering through one of the first channel or the second channel a fourth stimulation pulse (SP4) after delivery of the BP2, the SP4 having a fourth stimulation pulse width (SP4W); and delivering through the other of the first channel or the second channel a fifth stimulation pulse (SP5) after delivery of the SP4, the SP5 having a fifth stimulation pulse width (SP5W); the SP4 and the SP5 each contributing to a second effective net stimulation pulse (ESP2) having a second effective net stimulation pulse width (ESP2W) sufficient to effectively stimulate the target nerve, the ESP2W being greater than at least one of the SP4W and the SP5W.

In an embodiment, each of the SP4, and the SP5, respectively, having a start time and an end time; the start time of the SP5 may follow by a second interleaved stimulation pulse delay (DS2) having a value between 0 microseconds and 500 microseconds after the end time of either (a) the SP4, or (b) an optional additional interleaved stimulation pulse (SP6), the SP6, if present, being delivered after delivery of the SP4, and before the delivery of the SP5.

Embodiments provide a system for delivering targeted focal neurostimulation with reduced charge density and increased selectivity to a target nerve. The system may comprise a first channel comprising a first alternating current (AC) source connected to a first stimulating electrode and a first receiving electrode, the first stimulating electrode radially spaced from the target nerve and the first receiving electrode in opposition to the first stimulating electrode such that a first signal path defined therebetween stimulates the target nerve; and a second channel comprising a second AC source connected to a second stimulating electrode and a second receiving electrode, the second stimulating electrode radially spaced from the target nerve and the second receiving electrode in opposition to the second stimulating electrode such that a second signal path defined therebetween crosses the first signal path and stimulates the target nerve; and a processor in operable communication with the first channel and the second channel; and a machine-readable medium in operable communication with the processor and having instructions stored thereon that, when executed by the processor, perform a series of steps. The steps may include delivering through the first channel a first stimulation pulse (SP1) having a first stimulation pulse width (SP1W); delivering through the second channel a second stimulation pulse (SP2) after delivery of the SP1, the SP2 having a second stimulation pulse width (SP2W); the SP1 and the SP2 each contributing to an effective net stimulation pulse (ESP) having an effective net stimulation pulse width (ESPW) sufficient to effectively stimulate the target nerve, the ESPW being greater than at least one of the SP1W and the SP2W; delivering through one of the first channel or the second channel a first charge-balancing pulse (BP1) after delivery of the SP2, the BP1 having a first balancing pulse width (BP1W); delivering through the other of the first channel or the second channel a second charge-balancing pulse (BP2) after delivery of the BP1, the BP2 having a second balancing pulse width (BP2W); the BP1 and the BP2 each contributing to an effective net charge-balancing pulse (EBP) having an effective net charge-balancing pulse width (EBPW) sufficient to effectively reduce a residual local charge created by the ESP in or around the target nerve, the EBPW being greater than at least one of the BP1W the BP2W; delivering through one of the first channel or the second channel a fourth stimulation pulse (SP4) after delivery of the BP2, the SP4 having a fourth stimulation pulse width (SP4W); delivering through the other of the first channel or the second channel a fifth stimulation pulse (SP5) after delivery of the SP4, the SP5 having a fifth stimulation pulse width (SP5W); and the SP4 and the SP5 each contributing to a second effective net stimulation pulse (ESP2) having a second effective net stimulation pulse width (ESP2W) sufficient to effectively stimulate the target nerve, the ESP2W being greater than at least one of the SP4W and the SP5W, thereby delivering the targeted focal neurostimulation with reduced charge density and increased selectivity to the target nerve.

In an embodiment, each of the SP1, the SP2, the SP4, the SP5 the BP1, and the BP2, respectively, having a start time and an end time; the start time of the BP1 may follow by an inter-phase gap (IPG) having a value between 0 microseconds and 500 microseconds behind the end time of the SP2; the start time of the SP2 may follow by a first interleaved stimulation pulse delay (DS1) having a value between 0 microseconds and 500 microseconds after the end time of either (a) the SP1, or (b) an optional additional interleaved stimulation pulse (SP3), the SP3, if present, being delivered after delivery of the SP1, and before the delivery of the SP2; the start time of the BP2 may follow by a first interleaved charge-balancing pulse delay (DB1) having a value between 0 microseconds and 500 microseconds after the end time of either (a) the BP1, or (b) an optional additional interleaved charge-balancing pulse (BP3), the BP3, if present, being delivered after delivery of the BP1, and before the delivery of the BP2; and the start time of the SP5 may follow by a second interleaved stimulation pulse delay (DS2) having a value between 0 microseconds and 500 microseconds after the end time of either (a) the SP4, or (b) an optional additional interleaved stimulation pulse (SP6), the SP6, if present, being delivered after delivery of the SP4, and before the delivery of the SP5.

In an embodiment, the first stimulating electrode and the first receiving electrode being positioned to stimulate the target nerve transversely; the second stimulating electrode and the second receiving electrode being positioned to stimulate the target nerve transversely and being generally aligned longitudinally with each other and with the first stimulating electrode and the first receiving electrode; the SP1 and the BP1 may form an anode-first biphasic pulse on the first channel; the SP2 and the BP2 may form an anode-first biphasic pulse on the second channel; and the SP1, the SP2, the BP1, and the BP2 each may contribute to delivering an effective anode-first biphasic pulse to the target nerve.

BRIEF DESCRIPTION OF DRAWINGS

FIG. 2 shows an experiment sequence diagram for human study protocols for testing embodiments of the subject invention.

FIG. 10 shows the MQL Questionnaire to assess the Modality (Q1), Quality (Q2) and Location (Q3) of the elicited percepts according to embodiments of the subject invention.

DETAILED DESCRIPTION

Figures 1A, 1B:
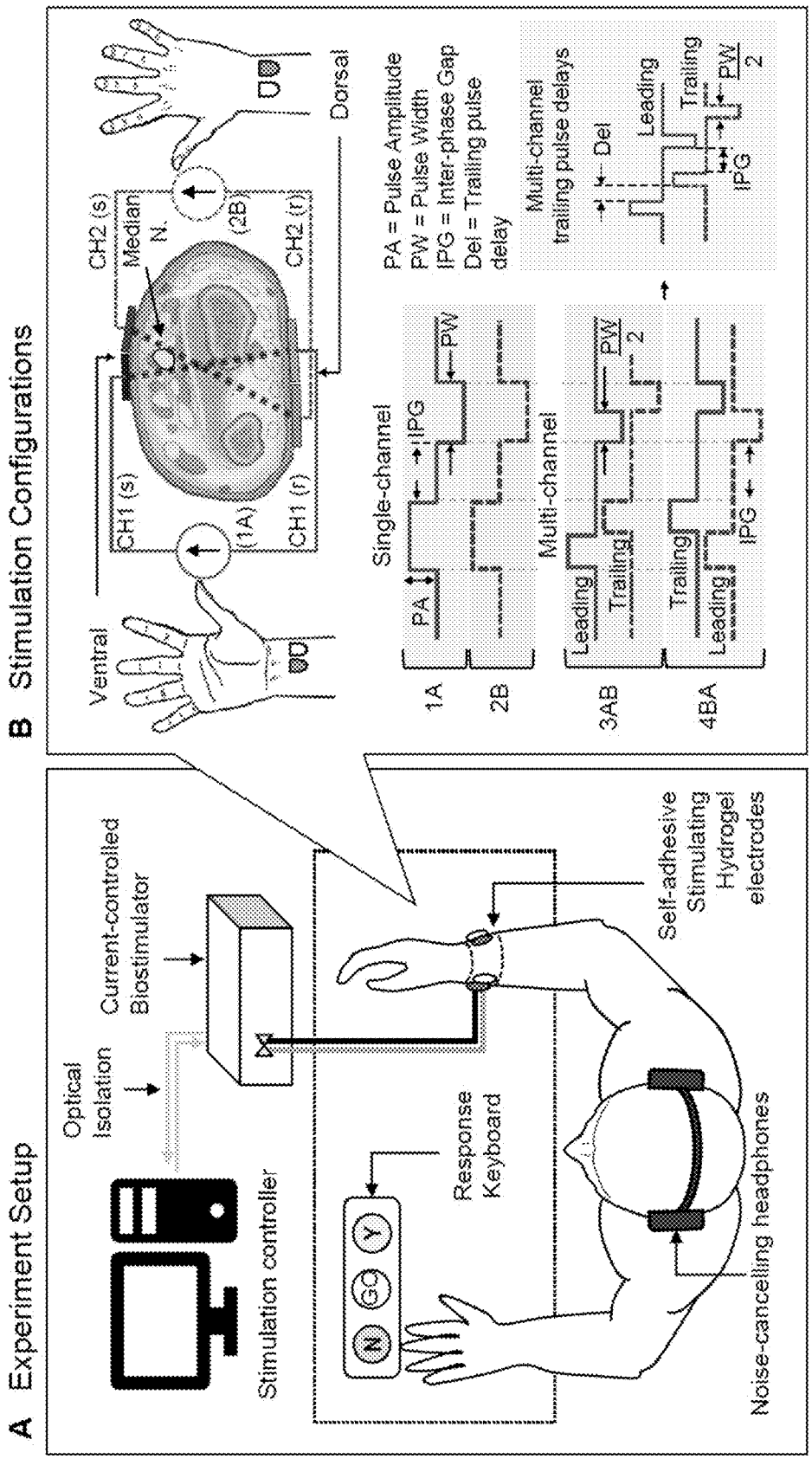
FIG. 1A shows an experimental setup for testing embodiments of the subject invention on a user (e.g., a human user).
FIG. 1B shows stimulation configurations for testing embodiments of the subject invention using the experimental setup of FIG. 1A.

Embodiments of the subject invention provide novel and advantageous systems and methods for delivering targeted neurostimulation therapies to the nervous system of a subject (e.g., a human subject). A set of electrodes can be (strategically) distributed around a target nerve, and the nerve can be activated though the electrodes (of the set of electrodes) using a channel-hopping interleaved pulse scheduling (CHIPS) stimulation strategy. The systems and methods can leverage the spatiotemporal summation of short, sub-threshold current pulses interleaved across two or more independent stimulation channels (hopping from channel to channel) and delivered across electrodes strategically placed in an interfering configuration around the target neural tissue. During CHIPS, stimulation pulses can be scheduled to be delivered sequentially from different sources, with no overlap or additional temporal separation (i.e., one right after the other). By leveraging the combined influence of the interleaved current pulses, each independent channel is set to stimulate at relatively short pulse widths (e.g., less than 1 millisecond (ms), such as 0.25 ms or 0.5 ms; alternatively 0.1, 0.2, 0.3, 0.4, 0.6, 0.7, 0.8, 0.9, or 1 ms, including increments, combinations, and ranges of any of the foregoing), thus keeping the total charge per pulse delivered by any given electrode low, while maintaining net charge delivery to the target nerve at functional levels. In other words, as short pulses are delivered sequentially at different locations around or within the neural tissue, the target nerve fibers experience one longer pulse. As a result, the stimulation can be sub-threshold near each electrode, but supra-threshold at the target due to the spatiotemporal summation of the interleaved pulses. This increases selectivity while avoiding the localized charge densities associated with undesired outcomes such as discomfort, tissue damage, and electrode degradation.

In embodiments, electrical stimulation can be delivered to the nerve using implantable neural interfaces that are intraneural or extraneural. Intraneural electrodes can be intrafascicular (inside the nerve fascicles) and/or interfascicular (between fascicles). Extraneural interfaces are those that deliver stimulation close to the nerve, but outside of the epineurium. Minimally invasive neural interfaces involve percutaneous electrodes such as needle electrodes that are inserted through the skin to reach the nerve. Non-invasive neural stimulation can be done with surface electrodes applied on the skin, delivering transcutaneous electrical pulses to nearby peripheral nerves. All of these neural interface approaches may involve a plurality of electrodes to deliver distributed and targeted stimulation to the nerve. Typically, charge-balanced pulses are used for neurostimulation, where the current amplitude requirements for reaching the target nerve fibers depends on the stimulation delivery approach (smaller currents for implanted electrodes and larger currents for transcutaneous (surface) electrodes).

In embodiments, charge-balanced pulses include two phases of charge delivery of opposite polarity interspersed with a gap. For charge-balance, the shape of the pulse in each of the phases may be rectangular or any other shape as long as the total charge in each phase of the pulse is equivalent. In a traditional single-channel configuration, each current (or voltage) pulse pair is delivered across an electrode pair (stimulation channel). A neurostimulation platform can be configured to deliver these pulses from two or more independent stimulation channels arranged in an interfering configuration, oriented perpendicular to the direction of the nerve (in a "transverse" electrode placement, where the nerve is located in between each electrode pair) so that their current paths cross each other. In a simple multi-channel configuration using only two channels, the first phases of each stimulating channel are delivered consecutively, followed by their respective charge-balancing phases after a given interphase gap (IPG). In more detail, the first phase of the second channel is scheduled to be delivered right after the first phase of the first channel (without delay) so that there is no interruption between pulses while preventing or inhibiting interaction between channels. The charge-balancing phases of each channel (opposite polarity) are then scheduled to be delivered after a given inter-phase delay in the same manner as described above. The leading pulse brings the transmembrane potential close to the activation threshold of the fibers, which would be momentarily maintained due to the electrical properties of the tissue, making it easier for the trailing pulse to cause depolarization. The sequential, interleaved delivery of the phases of each channel results in a specific stimulation region experiencing an overall stimulation pulse width that is as long in duration as the sum of the duration of the individual interleaved pulses. In other words, the region where the stimulation pulses interfere experiences the effects of a single, longer (supra-threshold) stimulation pulse capable of activating nearby fibers while reducing the total charge per pulse delivered by any given electrode. This enables the use of smaller electrodes to increase selectivity while avoiding large charge densities near the electrodes and the associated discomfort, tissue damage, and electrode degradation.

Delivering targeted and focal neurostimulation to the nervous system with CHIPS can involve, for example, a spatially distributed set of electrodes (an electrode array) in which subsets of electrodes are selected to optimize the stimulation effectiveness and comfort. The electrodes in the array can be arranged in any way that enables stimulation from any given electrode pair combination. Electrical stimuli can be generated by at least two independent current sources each connected to one or more electrodes. The resulting potential distribution within the tissue depends on the electrode dimensions, tissue properties, and stimulation parameters such as amplitude and timing of the stimulation pulses, among other factors. This distribution can be shaped by enabling multiple electrodes within each current source (virtually changing the surface area of the electrode) and modulating the charge delivery to adjust the coverage of the activation region.

Electrode array fitting can be accomplished through a sequential exploration of neural responses from multiple combinations of stimulating electrodes within the array. The array fitting process can begin with a fast sweep of different combinations of large groups of electrodes (manipulating parameters such as pulse duration and amplitude) recording settings that produce neural activation. This can be followed by a detailed sweep of individual combinations of electrodes that produce neural activation. The characteristics of the neural responses (e.g., percept responses from the user for a given set of stimulation parameters) generated by these settings can then be ranked from most optimal to least optimal. Similar procedures can be used to determine stimulation amplitude thresholds and the operating ranges for stimulation parameters (e.g. lower and upper bounds for stimulation charge and frequency).

In an embodiment, a computational evaluation of focal nerve stimulation using surface electrode arrays and the CHIPS stimulation strategy can be performed. A simplified hybrid computational model of neural activation in a subject (e.g., a human subject, such as a wrist of a human subject) can be used to implement and characterize the novel CHIPS strategy. The model can comprise the following two components: a two dimensional (2D) finite element model of the subject (e.g., a human wrist) to compute extracellular potential fields; and a sensory axon model to compute neural responses to extracellular electrical stimulation using different electrode configurations and pulse scheduling strategies. This model can provide the means to compare the relative activation of the sensory axons under different stimulation conditions and to visualize the potential outcomes of implementing the novel CHIPS strategy with human subjects. Neural activation results were obtained from the computational effort and used to explore and narrow down the stimulation parameter space. The model predicted activation thresholds for CHIPS stimulation in between those found under single-channel stimulation when the target nerve is somewhere between the current paths of the two stimulating electrodes. The model also predicted that implementation of the CHIPS stimulation strategy would result in activation areas that are smaller than the combined activation areas produced by each independent channel, suggesting that the CHIPS stimulation strategy could result in more focal activation than single-channel stimulation. Simulation results also show lower activation thresholds for both independent channels when the sensory axon is located between both channels.

CHIPS was evaluated with surface stimulation in human subjects. The feasibility of focal nerve stimulation was tested in a study conducted in able-bodied human study participants. The studies were performed for assessing the ability of the systems and methods of embodiments of the subject invention for multi-channel transcutaneous (surface) stimulation using distributed pairs of surface electrodes around the wrist and the CHIPS stimulation strategy, to evoke distally referred sensations, more efficiently and comfortably than traditional single-channel stimulation. The systems and methods of embodiments of the subject invention were found to allow access to mostly afferent fibers that innervate the radial aspect of the palm, and the tips of the thumb, index, and middle fingers, while avoiding most of the motor fibers within the median nerve.

Able-bodied subjects received interleaved current pulses from surface electrodes strategically distributed around their right wrist, resulting in more comfortable, distally-referred tingle-like sensations in the areas of the hand that are innervated by the sensory fibers in the median nerve, with a lower incidence of local sensations than single-channel stimulation. The CHIPS stimulation strategy was able to elicit enhanced tactile percepts while avoiding the distracting sensations and discomfort associated with localized charge densities. The percept thresholds found with CHIPS were comparable to those from single-channel stimulation while delivering lower charges per pulse under any given electrode. The introduction of small delays between interleaved pulses does not strongly compromise the performance of the CHIPS strategy according to embodiments. Instead, they result in a gradual threshold increase, plateauing after a delay of 0.5 ms. This allows for delays of up to 0.2 ms before the combined influence of the interleaved pulses is attenuated by 50%. Alternatively, delays of equal to, less than, or up to 0.01, 0.02, 0.03, 0.04, 0.05, 0.06, 0.07, 0.08, 0.09, 0.1, 0.11, 0.12, 0.13, 0.14, 0.15, 0.16, 0.17, 0.18, 0.19, 0.2, 0.25, 0.3, 0.4, 0.5, 0.6, 0.7, 0.8, 0.9, or 1 ms, including increments, combinations, and ranges of any of the foregoing, may be provided.

Systems and methods of embodiments of the subject invention can be used to restore sensory function to individuals with distal transradial amputation or wrist disarticulation, given that the residual nerves are still accessible. The capabilities of the system CHIPS stimulation strategy can be expanded to deliver simultaneous stimulation to different nerves (such as the median and ulnar nerves) and could potentially allow for two or more distinctive streams of information to be delivered simultaneously, encoding different feedback modalities such as vibration, pressure, touch, slippage, and proprioception, allowing users to better discern information about object size and stiffness, and facilitating the closed-loop control required for fine grasping tasks.

According to embodiments of the subject invention, non-invasive electrical stimulation uses surface electrodes applied on the skin to deliver transcutaneous electrical pulses to activate peripheral nerves. Single-channel surface stimulation can be used to elicit distally referred sensations when targeting the median and ulnar nerves at the forearm or at the elbow level. However, related art methods for single-channel stimulation are hampered by poor selectivity and localized discomfort associated with large charge densities. Embodiments of the subject invention can use surface stimulation to elicit enhanced tactile percepts while avoiding the discomfort associated with localized charge densities by implementing the novel CHIPS strategy. This multi-channel stimulation approach delivers interleaved current pulses from independent stimulation channels; i.e., stimulation hops across multiple strategically distributed surface electrodes. In an embodiment, stimulation pulses are scheduled to be delivered sequentially from different sources, with no overlap or additional temporal separation (i.e., one right after the other). By leveraging the combined influence of the interleaved current pulses, each independent channel could be set to stimulate at shorter pulse widths than single-channel stimulation, thus reducing the total charge per pulse delivered by any given electrode while maintaining net charge delivery to the target nerve at functional levels. In other words, as two short pulses are delivered sequentially at different locations (e.g., at two different locations on the skin), the target fibers in the nerve would experience one longer pulse. As a result, the stimulation is sub-threshold for cutaneous activation near each electrode, but supra-threshold at the level of the nerve due to the spatiotemporal summation of the interleaved pulses.

The examples below show an evaluation of performance of a CHIPS system/method, according to an embodiment of the subject invention, for multi-channel surface stimulation to determine whether it could evoke distally referred sensations more comfortably than single-channel stimulation. Overall, the results indicated that interleaved current pulses from multiple surface electrodes strategically distributed around the wrist result in more comfortable, distally-referred tingle-like sensations in the areas of the hand that are innervated by the sensory fibers in the median nerve, with lower incidence of local sensations near the electrodes than single-channel stimulation. The results indicated that charge delivery using a distributed set of surface electrodes can activate deep nerve fibers without activating those close to the surface of the skin. This ability to elicit distally-referred sensations while avoiding the local sensations that can be distracting or uncomfortable suggests that the CHIPS strategy may be able to enhance the performance of surface electrical stimulation systems for delivering non-invasive sensory feedback.

Multi-channel stimulation with the CHIPS strategy according to embodiments resulted in percept thresholds that were within the range of thresholds found under both single-channel configurations (FIG. 4A), while delivering lower charges per pulse under any given electrode. While not being bound by theory, the inventors believe this is likely the result of the summation of interleaved pulses during the "RC recovery time interval", in which the membrane still contains some of the charge of the leading pulse (bringing it close to the fibers' activation threshold), making it easier for the fiber to depolarize after the trailing pulse. Interestingly, the CHIPS strategy seemed to perform better when leading-trailing pulses were interleaved from high-threshold to low-threshold channels (worst-to-best), or from configuration 2B to 1A (4BA), as seen in FIG. 4B. While not being bound by theory, it is possible that the summation of the leading and trailing pulses was not complete in the examples below. While the leading pulse's effect on the membrane potential could be momentarily sustained, there was likely some decay during the delivery of the trailing pulse. Because the trailing pulse ultimately drives the fiber across its activation threshold, an effective sequence may be one where the trailing pulse is delivered from the best channel.

The introduction of small delays between interleaved pulses did not strongly compromise the performance in this embodiment. Larger delays, however, seemed to attenuate the effect of the leading pulse on the membrane potential at the time of arrival of the trailing pulse, resulting in increased percept thresholds (FIG. 4C), especially for the worst performing multi-channel configuration (3AB). It was initially expected that a sharp transition in percept threshold toward the "no summation" case after a sufficiently long trailing pulse delay. Instead, a gradual threshold increase over the delay values tested was observed. This is consistent with the results of the computational model (see FIG. 8E).

While not being bound by theory, it is hypothesized that the rather gradual threshold increase may reflect consequences of ion channel dynamics on electrical stimulation. The voltage-gated sodium and potassium channels responsible for the generation and propagation of action potentials are known to exhibit hysteresis. For instance, their activation gates can respond much faster to stimulation than their inactivation gate, suggesting that some channels can remain open for some short time after the leading pulse is delivered. In addition, sub-threshold changes in membrane potential have been shown to alter the initial state of the channels in the membrane by partially engaging activation gate segments without reaching inactivation. This "pre-conditions" the channels to open fully at a lower threshold potential, thus increasing their excitability to subsequent stimuli. This excitatory effect of sub-threshold pre-pulses has also been observed during transcutaneous stimulation.

Most surface stimulation studies have used cathode-first biphasic pulses. However, these studies typically utilize a pair of electrodes placed on the same aspect of the limb, but displaced longitudinally (i.e., along the long axis of the nerve); approaches of embodiments of the subject invention can utilize pairs of electrodes placed transversely (across the wrist) and therefore use anode-first pulses. During pilot studies, it was observed that cathode-first pulses outperformed anode-first pulses (had lower thresholds) when targeting the median nerve with a proximal-to-distal electrode pair, placed along the ventral surface of the wrist. This is consistent with fibers hyperpolarizing under the distal anode (blocking efferent signals) and depolarizing under the proximally placed cathode (letting afferent information through). In contrast, anode-first pulses resulted in lower percept thresholds than cathode-first pulses when stimulating the median nerve transversely. While not being bound by theory, it is hypothesized that the difference in sensory activation performance between the two waveforms could be a result of different electric field gradient orientations between these two electrode arrangements.

The comfort and selectivity of surface stimulation are often associated with electrode size and charge density. Large electrodes dissipate the charge over a larger region of the skin, which reduces discomfort, but the charge is also more widely dissipated in the underlying tissues, which reduces the ability to selectivity activate targeted nerves. Reducing the size of the electrode can help focus the stimulation, thereby enhancing the ability to activate nerve fibers, but may require charge densities that cause discomfort in the skin below the electrode. Surface stimulation of the median and ulnar nerves can also result in distracting local sensations due to the activation of the tactile afferents in the skin close to the electrodes. These sensations can be hard to ignore and therefore would affect the overall performance of the stimulation approach. In contrast, the subject invention allows delivery of focal stimulation to the median nerve using small surface electrodes while avoiding the large charge densities associated with local sensations and skin discomfort. In fact, analysis of the MQL questionnaire responses revealed that stimulation under configuration 4BA evoked the most consistent reports of stronger, more comfortable distally-referred sensations (see FIGS. 5A-5C) on the ring and middle fingers as well as the palm of the hand (see FIGS. 6A-6D) without local sensations. These results suggest that implementation of the CHIPS strategy according to an embodiment of the subject invention allowed for focal activation of specific parts of the nerve (partial recruitment) resulting in sensations on the areas of the hand innervated by sensory fibers within the recruited section. More specifically, because the electrodes were placed so their current paths would interfere near the center of the wrist ventral surface, the median nerve would be expected to receive stimulation mostly near its ventral and medial aspect (the side closest to the ulna). Because of this, percepts were evoked more frequently on the ring and middle fingers as well as the palm of the hand, matching the expected somatotopy of the median nerve at this location. Only one subject reported a percept on the back of the hand during CHIPS (configuration 3AB). While not being bound by theory, it is hypothesized that a branch of the ulnar nerve that innervates the back of the little finger, or a cutaneous branch of the radial nerve may have been inadvertently activated.

Percept intensity responses were found to vary across configurations. One potential source of variability in the reported intensity is electrode placement. Both single-channel configurations had different placements, presumably targeting the median nerve differently. This may have probably also been the case for both multi-channel configurations, as they evoked different percept locations and intensities. Perceived intensity is a function of, among other things, population recruitment patterns. The electrode placement used for each configuration could affect the number of afferents responding to the stimulus, consequently affecting the perceived intensity. The results presented in the examples do not include information to account for the variability of reported intensities across subjects. Potential sources of inter-subject variability may include age, gender, skin conductivity, and/or electrode impedance.

Systems and methods of the subject invention provide a viable approach to deliver current pulses transcutaneously to selectively stimulate sensory fibers within the median nerve to elicit enhanced referred sensations, while avoiding the more superficial tactile afferents located under the electrodes. This addresses the primary issues hindering standard non-invasive neuromodulation approaches, making it a feasible alternative for individuals who may not be eligible, or chose not to undergo, surgical procedures for invasive neuromodulation, as the latter carries risks of adverse effects such as infection and persistent implant site pain. Non-invasive neurostimulation with CHIPS could also be used to study the neural mechanisms of natural touch and develop advanced neuromodulation strategies in able-bodied subjects before deployment in implantable systems.

The fitting and targeting performance of the CHIPS strategy of embodiments of the subject invention could be further improved by delivering the stimulation from an array of spatially distributed electrodes, in which subsets of electrodes are selected to optimize the stimulation effectiveness and comfort. The distribution of currents within the tissue depends on the stimulation amplitude, electrode dimensions, and tissue properties, among other factors. This distribution can be shaped by enabling additional electrodes within a single current source (virtually changing the surface area) and modulating the current amplitude to adjust the location of the interference region, effectively steering the percept area. Computational modeling could be used to estimate the distribution of currents while user-controlled calibration routines could be used for sequential exploration of sensory responses from multiple combinations of stimulating electrodes within the array. These responses, combined with results from computational models could be used to optimize the active electrode selection, predict the most likely location of the target nerve within the treatment area, and create user-specific stimulation profiles.

Embodiments could be also applied with extraneural interfaces such as cuff electrodes used for sensory stimulation and functional neuromuscular stimulation. The fascicular structure of the nerve and the insulating properties of its connective tissue are known to impair the ability of cuff electrodes to selectively stimulate small populations of fibers, albeit to a much lesser degree than surface stimulation. It has been attempted to overcome this limitation by reshaping the nerve, increasing the number of electrodes, or by selecting specific electrodes to shape the electric field. The performance of the latter approach could be further enhanced by implementing the CHIPS strategy according to the subject invention not only to avoid activating fibers closer to the electrode contacts, but also to reduce localized charge densities that could cause tissue damage and electrode degradation.

Embodiments could potentially be used beyond prosthetics applications. For instance, the stimulation-evoked percepts could provide intuitive haptic feedback during manipulation and interactions within virtual, augmented, and real environments without the cumbersome restrictions of traditional haptic hardware. This could be useful for haptic feedback in games, teleoperation of unmanned vehicles, surgical procedure training, physical and neurological rehabilitation, and social interactions within virtual worlds. Another innovative aspect of this approach is the potential to deliver targeted neuromodulation therapies for peripheral neuropathies. Surface stimulation has been explored as a non-pharmacological alternative for patients with neuropathic pain symptoms secondary to nerve injury or amputation. Although the neural mechanisms underlying the analgesic effects of conventional surface stimulation are complex and incompletely understood, they are generally consistent with the gate control theory. In this context, embodiments could be used to deliver focal stimulation to non-pain-related sensory fibers to inhibit or prevent, or "gate," nociceptive signals from being relayed from the spinal cord or brainstem to the brain.

Systems and methods of embodiments of the subject invention can benefit any application involving stimulation of the nervous system to restore, enhance, or modulate neurophysiological functions including but not limited to sensory and motor function. For example, in the context of non-invasive (surface) stimulation, embodiments can be implemented to influence the sensory code to study the neural mechanisms of natural touch and develop advanced neuromodulation strategies before deployment in implantable systems. Embodiments can also be used with surface stimulation to deliver targeted neuromodulation therapies for the non-pharmacological management of peripheral neuropathies, including neuropathic pain and sensory deficits secondary to nerve injury. Surface stimulation is a non-invasive neuromodulation approach in which surface electrodes applied on the skin are used to deliver transcutaneous electrical pulses to nearby peripheral nerves, activating afferent pathways. Traditional surface stimulation methods are hampered by inadequate electrode fitting, poor selectivity, motion dependency, and localized discomfort associated with large charge densities. The comfort and selectivity of surface stimulation are often associated with electrode size and charge density. Large electrodes help dissipate the charge over the skin to prevent or inhibit discomfort, reducing selectivity. On the other hand, reducing the size of the electrode can help focalize the stimulation within a given region of tissue, while introducing charge densities that could cause skin discomfort. Transcutaneous neurostimulation typically involves cathode-first biphasic pulses delivered over a pair of small electrodes placed on the same aspect of the target tissue (e.g., wrist, forearm), but displaced longitudinally (i.e., along the long axis of the target nerve). This configuration often results in unintended activation of skin afferents due to localized current densities under the stimulating electrode. In recent studies, surface stimulation of the median and ulnar nerves also resulted in distracting local sensations due to the activation of the tactile afferents in the skin close to the electrodes (see D'Anna et al., 2017, Shin et al., 2018). These sensations can be hard to ignore, affecting the overall performance of the stimulation approach. In contrast, the CHIPS approach of embodiments of the subject invention can utilize pairs of small electrodes placed transversely (across the tissue where the target nerve is located) to deliver anode-first pulses transcutaneously. In this configuration, the delivery of short interleaved pulses results in more selective activation of the target nerve fibers while avoiding the large charge densities that could activate superficial tactile afferents located under the electrodes.

Systems and methods of embodiments of the subject invention can also benefit any application involving nerve stimulation for sensory feedback in virtual reality (VR)/augmented reality (AR) and/or teleoperations. Sensory feedback is important when exploring and acting on the physical world. When grasping objects, cutaneous mechanoreceptors in the fingers provide relevant information about their characteristics and how much force it's being used to grasp them. Electrical neurostimulation can be used to restore this crucial ability by evoking tactile percepts as replacement feedback, conveying task-related information that may help improve the functionality of prosthetic limbs, enhance teleoperation performance and enable individuals to execute virtual or remote manipulation tasks with high precision without relying solely on visual or auditory cues.

Teleoperation of mobile robots has been widely used to perform remote surgical procedures, explore constricted or dangerous environments, transport and dispose of dangerous substances, and carry out firefighting and rescue missions. Some military and police applications include advanced unmanned aerial and terrestrial vehicles, and robotics for explosive device disposal, minimizing risk to personnel (see Kot and Novak, 2018). Immersive VR and AR technologies allow users to interact with virtual environments and even other individuals. This expanding field has had a large influence within the gaming industry and has been widely used for the development of training protocols, data visualization and manipulation in scientific research, and for expanding the options of social interaction within virtual worlds.

A desired feature of teleoperation systems and VR or AR environments is interaction transparency. This is when users cannot distinguish between operating in a local or real environment, and a distant or virtual environment. A critical component of transparency is the provision of the necessary sensory feedback, including visual, auditory, and haptic cues (see Preusche and Hirzinger, 2007). Teleoperators typically control the remote devices out of direct sight, relying on data from sensors and cameras. This requires a complex combination of the operator's cognitive, perceptual, and motor skills (see Lathan and Tracey, 2002). The lack of intuitive feedback from these devices can limit the operator's ability to perform complicated manipulation tasks, especially when trying to complex components such as a manipulator arm with many degrees of freedom. Traditional mechanical haptic feedback interfaces for teleoperation or virtual interaction purposes are limited by the hardware design (see Giachritsis et al., 2009). The size and weight of these devices can be restrictive and could have an effect on feedback perception. This problem can be exacerbated when multiple devices are coupled together to increase the amount of haptic information conveyed to the user.

Electrical neurostimulation can be used to evoke sensations that can be used to convey intuitive haptic feedback for gaming, surgical procedure training, physical and neurological rehabilitation, and social interactions within virtual worlds without the cumbersome restrictions of traditional mechanical feedback systems. The stimulation can potentially replicate real-world interaction cues that could enhance virtual object manipulation tasks and improve the operation of remote-controlled devices. Additionally, this feedback can be used to provide information that is not available in the physical world, such as force limit indicators that serve as training cues to enhance force skill learning during precise telesurgery tasks and surgical simulations.

Implementation of multi-channel stimulation schemes within an electrode array allows for spatial steering of the activation region. This can be leveraged to evoke percepts in different areas of the hand to replicate complex interactions with different types of objects. Additional sensory channels can be added by implementing multi-channel stimulation schemes, where multiple electrode pairs target different parts of the nerve, evoking percepts in different areas of the hand. This can allow for emulation of complex manipulation cues such as size and hardness, object shape, weight, and texture, as well as event cues such as object slippage or breakage. This can enhance teleoperation performance and enable individuals to execute virtual or remote manipulation tasks with high precision without relying solely on visual or auditory cues.

Systems and methods of embodiments of the subject invention can also benefit any application involving stimulating nerves with implanted electrodes. The CHIPS stimulation strategy allows for more focal activation, reducing the volume of tissue that must be stimulated by each electrode to activate a target nerve. This can enable targeting additional nerves (or additional sites within the same nerve) with an array of distributed electrodes without interactions between channels. It can be implemented with minimally invasive subdermal electrodes distributed around the target nerve.

Systems and methods of embodiments of the subject invention can also be applied with extraneural interfaces such as cuff electrodes. The fascicular structure of the nerve and the insulating properties of its connective tissue are known to impair the ability of cuff electrodes to selectively stimulate small populations of fibers, albeit to a much lesser degree than surface stimulation. Attempts to overcome this limitation include reshaping the nerve, increasing the number of electrodes, or selecting specific electrodes to shape the electric field (see Schiefer et al., 2005). The performance of the latter approach can be further enhanced by implementing the distributed electrode arrangement in conjunction with the CHIPS stimulation strategy not only to avoid activating fibers closer to the electrode contacts but also to reduce localized charge densities that could cause tissue damage and electrode degradation.

Turning now to the figures, FIG. 1A shows an experimental setup for testing embodiments of the subject invention on a user (e.g., a human user). In the particular embodiment shown in FIG. 1A, stimulation can be delivered by an optically isolated, current-controlled biostimulator (e.g., TDT RZ5/IZ2H-16) through up to two surface electrode pairs placed around the subject's right forearm (about 3 centimeters (cm) from the distal radial crease). Percept responses (yes/no) were collected using a custom keyboard.

FIG. 1B shows stimulation configurations for testing embodiments of the subject invention using the experimental setup of FIG. 1A. In the particular embodiment shown in FIG. 1B, each electrode pair was assigned to an independent current source: channel 1 (CH1)—blue (solid) and channel 2 (CH2)—red (dashed), in order to deliver charge-balanced biphasic pulses to the median nerve. Two stimulating (s) electrodes were placed on the ventral aspect of the wrist, and two return (r) electrodes on the dorsal aspect. In the single-channel (SC) configuration, only one channel (1A or 2B) delivered stimulation pulses with duration PW, followed by the inter-phase gap (IPG) and charge-balancing phase. In the multi-channel (MC) configuration, stimulation was interleaved from 1A to 2B (3AB) or from 2B to 1A (4BA) so that pulses with the same polarity were delivered sequentially from each channel, with no overlap. In this case, the IPG was the interval between the end of the first trailing pulse and the start of the leading balancing pulse. For a given PW, half of the pulse was delivered by the leading channel and the second half was delivered by the trailing channel, followed by the charge-balancing sequence. The gray inset (bottom-right) illustrates an interleaved biphasic pulse with a delay (Del) between the leading and trailing pulses. The multi-channel IPG was kept constant regardless of the trailing pulse delay used.

Figure 2:
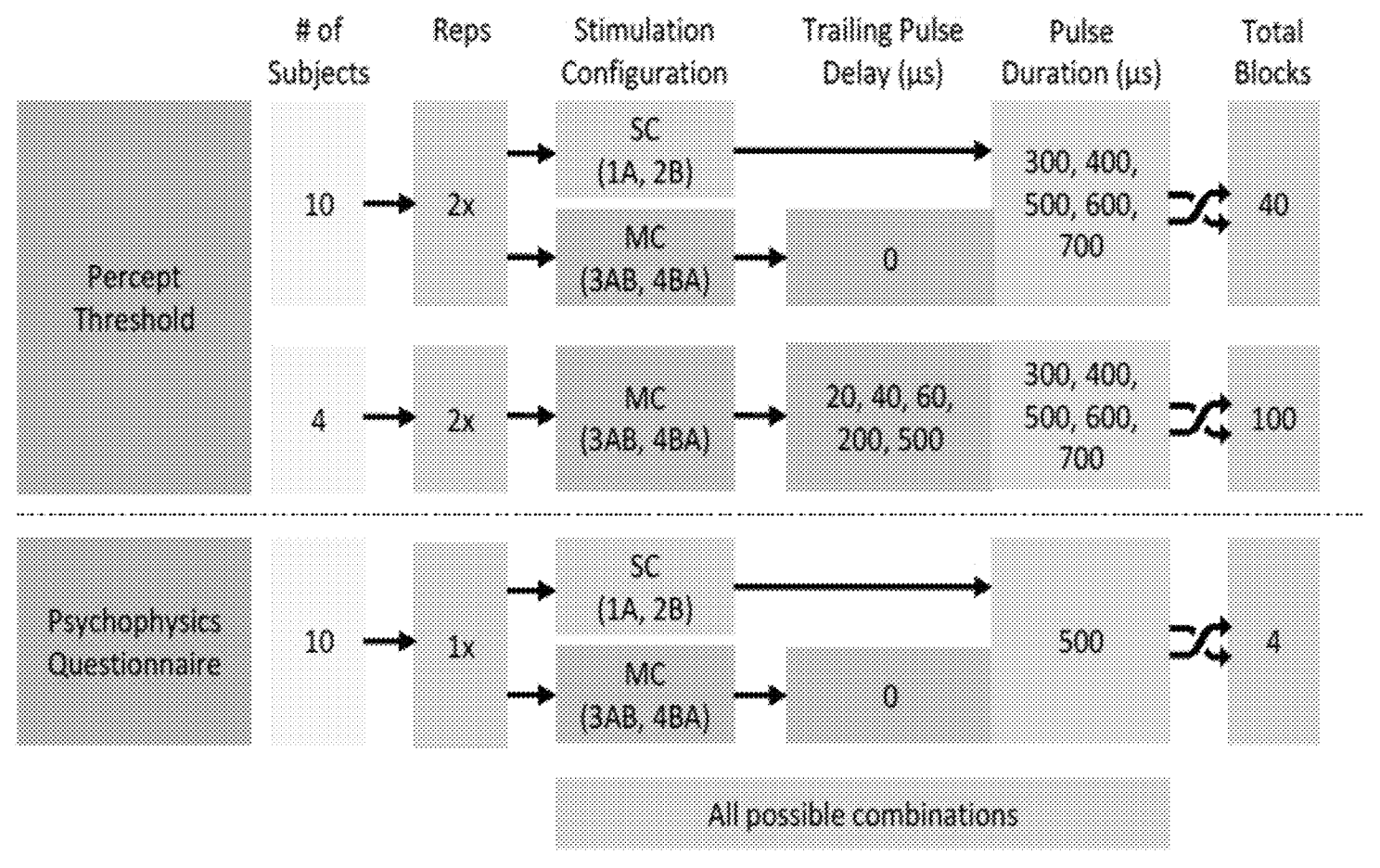

FIG. 2 shows an experiment sequence diagram for human study protocols for testing embodiments of the subject invention. In this particular embodiment, all subjects completed 40 threshold measurement blocks having two reps of five pulse width and four stimulation configurations. A subset of randomly selected subjects completed 100 additional threshold measurement blocks, randomized across two reps of five pulse widths, five trailing pulse delays, and two stimulation configurations. Each subject was assigned a unique (randomized) experimental sequence with all possible combinations of the experimental conditions. Each threshold measurement block took between 30 seconds (s) to 45 s on average. Short breaks between blocks were at least 10 s, and extended as much as the subjects needed. Finally, all subjects completed four questionnaires for all configurations tested. The order of the configuration used for the questionnaires was randomized across all subjects. In FIG. 2, SC represents single-channel, and MC represents multi-channel.

Figure 3:
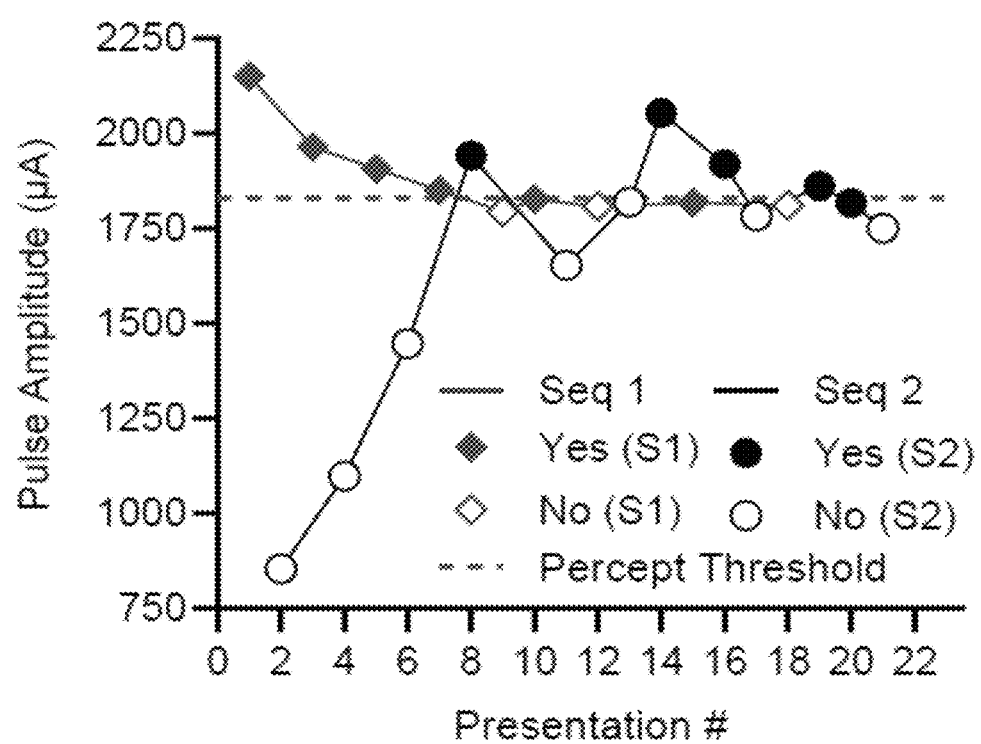
FIG. 3 shows a plot of pulse amplitude (in microamps ($\mu A$)) versus presentation number, illustrating a Dual Randomized Parameter Estimation by Sequential Testing (DR-PEST) procedure to determine percept threshold (example from one subject) according to embodiments of the subject invention.

FIG. 3 shows a plot of pulse amplitude (in microamps (µA)) versus presentation number, illustrating a Dual Randomized Parameter Estimation by Sequential Testing (DR-PEST) procedure to determine percept threshold (example from one subject) according to embodiments of the subject invention. Pulse amplitude can be changed at each trial to elicit sensation based on randomly alternating dual staircase sequences (Seq 1, Seq 2) while collecting Yes or No responses from the subject. The (blue) curve utilizing the diamond data points is for Seq 1, and the (black) curve utilizing the circle data points is for Seq 2.

Figure 4A:
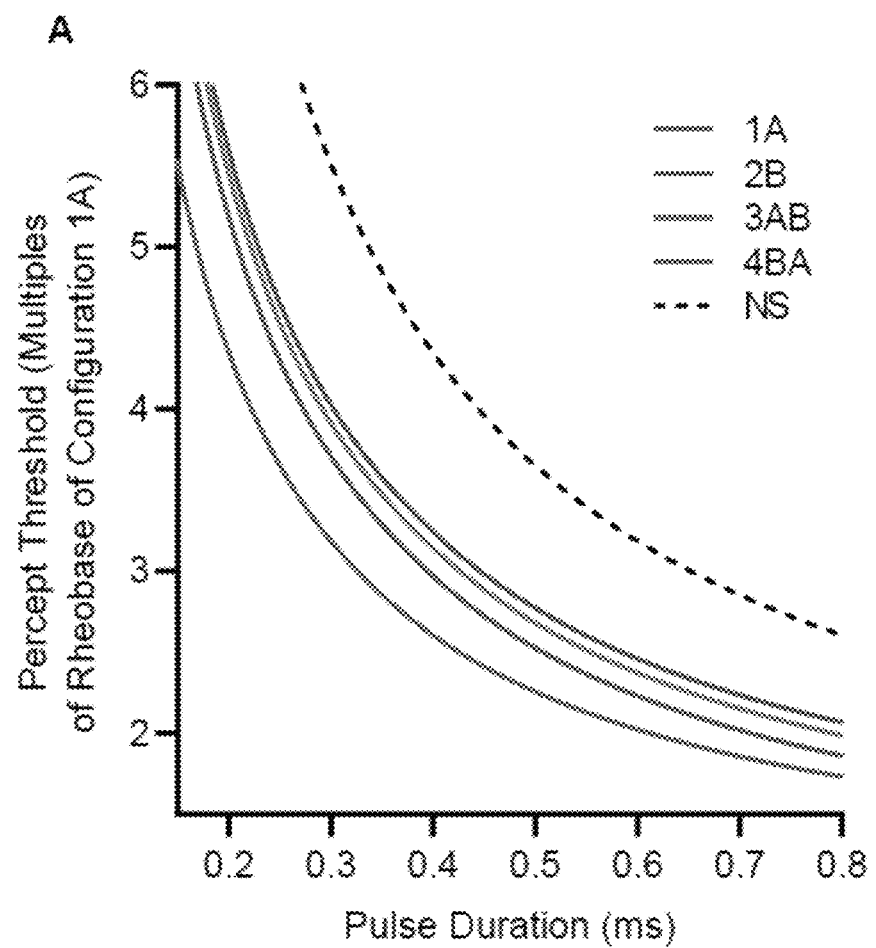
FIG. 4A is a plot of percept threshold (multiples of rheobase of configuration 1A) versus pulse duration (in milliseconds (ms)), illustrating mean strength-duration curves from all participants (Weiss-Lapicque fit) normalized for each subject to the rheobase of the best performing (lowest percept threshold) SC configuration, 1A (blue) as compared to 2B (red) according to embodiments of the subject invention.
Figures 4B, 4C, 4D:
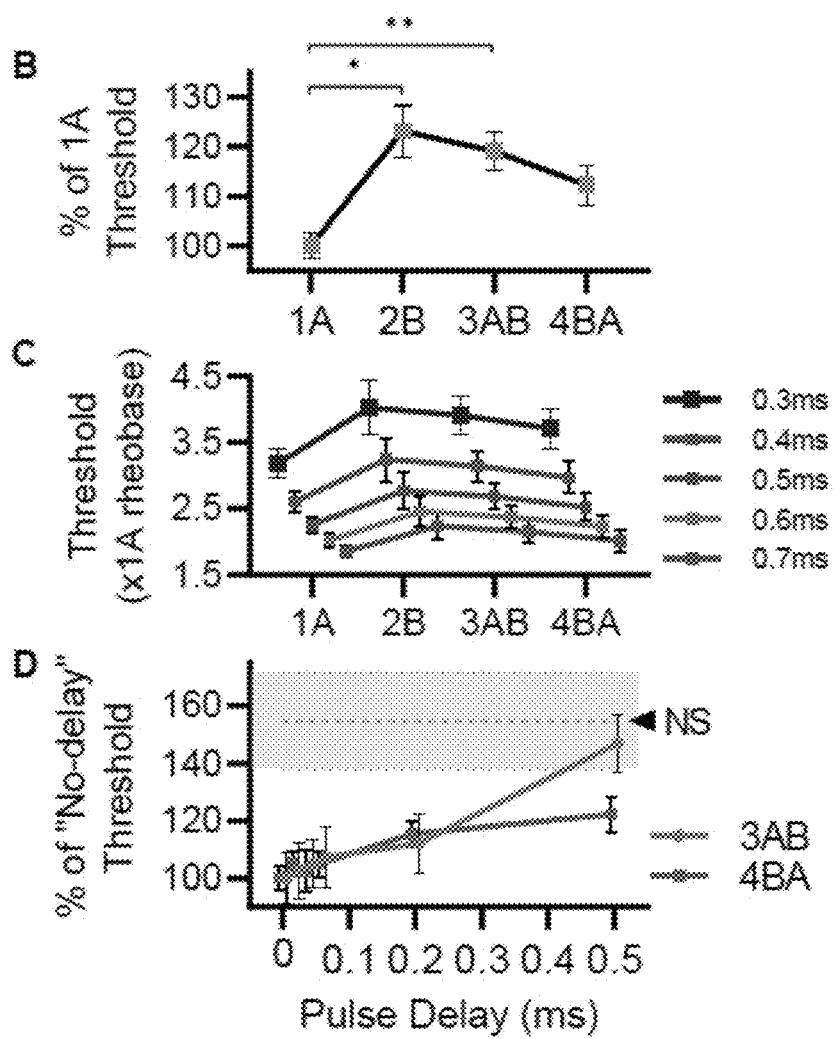
FIG. 4B shows a plot of percentage of 1A threshold for the four stimulation configurations that are also represented in FIG. 4A (1A, 2B, 3AB, and 4BA), illustrating mean normalized PT values adjusted to the percentage of 1A across all PW values tested according to embodiments of the subject invention.
FIG. 4C shows a plot of threshold x1A rheobase for the four stimulation configurations (1A, 2B, 3AB, and 4BA), illustrating mean normalized PT values for each PW tested according to embodiments of the subject invention.
FIG. 4D shows a plot of percentage of "no-delay" threshold versus pulse delay (in ms), illustrating threshold differences under various trailing pulse delays according to embodiments of the subject invention.

FIG. 4A is a plot of percept threshold (multiples of rheobase of configuration 1A) versus pulse duration (in milliseconds (ms)), illustrating mean strength-duration curves from all participants (Weiss-Lapicque fit) normalized for each subject to the rheobase of the best performing (lowest percept threshold) SC configuration, 1A (blue) as compared to 2B (red) according to embodiments of the subject invention. Pulse durations correspond to the total duration of delivered pulses (e.g., a 0.5 ms pulse from 1A or 2B is assumed to have the same duration as two 0.25 ms pulses, interleaved from 3AB or 4BA). A (black) dashed reference SD profile represents the lowest theoretical percept threshold that would be seen if there was no temporal summation (NS) of interleaved pulses. The lowest (blue) curve is for 1B; the second-lowest (purple) curve is for 4BA; the third-lowest (green) curve is for 3AB; and the fourth-lowest (red) curve is for 2B.

FIG. 4B shows a plot of percentage of 1A threshold for the four stimulation configurations that are also represented in FIG. 4A (1A, 2B, 3AB, and 4BA), illustrating mean normalized PT values adjusted to the percentage of 1A across all PW values tested according to embodiments of the subject invention. The bracket with the single asterisk (*) is for $p<0.005$, and the bracket with the double asterisk (**) is for $p<0.001$, post-hoc Dunn-Sidak test.

FIG. 4C shows a plot of threshold x1A rheobase for the four stimulation configurations (1A, 2B, 3AB, and 4BA), illustrating mean normalized PT values for each PW tested according to embodiments of the subject invention. The highest (black) curve is for 0.3 ms PW; the second-highest (blue) is for 0.4 ms PW; the third-highest (green) is for 0.5 ms PW; the second-lowest (orange) is for 0.6 ms PW; the lowest (red) is for 0.7 ms PW.

FIG. 4D shows a plot of percentage of "no-delay" threshold versus pulse delay (in ms), illustrating threshold differences under various trailing pulse delays according to embodiments of the subject invention. Mean percept threshold for 3AB (the (green) curve with the higher value at a pulse delay of 0.5 ms) and 4BA (the (purple) curve with the lower value at a pulse delay of 0.5 ms) were normalized to their rheobase at 0 microseconds (s) delay, and adjusted for all PW values tested. The gray dashed line (at about 155%) and shaded region (from about 140% to about 170%) represent the lowest theoretical percept threshold (mean±SEM) with no temporal summation (NS) based on the performance of 1A.

Figures 5A, 5B, 5C:
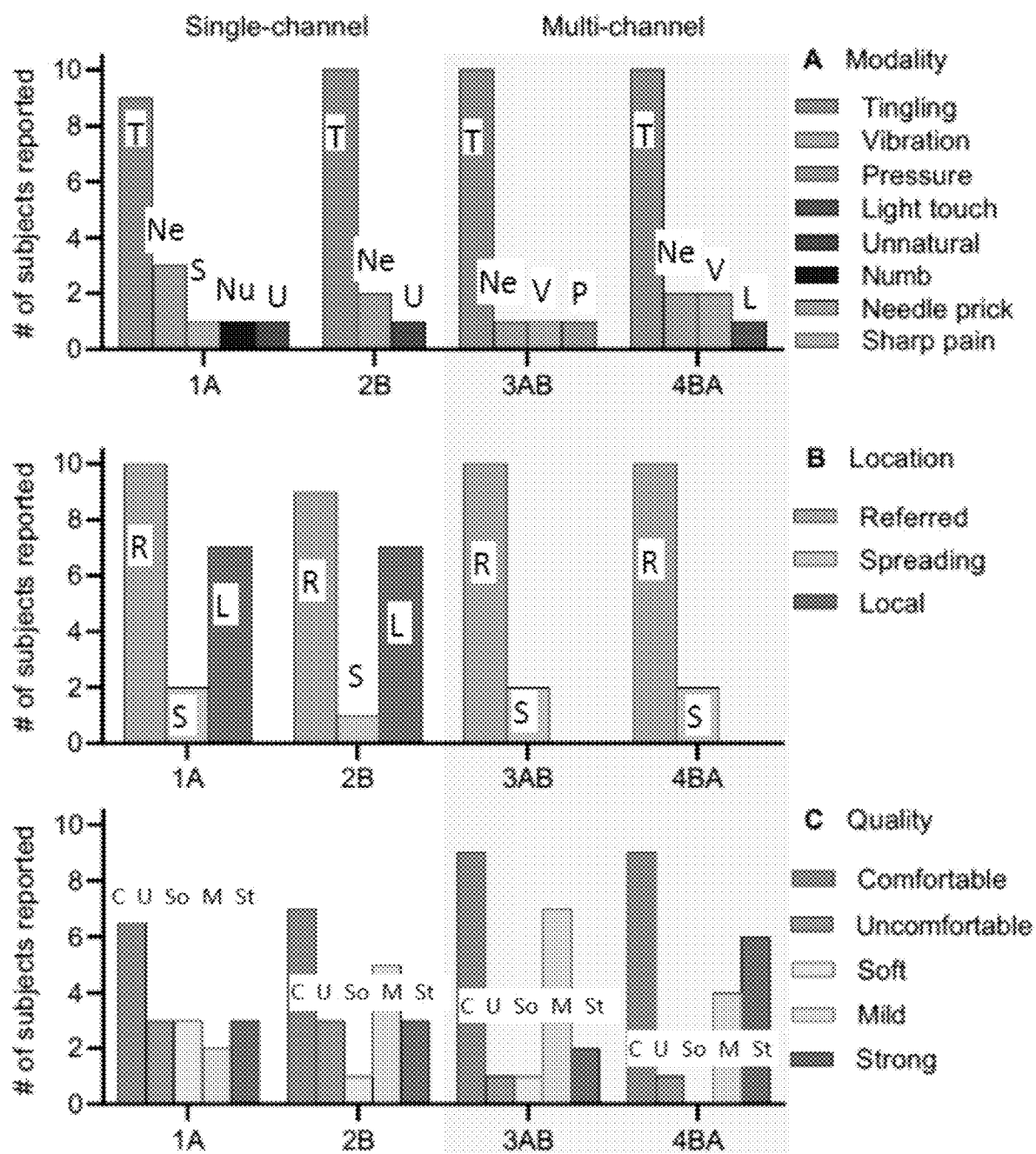
FIG. 5A shows questionnaire results across the four stimulation configurations (1A, 2B, 3AB, and 4BA) illustrating the number of subjects that reported a given percept modality according to embodiments of the subject invention.
FIG. 5B shows questionnaire results across the four stimulation configurations (1A, 2B, 3AB, and 4BA) illustrating the number of subjects that reported a given percept quality according to embodiments of the subject invention.
FIG. 5C shows questionnaire results across the four stimulation configurations (1A, 2B, 3AB, and 4BA) illustrating the number of subjects that reported a given percept location according to embodiments of the subject invention.

FIG. 5A shows questionnaire results across the four stimulation configurations (1A, 2B, 3AB, and 4BA) illustrating the number of subjects that reported a given percept modality according to embodiments of the subject invention, (B) percept quality, and (C) percept location. The maximum possible number of reports for any given percept descriptor was 10. The left-most (light blue) bar in each configuration represents Tingling; the second-left-most (purple) bar in each configuration represents Needle prick; the next two (black, grey) bars in configuration 1A represent Numb and Unnatural, respectively; the right-most two (light-green, grey) bars in configuration 2B represent Sharp pain and Unnatural, respectively; the right-most two (pink, dark-green) bars in configuration 3AB represent Vibration and Pressure, respectively; the right-most two (pink, orange) bars in configuration 4BA represent Vibration and Light touch, respectively. FIG. 5B shows questionnaire results across the four stimulation configurations (1A, 2B, 3AB, and 4BA) illustrating the number of subjects that reported a given percept quality according to embodiments of the subject invention. The maximum possible number of reports for any given percept descriptor was 10. The left-hand (green) stacked-bar in each configuration represents Uncomfortable (striped region) and Comfortable (solid region), respectively; the right-hand (grey-scale) stacked-bar in each configuration represents Unsure/No Resp (unfilled/white region at top in 1A and 2B only), Soft (light grey region in 1A, 2B, and 3AB only), Mild (dark grey region in each configuration), and Strong (black region at bottom in each configuration), respectively.

FIG. 5C shows questionnaire results across the four stimulation configurations (1A, 2B, 3AB, and 4BA) illustrating the number of subjects that reported a given percept location according to embodiments of the subject invention. The maximum possible number of reports for any given percept descriptor was 10. The upper (unfilled/white) region (in configuration 1A only) represents Local-only; the striped region (in configurations 1A and 2B only) represents Local+ Referred; the lower (grey) region (at bottom of the stacked bar in configurations 1A and 2B only, and making up the entire bar configurations 3AB and 4BA only) represents Referred-only. The numerals in parentheses on individual regions represent (#) Spreading.

Figures 6A, 6B, 6C, 6D:
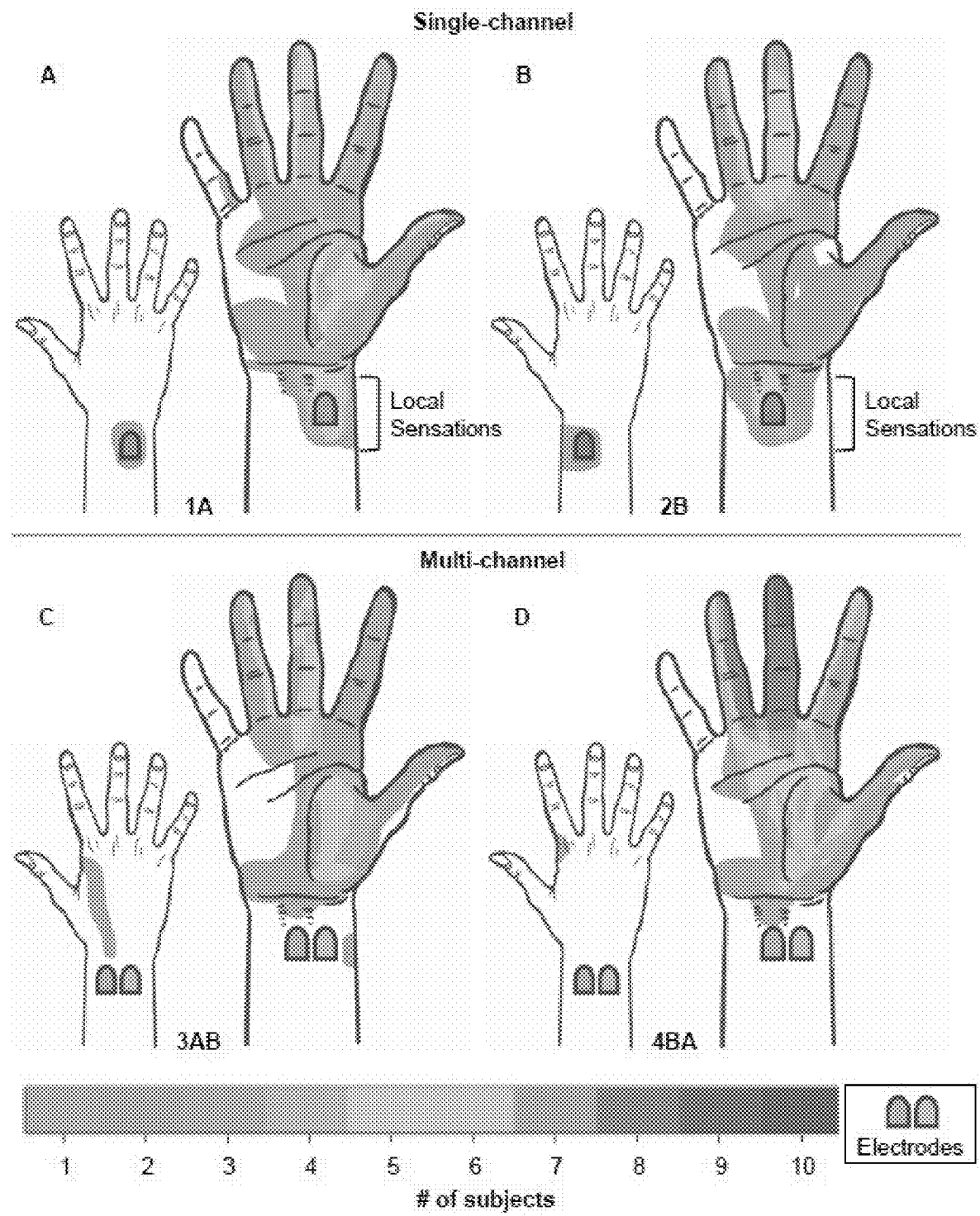
FIGS. 6A-6D show locations of percept regions drawn by all subjects on diagrams of the palmar and dorsal surfaces of the right hand according to embodiments of the subject invention.
Figures 7A, 7B, 7C:
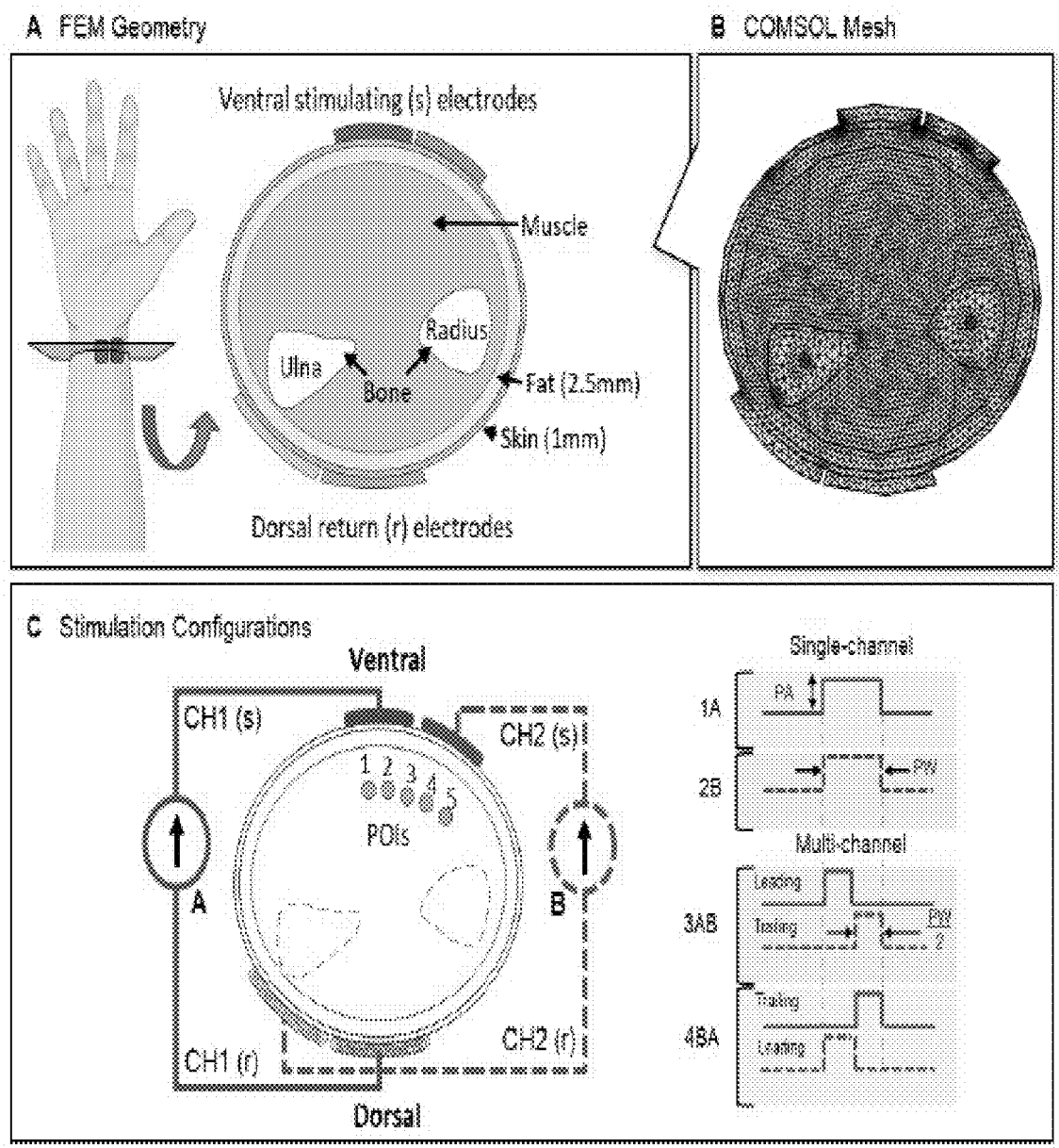
FIGS. 7A-7C show finite element modeling of surface stimulation in a simplified cross-section of a human wrist according to embodiments of the subject invention.

FIGS. 6A-6D show locations of percept regions drawn by all subjects on diagrams of the palmar and dorsal surfaces of the right hand according to embodiments of the subject invention. FIG. 6A shows locations for configuration 1A; FIG. 6B shows locations for configuration 2B; FIG. 6C shows locations for configuration 3AB; and FIG. 6D shows locations for configuration 4BA. All Across all four configurations shown in FIGS. 6A-6D, all subjects reported distally referred sensations across the area of the hand including the ring, middle, index fingers and the thumb. The color scale represents the number of subjects that reported a percept in any given location for each configuration. The red/blue pads on the wrist represent approximate electrode locations for each stimulation configuration. FIGS. 6A and 6B show local sensations under the electrodes that were reported by seven subjects under configurations 1A and 2B, respectively. FIG. 6C shows that a tingle-like sensation was reported by one subject on the lateral surface of the wrist under configuration 3AB (between electrodes, not under). FIG. 6D shows that sensations on the ring and middle fingers, and the palm of the hand, were most consistently reported under configuration 4BA. FIGS. 7A-7C show finite element modeling of surface stimulation in a simplified cross-section of a human wrist according to embodiments of the subject invention. FIG. 7A shows a segmented two-dimensional (2D) geometric structure of a simplified cross-section of the human wrist. Two cortical bone segments representing the ulna and radius were embedded within a 53 millimeter (mm)×41 mm oval-shaped longitudinal muscle region and surrounded by a 2.5 mm homogeneous fat layer and a 1 mm homogeneous skin layer. Two ventral stimulating (s) electrodes and two dorsal return (r) electrodes were placed on the outer surface of the skin layer with a 1 mm inter-electrode gap. FIG. 7B shows fine mesh of the imported geometric structure of the model using free triangular elements in COMSOL. FIG. 7C shows computation of extracellular potential distribution under different stimulation configurations (1A, 2B, 3AB, and 4BA). Each stimulating electrode on the ventral surface was assigned to a return electrode on the dorsal surface such that each "s-r" pair would be an independent stimulation channel (source and sink, respectively) configured such that their current paths would cross each other (e.g., CH1 (s) stimulating electrode is located counter-clockwise and to the left of CH2 (s) stimulating electrode on the top of the model; while CH1 (r) return electrode is located counter-clockwise but to the right of CH2 (r) return electrode on the bottom of the model.) Two stimulation configurations were simulated for different stimulation parameters. Single-channel (SC) stimulation was delivered with only one channel (1A or 2B) while multi-channel (MC) stimulation was interleaved from 1A to 2B (3AB) or from 2B to 1A (4BA).

Figures 8A, 8B, 8C, 8D, 8E:
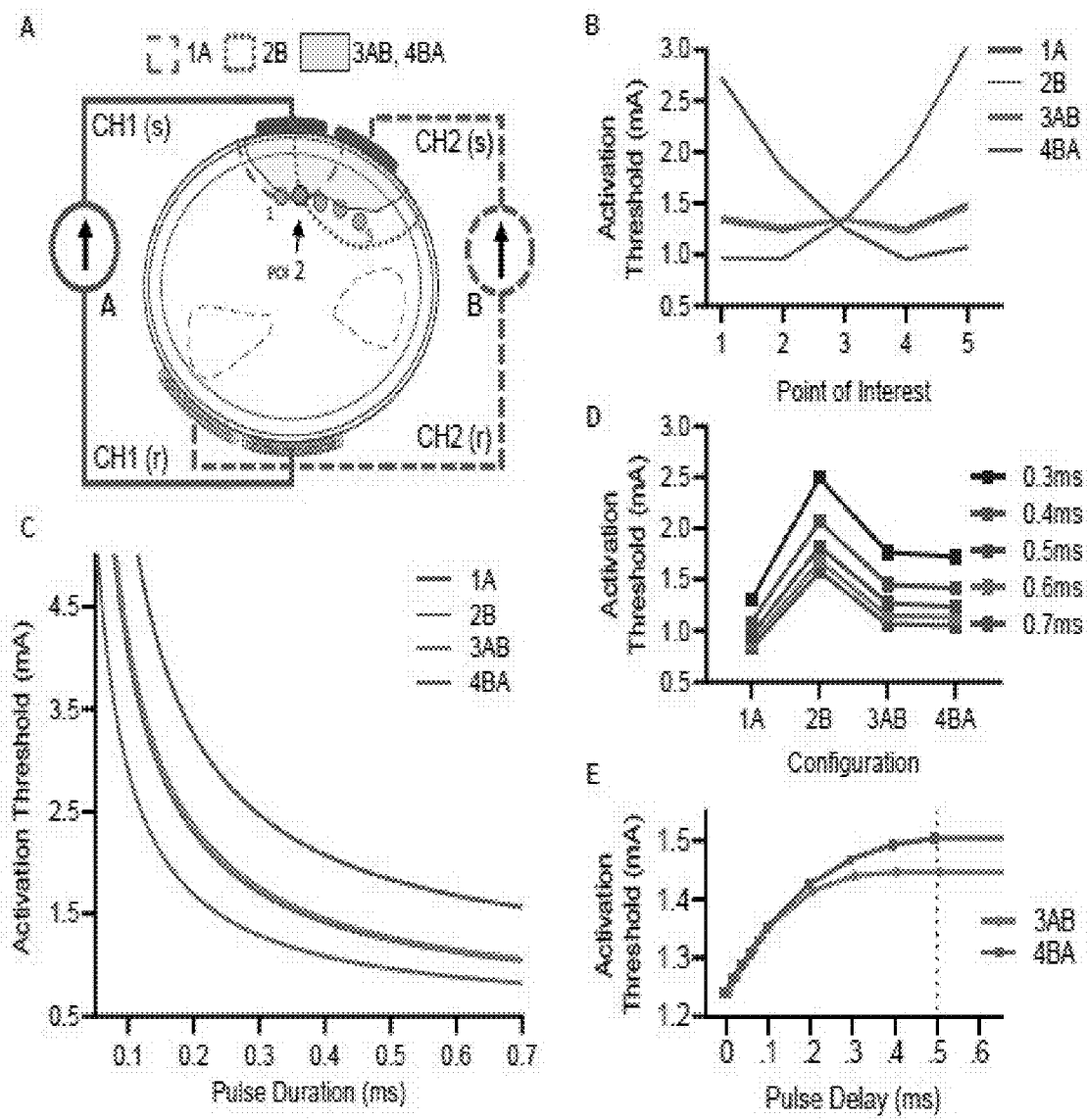
FIGS. 8A-8E show activation performance across stimulation configurations (1A, 2B, 3AB, and 4BA) in a computational model according to embodiments of the subject invention.

FIGS. 8A-8D show activation performance across stimulation configurations (1A, 2B, 3AB, and 4BA) in a computational model according to embodiments of the subject invention. FIG. 8A shows activation regions describing the areas where the axons are likely to be activated within the cross-section of the wrist. Depicted are the regions generated by each configuration when triggering a sensory axon located at the second point of interest (blue-dashed: 1A, red-dotted: 2B, purple (shaded) with green (solid) line: 3AB and 4BA). FIG. 8B shows a plot of activation threshold (in mA) across five points of interest. Single-channel stimulation was provided with 1A and 2B at of PW of 500 s; multi-channel stimulation was provided with channel-hopping interleaved pulse scheduling (CHIPS) with 3AB and 4BA at a PW of 250 s per channel. In FIG. 8B, the (blue) curve with the highest value at point of interest 5 is for 1A; the (red) curve with the lowest value at point of interest 5 is for 2B; the (green) curve with the second-lowest value at point of interest 5 is for 3AB; and the (purple) curve with the second-highest value at point of interest 5 is for 4BA. FIG. 8C shows a plot of activation threshold (in mA) versus pulse duration (in ms), illustrating strength-duration curves for each simulated configuration (Weiss-Lapicque fit) when activating a sensory axon located at the second point of interest. In FIG. 8C, the (blue) curve with the lowest value at 0.5 ms is for 1A; the (red) curve with the highest value at 0.5 ms is for 2B; the (green) curve with the second-highest value at 0.5 ms is for 3AB; and the (purple) curve with the second-lowest value at 0.5 ms is for 4BA. FIG. 8D shows a plot of activation threshold (in mA) versus configuration at different durations, illustrating activation thresholds for each simulated configuration under various pulse durations when activating a sensory axon located at the second point of interest. In FIG. 8D, the (black) curve with the highest values is for 0.3 ms; the (blue) curve with the second-highest values is for 0.4 ms; the (green) curve with the third-highest values is for 0.5 ms; the (orange) curve with the fourth-highest values is for 0.6 ms; and the (red) curve with the lowest values is for 0.7 ms. FIG. 8E shows a plot of activation threshold (in mA) versus pulse delay (in ms), illustrating activation thresholds for 3AB and 4BA at a PW of 250 s per channel, targeting a sensory axon located at the second point of interest under various trailing pulse delays. The dashed vertical line at 0.5 ms indicates the delay value at which the activation thresholds stop increasing. In FIG. 8E, the (green) curve with the lowest value at 0.5 ms is for 3AB; and the (purple) curve with the highest value at 0.5 ms is for 4BA.

Figures 9A, 9B:
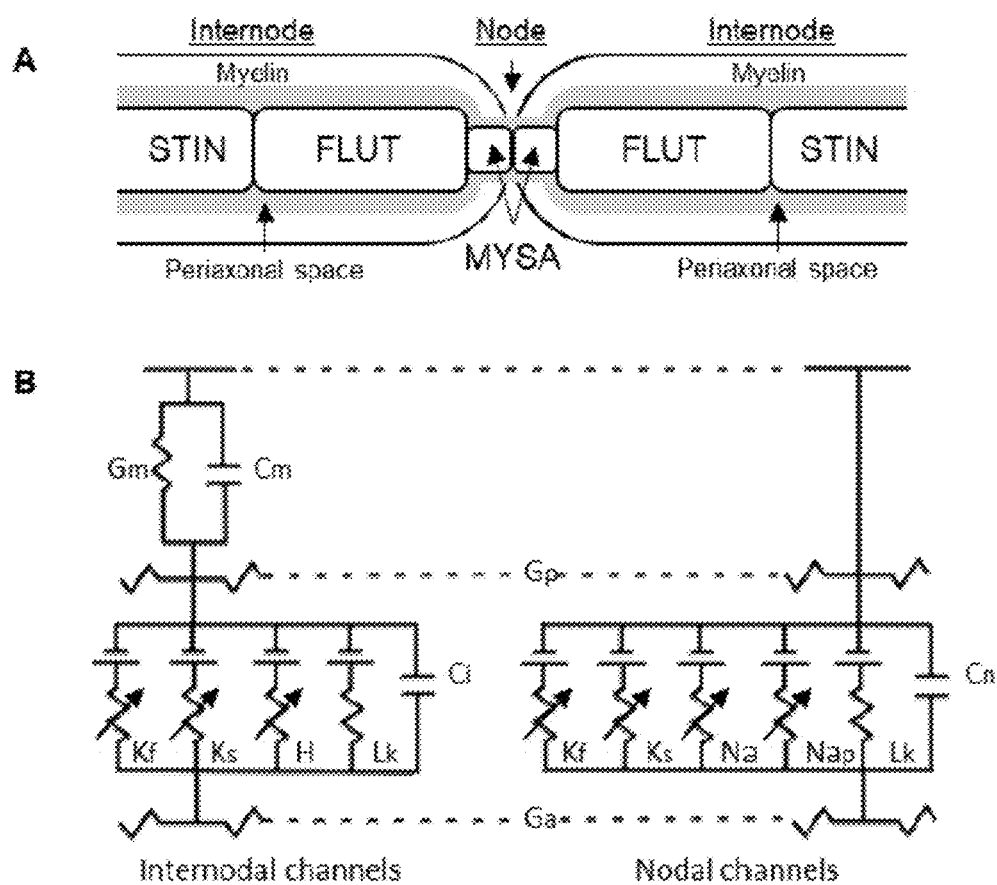
FIGS. 9A-9B show an overview of the sensory axon model implemented in NEURON according to embodiments of the subject invention.

FIGS. 9A-9B show an overview of the sensory axon model implemented in NEURON according to embodiments of the subject invention. FIG. 9A shows overall structure of the sensory axon model which consists of 21 nodes separated by 20 internodes coated in myelin. Each internode consists of two MYSA segments, two FLUT segments, and six STIN segments located between each node of Ranvier. The axon is modeled with 12 m diameter. FIG. 9B shows the ion channels modeled as voltage dependent resistors. This modified MRG model includes fast K+, slow K+, and HCN channels, with leak resistance and internodal capacitance within the internodal segments. Each node has fast K+, slow K+, fast Na+, persistent Na+, and leak channels, with nodal capacitance. Also represented are the conductance and capacitance of the myelin (Gm and Cm), the axoplasmic conductance (Ga), and the periaxonal conductance (Gp).

FIG. 10 shows the MQL Questionnaire to assess the Modality (Q1), Quality (Q2) and Location (Q3) of the elicited percepts according to embodiments of the subject invention. A diagram of the palmar and dorsal surfaces of the right hand (Q4) was used to assess the elicited percept areas.

Figure 11:
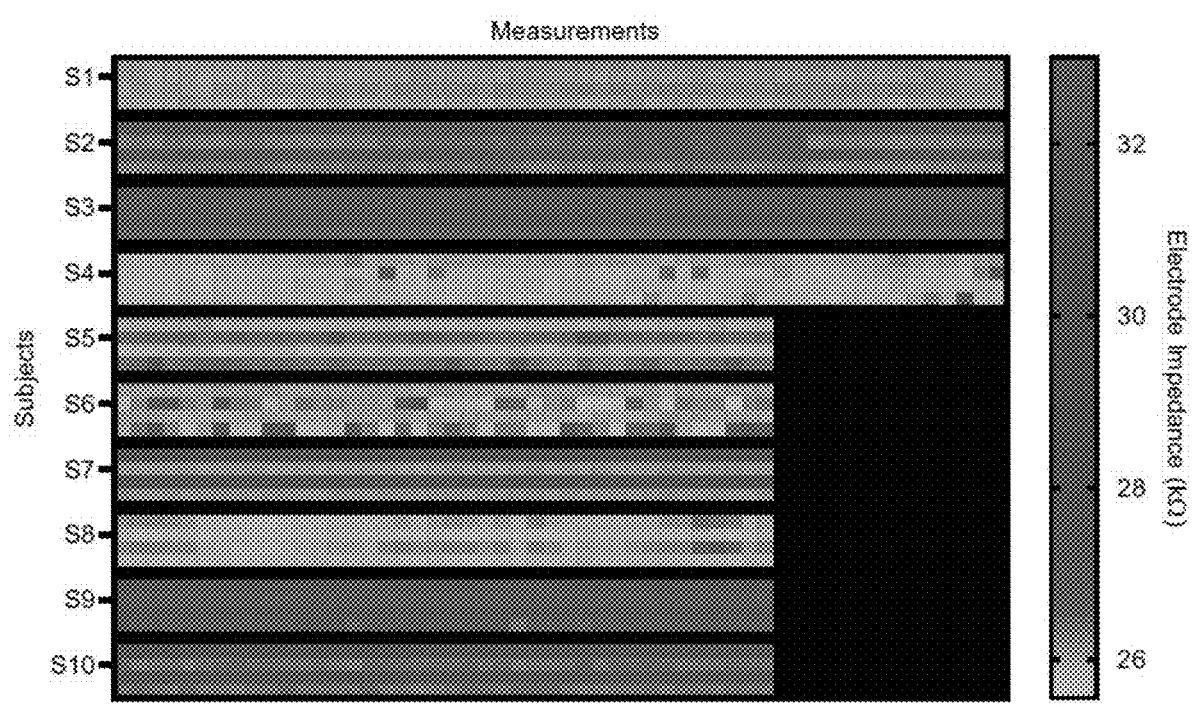
FIG. 11 shows surface electrode impedances, according to embodiments of the subject invention, which were stable throughout the study.

FIG. 11 shows surface electrode impedances, according to embodiments of the subject invention, which were stable throughout the study. The impedance measurements (kΩ) for each electrode were recorded at the start of every block during the regular threshold measurement trials. Additional impedance measurements were done with 4 subjects over 14 trials spread across the additional pulse delay trials. Each colored square is an individual impedance value collected at different measurement times (x-axis). All electrode impedance values were less than 30 kΩ (26.4±0.5 kΩ; mean±SD) for all subjects.

Figures 12A, 12B:
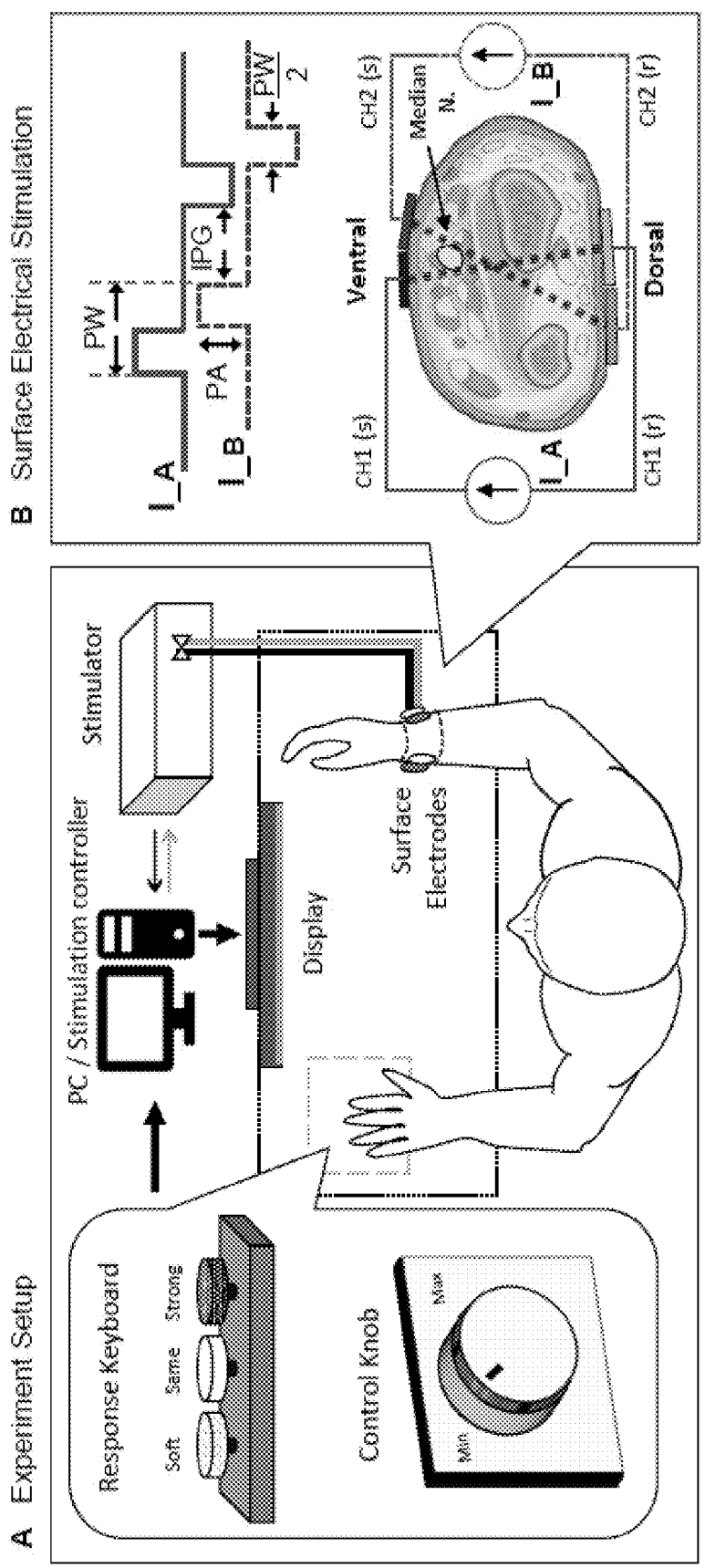
FIGS. 12A-12B show an experiment setup for surface electrical stimulation according to embodiments of the subject invention.

FIGS. 12A-12B show an experiment setup for surface electrical stimulation according to embodiments of the subject invention. FIG. 12A illustrates how able-bodied subjects were seated on a chair with both arms on a table in front of them. A custom 3-button keyboard and a control knob were placed next to the subject's left hand. A computer screen was placed in front of them at eye level. The keyboard was used to provide percept responses, while the knob was used to adjust various stimulation parameters at different stages of the study. FIG. 12B illustrates how charge-balanced biphasic stimulation pulses were delivered by a current-controlled biostimulator (TDT RZ5/IZ2H-16) from two independent current sources (CH1 & CH2) to two stimulating (s) surface electrodes on the ventral aspect of the wrist (~3 cm from the distal radial crease), and two return (r) electrodes on the dorsal aspect. PA=Pulse Amplitude; PW=Pulse Duration; IPG=Inter-phase Gap.

Figures 13A, 13B:
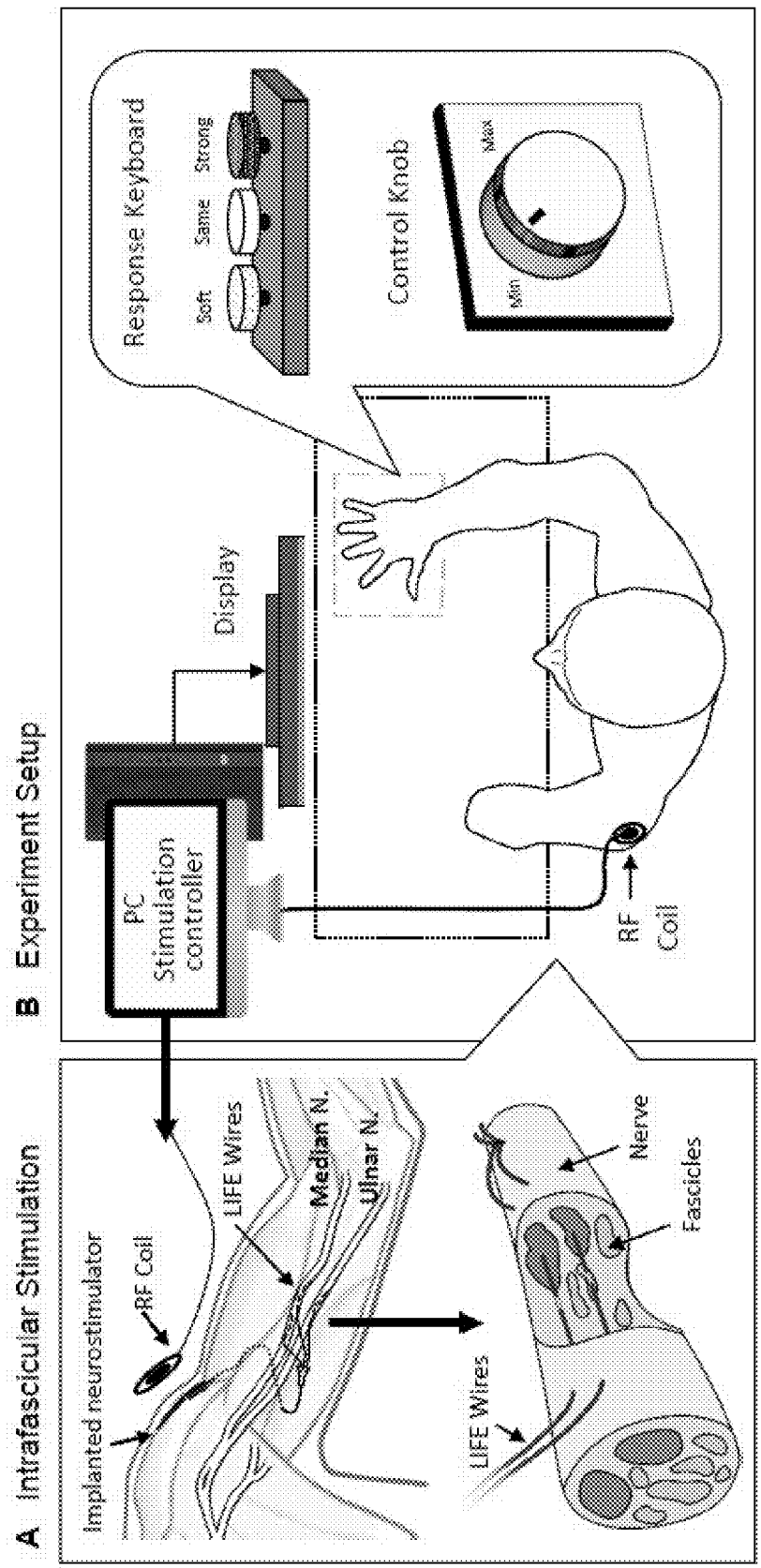
FIGS. 13A-13B show a setup for intrafascicular stimulation according to embodiments of the subject invention.

FIGS. 13A-13B show a setup for intrafascicular stimulation according to embodiments of the subject invention. FIG. 13A illustrates an implanted multi-channel neurostimulator connected to a distributed intrafascicular multielectrode (DIME) system consisting of a trifurcated lead attached to 15 LIFEs implanted longitudinally inside fascicles of the median and ulnar nerves. Stimulation parameters and power are transcutaneously communicated via an RF coil to the receiving antenna of the implanted neurostimulator. FIG. 13B illustrates how the subject was seated on a chair with the left residual forearm and the right arm on a table in front of him. A custom 3-button keyboard and a control knob were placed next to the subject's right hand. A computer screen was placed in front of him at eye level. The keyboard was used to provide percept responses, while the knob was used to adjust various stimulation parameters at different stages of the study. LIFE=Longitudinal intrafascicular electrode; PC=Personal computer; RF=Radio frequency.

Figures 14A, 14B:
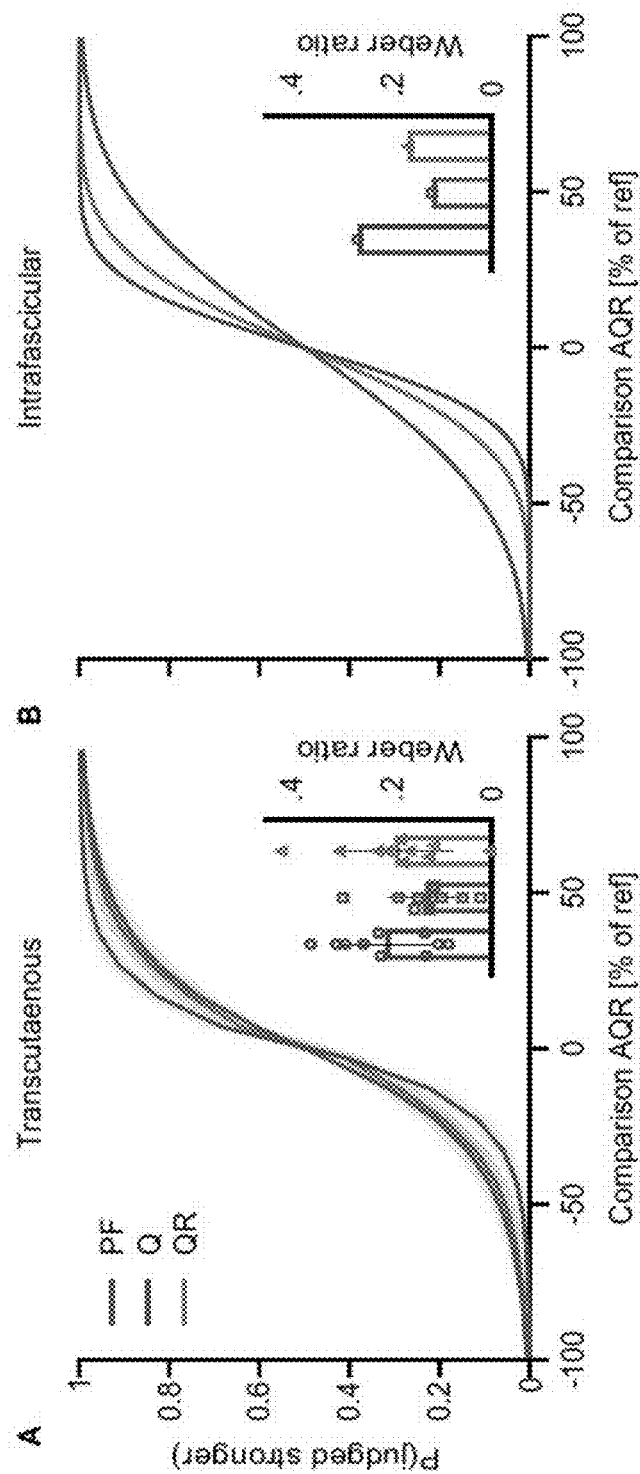
FIGS. 14A-14B show psychometric functions relating percept intensity discrimination performance to changes in charge-rate according to embodiments of the subject invention.

FIGS. 14A-14B show psychometric functions relating percept intensity discrimination performance to changes in charge-rate according to embodiments of the subject invention. The curves indicate the probability of judging the presented stimuli correctly, i.e., stronger, same or weaker than the reference during modulation of PF (blue; highest value from −100% of ref AQR to approaching 0% of ref AQR; lowest value from above 0% of ref AQR to +100% of ref AQR), Q (red; lowest value from −100% of ref AQR to approaching 0% of ref AQR; highest value from above 0% of ref AQR to +100% of ref AQR) and QR (green; middle value from −100% of ref AQR to approaching 0% of ref AQR; middle value from above 0% of ref AQR to +100% of ref AQR). Data was similar between FIG. 14A and FIG. 14B, with all three curves following an "S" pattern, crossing each other and also changing concavity at Comparison AQR [% of ref]=0 (all curves were concave-up below 0% and concave-down above 0%). There was greater separation between curves and a wider range of curvatures in FIG. 14B, as compared to FIG. 14A. FIG. 14A shows combined psychometric curves from 10 able-bodied subjects. Solid lines represent the mean performance across subjects for each stimulation condition. Shaded area denotes the SEM. (Inset) Weber ratios for all able-bodied subjects were consistent across the stimulation conditions (one-way ANOVA, $p=0.1639$). Symbols denote all data; bars denote the mean±SD. The left-most (blue) bar and symbols (circles) represent PF. The center (red) bar and symbols (squares) represent Q. The right-most (green) bar and symbols (triangles) represent QR. FIG. 14B shows percept intensity discrimination performance for intrafascicular stimulation in a subject with a transradial amputation. (Inset) Weber ratios for PF, Q and QR modulation were comparable to those of able-bodied subjects across the stimulation conditions (one sample t test, $p=0.10$, 0.61, and 0.50). The left-most (blue) bar and symbol (circle) represent PF. The center (red) bar and symbol (square) represent Q. The right-most (green) bar and symbol (triangle) represent QR. PF=Pulse Frequency; Q=Charge; QR=Charge Rate. In both cases changes in charge were easier to detect, and intensity discrimination performance during charge-rate (QR) modulation was between that of charge (Q) and frequency (PF).

Figures 15A, 15B, 15C, 15D:
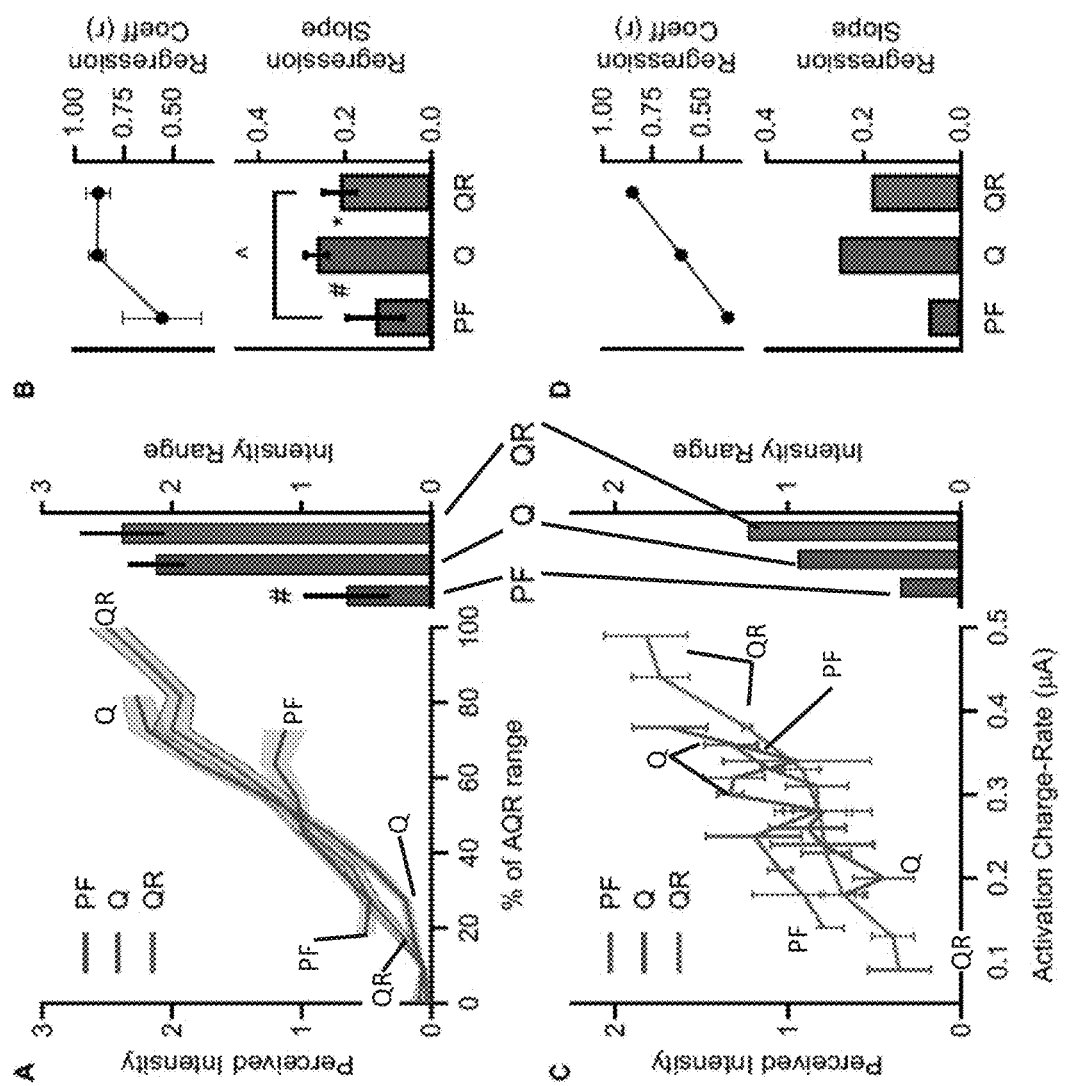
FIGS. 15A-15D illustrate how stimulation charge-rate influences percept intensity according to embodiments of the subject invention.

FIGS. 15A-15D illustrate how stimulation charge-rate influences percept intensity according to embodiments of the subject invention. Ratings were normalized by dividing open-ended reports of perceived strength levels by the grand mean rating on their respective blocks, after manipulations of PF (blue), Q (red) or QR (green) as the combination of PF and Q. FIG. 15A shows normalized perceived intensity as a function of the activation charge-rate range used for each subject. Solid lines indicate the mean ratings across 10 able-bodied subjects (n=3 ratings per level from each subject) for each stimulation condition. Shaded area denotes the SEM. (Inset) Normalized intensity ranges (mean±SD) across all able-bodied subjects showing a narrower range during PF modulation than for Q and QR (post hoc Tukey). FIG. 15B shows a comparison of regression slopes and regression coefficients (mean±SD across subjects) obtained when varying PF, Q, or QR. Slopes were different for all conditions. Intensity was correlated to both Q and QR modulation. FIG. 15C shows normalized perceived intensity as a function of activation charge-rate for intrafascicular stimulation in a subject with a transradial amputation. Solid lines indicate mean ratings (n=3 ratings per level); error bars denote the SEM. (Inset) Normalized intensity ranges showing a narrower range during PF modulation. FIG. 15D shows Comparison of regression slopes and regression coefficients obtained when varying PF, Q, or QR during intrafascicular stimulation. Slopes were different for all conditions. Intensity was strongly correlated to QR modulation. (*$p<0.05$, ^$p<0.01$, #$p<0.001$). PF=Pulse Frequency; Q=Charge; QR=Charge Rate. Subjects perceived a wider range of intensities with QR modulation. Perceived intensity increased when Q or PF were increased over their operational range. Regression slopes were steepest for Q, shallowest for PF, and intermediate for QR. In both cases QR was strongly correlated to percept intensity, and a wider range of intensities was observed under QR modulation.

Figure 16B:
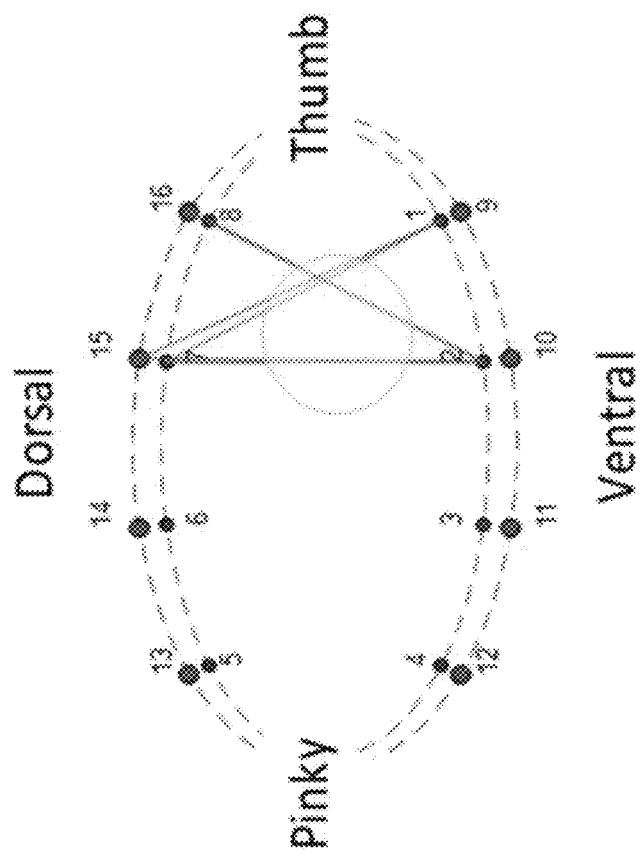
FIGS. 16A-16D show an electrode array according to embodiments of the subject invention.
Figure 16A:
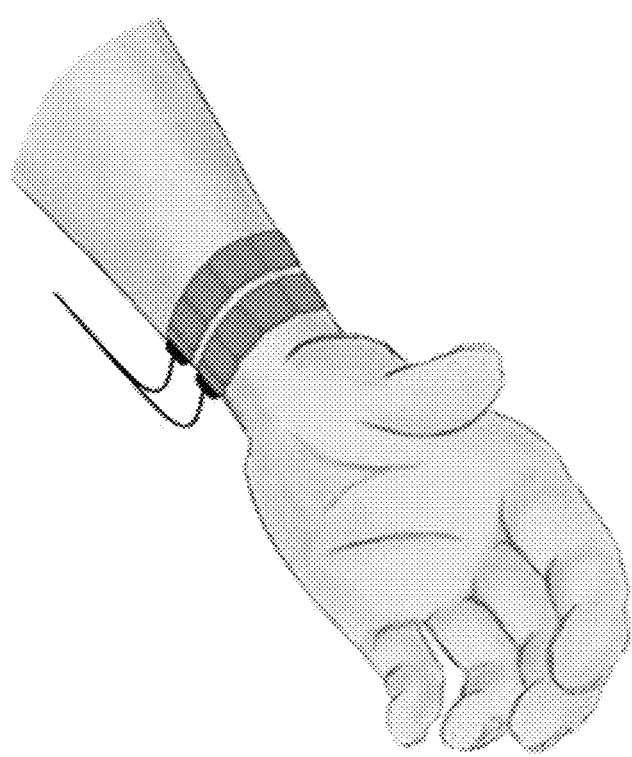
Figure 16D:
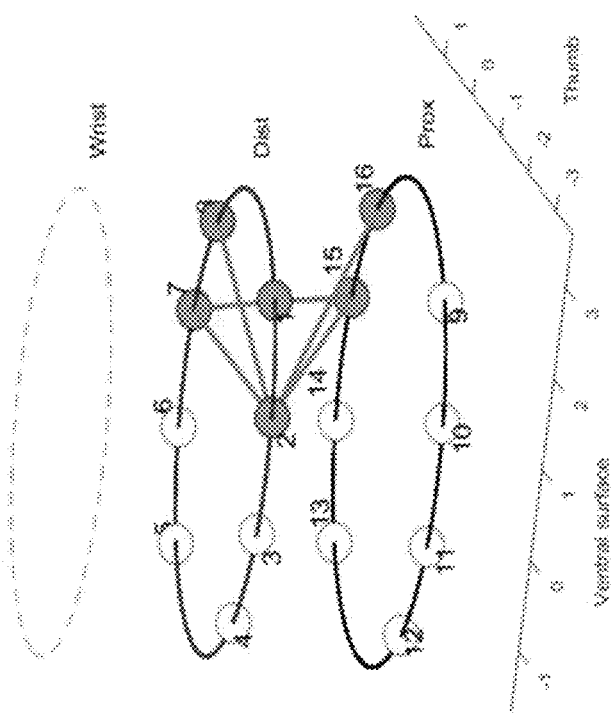
Figure 16C:
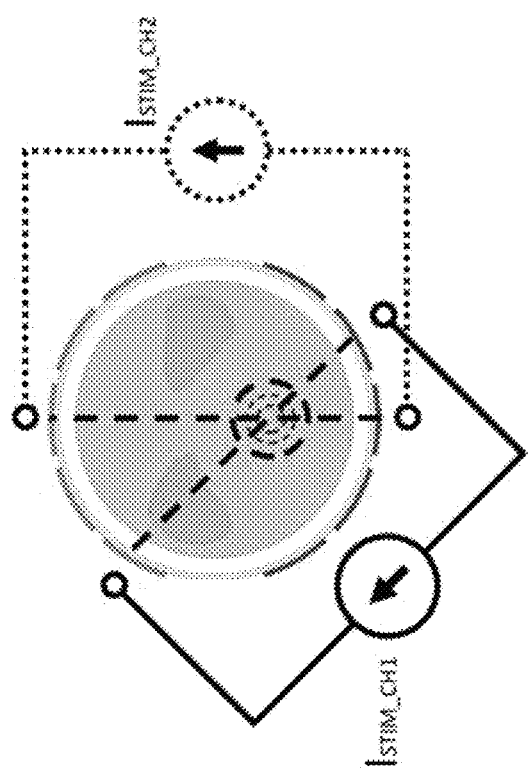

FIGS. 16A-16C show questionnaire responses across all stimulation configurations. The bar plots represent the number of subjects that reported a given (FIG. 16A) percept modality, (FIG. 16B) percept quality, and (FIG. 16C) percept location. The maximum possible number of reports for any given percept descriptor was 10.

FIGS. 17A-17D show location of the percept regions drawn by all subjects on diagrams of the palmar and dorsal surfaces of the right hand. All subjects reported distally referred sensations across the area of the hand including the ring, middle, index fingers and the thumb. The color scale represents the number of subjects that reported a percept in any given location. (FIG. 17A, FIG. 17B) Local sensations under the electrodes were reported by 7 subjects under configurations 1A and 2B. (FIG. 17C) A tingle-like sensation was reported by 1 subject on the lateral surface of the wrist under configuration 3AB (between electrodes, not under). (FIG. 17D) Sensations on the ring and middle fingers, and the palm of the hand were most consistently reported under configuration 4BA. The red/blue pads on the wrist represent approximate electrode locations for each stimulation configuration.

FIGS. 16A-16D show an electrode array according to embodiments of the subject invention. FIG. 16A illustrates one configuration of an electrode array having a proximal loop and a distal loop around the wrist of a human subject. FIG. 16B shows a schematic of electrode naming and a potential signal path mapping using the electrodes of the array. FIG. 16C shows a simplified cross-sectional representation of a pair of signal paths intersecting to stimulate a nerve. FIG. 16D shows a 3-dimensional representation of a potential signal path mapping using the electrodes of the array.

Figure 17:
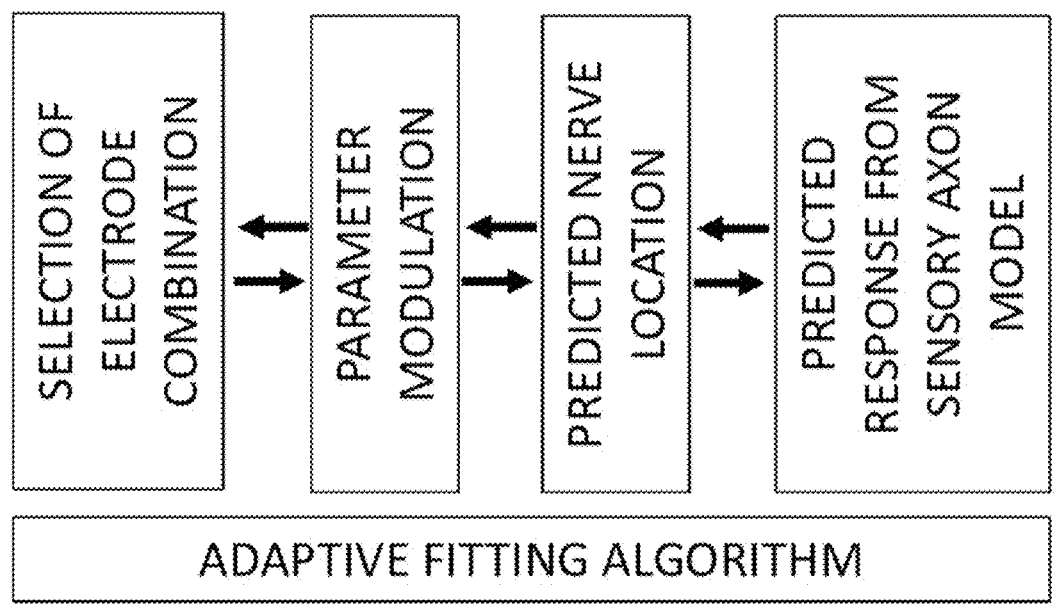
FIG. 17 shows a block diagram of an adaptive fitting algorithm process according to an embodiment of the subject invention.

FIG. 17 shows a block diagram of an adaptive fitting algorithm process according to an embodiment of the subject invention. The adaptive fitting algorithm iterates between steps including selection of electrode combination, parameter modulation, predicted nerve location, and predicted response from sensory axon model.

Figure 18:
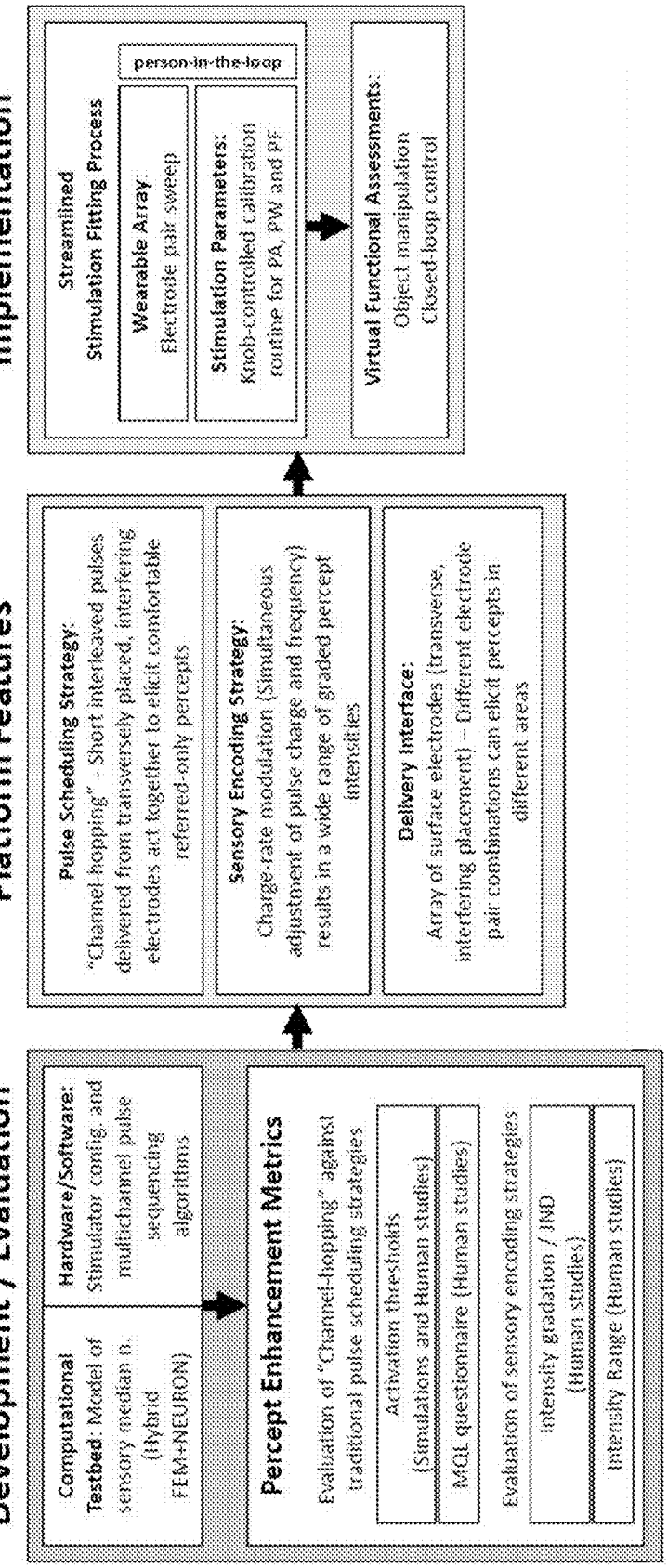
FIG. 18 illustrates a block diagram representing an Enhanced Surface Electrical Neurostimulation (eSENS) Platform according to embodiments of the subject invention.

FIG. 18 illustrates a block diagram representing an Enhanced Surface Electrical Neurostimulation (eSENS) Platform according to embodiments of the subject invention. A development and evaluation module uses computational modelling, hardware, and software configurations to drive percept enhancement metrics. The output of the development and evaluation module drives platform features including pulse scheduling, sensory encoding, and delivery to support implementation with a streamlined stimulation fitting process and virtual functional assessments.

The methods and processes described herein can be embodied as code and/or data. The software code and data described herein can be stored on one or more machine-readable media (e.g., computer-readable media), which may include any device or medium that can store code and/or data for use by a computer system. When a computer system and/or processor reads and executes the code and/or data stored on a computer-readable medium, the computer system and/or processor performs the methods and processes embodied as data structures and code stored within the computer-readable storage medium.

It should be appreciated by those skilled in the art that computer-readable media include removable and non-removable structures/devices that can be used for storage of information, such as computer-readable instructions, data structures, program modules, and other data used by a computing system/environment. A computer-readable medium includes, but is not limited to, volatile memory such as random access memories (RAM, DRAM, SRAM); and non-volatile memory such as flash memory, various read-only-memories (ROM, PROM, EPROM, EEPROM), magnetic and ferromagnetic/ferroelectric memories (MRAM, FeRAM), and magnetic and optical storage devices (hard drives, magnetic tape, CDs, DVDs); network devices; or other media now known or later developed that are capable of storing computer-readable information/data. Computer-readable media should not be construed or interpreted to include any propagating signals. A computer-readable medium of embodiments of the subject invention can be, for example, a compact disc (CD), digital video disc (DVD), flash memory device, volatile memory, or a hard disk drive (HDD), such as an external HDD or the HDD of a computing device, though embodiments are not limited thereto. A computing device can be, for example, a laptop computer, desktop computer, server, cell phone, or tablet, though embodiments are not limited thereto.

When ranges are used herein, combinations and subcombinations of ranges (e.g., subranges within the disclosed range), specific embodiments therein are intended to be explicitly included. When the term "about" is used herein, in conjunction with a numerical value, it is understood that the value can be in a range of 95% of the value to 105% of the value, i.e. the value can be +/−5% of the stated value. For example, "about 1 meter" means from 0.95 meters to 1.05 meters.

The transitional term "comprising," "comprises," or "comprise" is inclusive or open-ended and does not exclude additional, unrecited elements or method steps. By contrast, the transitional phrase "consisting of" excludes any element, step, or ingredient not specified in the claim. The phrases "consisting" or "consists essentially of" indicate that the claim encompasses embodiments containing the specified materials or steps and those that do not materially affect the basic and novel characteristic(s) of the claim. Use of the term "comprising" contemplates other embodiments that "consist" or "consisting essentially of" the recited component(s).

A greater understanding of the embodiments of the subject invention and of their many advantages may be had from the following examples, given by way of illustration. The following examples are illustrative of some of the methods, applications, embodiments, and variants of the present invention. They are, of course, not to be considered as limiting the invention. Numerous changes and modifications can be made with respect to the invention.

Materials and Methods for the Following Examples

Written informed consent was obtained from ten adult subjects (four males, six females, mean age±SD: 34.9±15.3) in compliance with the Institutional Review Board of Florida International University. All prospective subjects were screened prior to the study to determine eligibility. Subjects were able-bodied, with no sensory disorders or any self-reported condition listed as a contraindication for transcutaneous electrical stimulation (pregnancy, epilepsy, lymphedema, or cardiac pacemaker).

Subjects were seated on a chair with both arms on a table in front of them (see FIG. 1A). Their right forearm was thoroughly cleaned with an alcohol wipe and placed on a support pad on the table, with their right hand's palmar surface parallel to the vertical plane. Subjects were encouraged to drink water before and during the experiment to ensure sufficient skin hydration.

Each subject received electrical stimulation from a set of four self-adhesive hydrogel surface electrodes (Rhythmlink International LLC, Columbia, S.C.) distributed around their right wrist to activate sensory fibers in the median nerve which emanate from the index, middle, and part of the ring finger. Two small stimulating (s) electrodes (15 mm×20 mm) were placed on the ventral aspect of the wrist (about 3 cm from the distal radial crease) and two large return (r) electrodes (20 mm×25 mm) on the opposite (dorsal) side (see FIG. 1). Each "s-r" electrode pair was assigned to an independent channel and configured such that their current paths would cross each other and intersect the median nerve transversely (FIG. 1).

Placement of the first "s-r" pair was determined by fixing the return (dorsal) electrode near the styloid process of the ulna, and adjusting the stimulating (ventral) electrode near the median nerve while providing brief, is long stimulation bursts (500 microsecond (μs) biphasic, anode-first pulses at 30 Hertz (Hz)) at various amplitude levels between 1.5 milliamps (mA) and 3 mA, in increments of 0.1 mA, until a distinct referred sensation was reported by the subject. The location that elicited a percept with the lowest amplitude was chosen. The dorsal electrode from the second "s-r" pair was placed lateral to the first one, near the dorsal tubercle of the radius. Similarly, the second ventral electrode was placed medial to the first one, keeping an approximately 1 mm gap between them. Again, short stimulation bursts at various amplitude levels were delivered from the second electrode pair until a distinct referred sensation was reported by the subject. Then, the location of the ventral electrodes was adjusted further by shifting them together laterally so that both would elicit a distinct referred sensation with the lowest possible stimulation amplitude.

A custom 3-button keyboard was placed on the table in front of the subject's left hand. Subjects used this keyboard to trigger the delivery of the electrical stimuli (Go) and provide percept responses (Yes/No). Subjects were fitted with a pair of noise cancelling headphones that delivered soft white noise to mask any ambient sounds that might be distracting as well as to play instruction sound queues at various stages of the study. Subjects were instructed to relax and maintain a fixed arm position throughout the experiment but were encouraged to stretch and move their hand during periodic breaks to avoid discomfort. Subjects were asked about their comfort levels, or if additional breaks were needed after each task.

A multi-channel programmable, optically isolated bench-top bio-stimulator (TDT IZ2-16H, Tucker-Davis Technologies, Alachua Fla. USA) was used to deliver the electrical stimuli. A custom TDT Synapse stimulation control environment running on the TDT RZ5D base processor was used to schedule charge-balanced, current-controlled biphasic rectangular pulses with pulse amplitudes (PA) between ±3 mA per channel, with 1 microamp (μA)/step resolution, and a pulse width (PW) resolution of 21 μs/step. Anode-first pulses were used throughout the study, as this waveform has been shown to activate orthogonally oriented fibers more efficiently than cathode-first pulses and resulted in lower percept thresholds than cathode-first pulses when stimulating the median nerve transversely during pilot studies. The TDT Synapse environment was interfaced to a custom MATLAB® program (v2018b, MathWorks® Inc, Natick, Mass.) designed to run and monitor the various study conditions and modulate the stimulation parameters based on subject responses.

A computational model of human median nerve afferents within the wrist (according to an embodiment of the subject invention as described herein) was used to develop and characterize the CHIPS strategy before its implementation in human studies. The model helped to visualize the potential outcomes of implementing this novel pulse scheduling scheme (see FIGS. 7A-7C). It provided the means to explore and narrow down the stimulation parameter space. These parameters were further refined during pilot experiments. The activation threshold results from the computational study were used to guide electrode placement procedures used during human subject studies. For instance, electrode pairs from each channel used in CHIPS were configured such that their current paths would cross each other and intersect the median nerve transversely. In this configuration, electrode locations with the lowest single-channel thresholds would suggest that the target nerve is located between both stimulating electrodes. Based on the simulation results, this placement was expected to result in better targeting of the nerve when stimulating with the CHIPS strategy according to embodiments (see FIG. 8B), avoiding unnecessarily larger activation regions for either of the channels.

Two stimulation configurations were used (see FIG. 1). During standard single-channel (SC) stimulation, biphasic current pulses with a 100 μs inter-phase gap (IPG) and a given PW were delivered to the median nerve from only one channel at a time (configuration pattern 1A or 2B). For the multi-channel (MC) configurations used to test the CHIPS strategy, biphasic pulses were interleaved from two independent stimulation channels (from 1A to 2B, or from 2B to 1A) so that the anodic phases of each channel were delivered consecutively, followed by their respective charge-balancing phases after a 100 μs IPG. In this case, the pulse width for each channel was set to half of the pulse width used during single-channel stimulation. Both channels delivered identical pulses (with the same amplitude and duration), but stimulation from the second (trailing) channel was temporally shifted by the PW from the first (leading) channel to prevent pulse overlap. During some experiments, various delays (Del) were tested between the leading and trailing channels.

Performance for each of the stimulation configurations was assessed by comparing the percept threshold measurements and the results from the psychophysical evaluation of the elicited percepts. FIG. 2 summarizes the experimental protocols completed in the examples.

Percept thresholds were obtained from all subjects for each single-channel (1A, 2B) and multi-channel (3AB, 4BA) configuration under five different pulse width values (300 μs to 700 μs, at 100 μs intervals). These pulse widths were consistent with values used in the literature to activate sensory fibers in the human peripheral nerves [25]. Additional multi-channel stimulation trials were completed by a subset of subjects (n=4) under various trailing pulse delay values to assess how much later could the trailing pulse be delivered after the leading pulse without negating the temporal summation of the pulses. To assess the effects of small delays on the CHIPS performance, a set of short delays from 0 μs to 60 μs (20 μs intervals) was evaluated, while the effects of longer delays were evaluated using a delay of 200 μs, which is within the range of the leading pulse durations, and 500 μs, which is higher than the maximum leading pulse duration. The order of the stimulation configuration, pulse width and delays, was randomized across all subjects. All trials were completed twice under every condition. The percept threshold determination procedure used was a Dual Randomized Parameter Estimation by Sequential Testing (DR-PEST), which is a combination of the Parameter Estimation by Sequential Testing (PEST) method and a randomly alternating dual staircase method [26]. This combination was selected to reduce variability and subject bias, allowing for fast and accurate estimation of percept thresholds. Examples of two stimuli presentation sequences are shown in FIG. 3.

A custom algorithm was designed and integrated into a MATLAB® program that controlled the delivery of electrical stimuli and collected information about the subject's sensory responses. Subjects triggered the delivery of the stimuli by pressing the "Go" button, and then provided a positive or negative response by pressing the "Yes" or "No" button, depending on whether the stimulus was detected. Positive responses were followed by a decrease in pulse amplitude (PA) while negative responses were followed by an increase in PA. The step size was halved after every positive response or doubled after two successive negative responses. The direction of the trials was always changed after a response reversal. The order of occurrence of the staircases was randomized in advance. The two sequences always started apart and eventually came together, crossing and re-crossing each other thereafter until six response reversals per sequence were reached.

The subject responses were analyzed for each sequence independently since they could be considered as two replicates of the same condition. Threshold values were computed by fitting the Wichmann and Hill psychometric function [27] and finding the stimulation amplitude value with a 50% probability of having a positive or negative response for each sequence. The final threshold amplitude for a given pulse width was computed by taking the average of the thresholds found from each sequence. The experimental percept threshold measures (two repetitions per pulse width) were fitted to the Lapicque-Weiss's theoretical model [28, 29] to compute individual strength-duration (SD) curves for each subject under each stimulation configuration. The collected percept threshold data were used to determine the sensory activation performance of each configuration, where lower threshold values meant better performance.

For trials comparing the single-channel (1A, 2B) and novel multi-channel (3AB, 4BA) configurations, each subject's SD curves were normalized to the rheobase of configuration 1A, which was by definition the best-performing single-channel configuration (lowest overall threshold). This configuration was assumed to have been placed closer to the median nerve than "2B" and thus chosen as the comparison standard. Normalization was done in order to compare percept thresholds across participants while accounting for between-subject variability. To compare activation performance across configurations, the normalized threshold values for each tested PW were first scaled to the percentage (%) of the threshold from 1A on a per-PW basis, then pooled across all PWs. A theoretical "no summation" reference SD curve was calculated by assuming only half of the PW was delivered under configuration 1A. For trials comparing multi-channel stimulation under various trailing pulse delays, each subject's SD curves under each delay were normalized to the rheobase of the tested multi-channel configuration without any delay, and adjusted for PW. The configurations were assessed by comparing their normalized threshold measurements with a nonparametric one-way ANOVA (Kruskal-Wallis test, MATLAB® Statistics Toolbox 11.6). Multiple post-hoc comparisons between configurations were made using the Dunn-Sidak test at an alpha level of 0.05 for significance.

In order to evaluate the characteristics of sensations evoked by stimulation, subjects were instructed to complete a multiple-choice psychophysics questionnaire about the Modality, Quality, and Location (MQL) of the sensations under each configuration. This questionnaire was based on similar questionnaires used in other neurostimulation studies to provide sensory feedback.

While completing the questionnaire, subjects received 1 second long bursts (30 Hz, 100 µs IPG). For each configuration, the stimulation parameters were kept constant. Subjects were allowed to trigger the delivery of the short stimulation burst as needed to answer the questionnaire with confidence. Stimulation amplitude was set to 25% above the percept threshold (1.25×PT) at a pulse width of 500 µs. This duration was chosen because it allowed for a wide range of amplitudes to be used. A trailing pulse delay of 0 µs was used during multi-channel stimulation in this procedure. The order of the configuration used during this assessment was randomized across all subjects. There were short breaks in between each questionnaire to mitigate any possible effects of previous stimulation conditions on the subjects' responses.

The sensation modality was evaluated from a list of 16 pre-defined options (e.g., touch, pressure, needle prick, tingling, vibration, etc.). The sensation quality was evaluated as comfortable or uncomfortable, as well as sharp, blunt, soft, mild, or strong. The perceived location of the sensations was evaluated as local (at the stimulation site), spreading (from one site to another), or referred (in the hand). All options in the questionnaire were explained to the subjects before the experiment. Subjects were instructed to choose one or more options that best described the elicited sensation, or to report a different word if none of the options accurately described the sensation.

Subjects reported the percept location by drawing the localized region of the sensation on a paper form with printed outlines of the palmar and dorsal surfaces of the right hand. Subjects completed a percept map for each configuration, under the same stimulation parameters used during the MQL questionnaires. Each percept map was scanned and loaded into individual layers in Adobe® Photoshop® CS2 (Adobe, San Jose, Calif.). The percept regions were digitized by tracing a solid shade within the area drawn by the subjects with an Intuos Pro drawing tablet (Wacom Co., Ltd. Saitama, Japan). The same hand contour image provided to the subject was used as a base layer during the digitization process. All digitized percept areas from each configuration were stacked in MATLAB®, and overlapping pixels were aggregated to calculate the frequency of location reports for all subjects.

Surface electrodes had impedance values (mean±SD) of 26.4±0.5 kf across all subjects and remained stable throughout. No side effects like irritation or redness of the skin were observed in any of the subjects.

Example 1—Percept Thresholds

Strength-duration profiles obtained from the percept threshold measures of an individual subject under each stimulation configuration were normalized to the rheobase of configuration 1A, which was the best-performing (lowest value) single-channel configuration, as compared to configuration 2B. On average, the mean rheobase current±SD for 1A was approximately 695.7±277.5 µA across all subjects. More specifically, for seven subjects with mean age 25±5.5 years, the rheobase was approximately 570.1±173.5 µA, while three subjects with mean age 55.6±5.7 years had a rheobase of around 988.9±268.4 µA. FIG. 4A shows the mean SD curves across all participants, where the pulse durations correspond to the total duration (temporal summation) of pulses from each channel. Multi-channel stimulation with the CHIPS strategy according to embodiments (configurations 3AB and 4BA) resulted in percept threshold values comparable to single-channel stimulation (between configurations 1A and 2B), and far below the "no summation" (NS) reference (dashed-line) while delivering shorter pulses per channel.

The plots in FIGS. 4B and 4C compare the sensory activation performance of each configuration. Stimulation under configuration 1A resulted in significantly lower percept thresholds than configurations 2B (p=0.0020) and 3AB (p<0.001), while no significant differences were found between configurations 1A and 4BA, making 4BA the best-performing multi-channel configuration.

The sensory activation performance of multi-channel stimulation appeared to decrease with the introduction of delays between interleaved pulses, especially for relatively large delays (i.e., 500 μs). Referring to FIG. 4D, percept threshold values for both configurations 3AB and 4BA increased as delays were increased, suggesting an attenuation in the net charge delivery due to a reduction in temporal pulse summation. In general, both configurations appear to approach the "no summation" (NS) threshold levels (gray dashed line), with 3AB reaching it at around 500 μs.

Example 2—Elicited Percepts

Results from the MQL questionnaire about percept modality (FIG. 5A) show that all stimulation configurations evoked sensations that were mostly described as "tingling", with only a few reports of "needle prick". Only single-channel stimulation resulted in numb, unnatural, or painful sensations. In contrast, only multi-channel stimulation evoked sensations of vibration, pressure, or light touch. Referring to FIG. 5B, most subjects (n=9) reported comfortable sensations after multi-channel stimulation, while up to four participants reported them as uncomfortable after single-channel stimulation. Percept location responses in FIG. 5C show that most participants felt referred sensations for all configurations, while local sensations (under the electrodes) were only reported after single-channel stimulation (n=7).

Example 3—Percept Locations

All participants reported distally referred sensations across the area of the hand including the ring, index, middle fingers and the thumb. In general, percept regions reported under each single-channel configuration were not identical. Percept regions reported under the multi-channel configurations did not represent the spatial summations of percept regions from the single-channel configurations. Rather, they were often perceived as new percept regions that did not include the local sensations under the electrodes. Referring to FIGS. 6A and 6B, local sensation under the electrodes were reported by seven participants for both single-channel configurations only. Only one subject reported a tingle-like sensation on the lateral surface of the wrist (between electrodes, not under) with configuration 3AB (FIG. 6C). FIG. 6D shows that stimulation under configuration 4BA resulted in the most consistent reports of distally-referred sensations on the ring and middle fingers as well as the palm of the hand, without local sensations.

Example 4—Hybrid Computational Model

A simplified hybrid computational model of neural activation in the human wrist was developed and utilized to implement and characterize the CHIPS strategy according to embodiments of the subject invention. The model comprised two components: a 2D finite element model of the human wrist to compute extracellular potential fields; and a sensory axon model to compute neural responses to extracellular electrical stimulation. This approach provided the means to compare the relative activation of the sensory axons under different stimulation conditions, and to visualize the potential outcomes of implementing the novel CHIPS strategy with human subjects. The neural activation results from the computational effort were used to explore and narrow down the stimulation parameter space and to make informed decisions about electrode placement during stimulation fitting procedures. The electrode configurations and stimulation parameters were further refined during pilot experiments in human subjects to establish the experimental parameter sequences and electrode arrangements used during the final set of studies.

A finite element model (FEM) of the wrist was developed to predict extracellular potential changes due to stimulation from traditional single-channel stimulation and from stimulation using the CHIPS strategy according to embodiments. The model design included surface electrodes distributed around the ventral and dorsal surfaces and electrical properties for each tissue domain. The extracellular potential profiles were applied to a validated sensory axon model in NEURON (v7.3, [51]) to predict whether or not a sensory axon would fire at different locations (points of interest) within the wrist geometry. Several simulations were performed to assess the activation performance for different pulse durations and pulse delays to generate strength-duration profiles for each stimulation condition.

A simplified cross-section of the human wrist was assembled in a 2D drawing in SolidWorks (Dassault Systèmes SolidWorks Corporation, Waltham, Mass.) The geometry characteristics were based on published anthropometric data [52], and included the radius and ulna embedded within a 53 mm×41 mm oval-shaped muscle region, surrounded by a 2.5 mm fat layer and a 1 mm skin layer (see FIG. 7A). Two pairs of surface electrodes were distributed around the ventral and dorsal surfaces. Two small stimulating (s) electrodes were placed on the ventral aspect of the wrist while two large return (r) electrodes were placed on the opposite (dorsal) side. Stimulating electrodes were 15 mm long arcs separated by 1 mm each. These represented the cross-section of neighboring electrodes with a surface area of 275 square millimeters ($mm^2$). The return electrodes were 20 mm long arcs separated by 1 mm each. These represented the cross-section of neighboring electrodes with a surface area of 460 $mm^2$.

The drawing was exported as a segmented 2D geometry and imported into COMSOL Multiphysics (COMSOL AB, Stockholm, Sweden). Electrical conductivity and relative permittivity values were applied to each tissue layers (see Table 1) in order to compute the potential field distribution within the wrist generated by current-controlled stimulation by solving the Poisson's equation relating electric potential to source current density and the tissue electrical properties. In this simplified model, the skin and fat were assumed to be homogenous materials, and the different layers of the skin were combined and treated as one. Because this model only had one muscle component, it was assumed to be entirely longitudinal and transverse components were disregarded. Bone was assumed to be homogeneous and the properties for cortical bone were used [53]. Each stimulating electrode on the ventral surface was assigned to a return electrode on the dorsal surface such that each "s-r" pair would be an independent stimulation channel (source and sink, respectively) configured such that their current paths would cross each other. Time dependent simulations were performed using the COMSOL Electric Currents (EC) physics on a finely meshed geometry with a minimum element size of 18.9 micrometers (μm) and a maximum element size of 1000 μm (see FIG. 7B). These mesh characteristics were determined during convergence testing, ensuring that the calculations are consistent throughout the model. The EC module required a ground boundary condition to run the simulations. A ground point was placed within the ulna and radius in order to satisfy this requirement while using the poor conductivity of the bone to minimize the effect of the ground points on the stimulation currents.

Two stimulation configurations were simulated for different stimulation parameters (see FIG. 7C). During traditional single-channel (SC) stimulation, a 500 μs long current regulated square pulse was delivered across a single stimulation channel (configuration pattern 1A or 2B), with a pulse amplitude PA at the source, and −PA (negative PA) at the sink. For the multi-channel (MC) configurations used to test the CHIPS strategy, two 250 μs long current regulated square pulses were interleaved from two independent stimulation channels (from 1A to 2B, or from 2B to 1A) so that the pulses were delivered from each channel consecutively, resulting in a total pulse duration of 500 μs. The extracellular potential distributions were calculated for each configuration and exported to MATLAB R2019b (Mathworks, Natick Mass.) with a 0.1 mm grid resolution.

TABLE 1

| Electrical Properties of Tissues (Gabriel, 1996) | | |
|---|---|---|
| | Electrical (σ) | Relative (ε) |
| S | 0.013 S/m | 990.8 |
| F | 0.044 S/m | 50.8 |
| M | 0.50 S/m | 1836.4 |
| B | 0.024 S/m | 144.5 |

The axon fiber model used was based on a previously published sensory axon model [30], derived from the McIntyre Richardson Grill (MRG) model [55] and implemented in a NEURON programming environment [51]. The sensory axon model was a double-cable model including nodes separated by internodal segments coated in myelin. Each internode was divided into ten segments: two paranodal myelin attachment segments (MYSA); two paranodal main segments (FLUT); and six internodal segments (STIN). The sensory axon parameters used are the same as described in the published model [30], with ion channels modeled as voltage dependent resistors, including fast K+, slow K+, and hyperpolarization-activated cyclic-nucleotide gated (HCN) channels, with leak resistance and internodal capacitance within the internodal segments. Each node has fast K+, slow K+, fast Na+, persistent Na+, and leak channels, with nodal capacitance. For these simplified neuron response simulations, a single sensory axon (12 μm diameter, 21 nodes, and 20 internodes) was used.

The calculated extracellular potential distribution over the stimulation time was used to generate a spatiotemporal matrix of voltages at five different points of interest (POI) within the wrist cross-section (see FIG. 7C). The voltage levels were also determined for each segment along the length of each sensory axon. These voltage profiles were applied to the model to determine its activation threshold at each POI. An activation region (AR) was derived to indicate regions within the cross-section that had voltage values which would be sufficient to activate our model sensory axon. The AR was determined for each configuration from the 2D activation distribution that resulted in activation of a single sensory axon located at each POI. The boundary of an AR represents the farthest point from the stimulation source that is above the sensory axon threshold. Performance for each of the stimulation configurations was assessed by comparing the lowest stimulation amplitudes required to generate an AR with a boundary that overlaps with a sensory axon located at each of the five POIs near the stimulating electrodes. The activation thresholds were obtained for each configuration under five different pulse width values (300 μs to 700 μs, at 100 μs intervals) to compute their strength-duration (SD) curves. Additional simulations of the CHIPS configurations were performed to assess the attenuating effect of various trailing pulse delays (0 μs-100 μs in 20 μs intervals, 0.2 ms, 0.5 ms, and 1 ms) on the activation thresholds for a sensory axon located at POI 2.

Activation regions (AR) were obtained to spatially describe where the axons were likely to be activated within the cross-section of the wrist. FIG. 8A depicts the regions of activation generated by each configuration when triggering a sensory axon located closer to A than B (POI 2 in FIG. 7C) with 500 μs long stimulation pulses (250 μs for each channel with CHIPS). This POI was chosen to simulate a condition in which one channel is better positioned to activate the sensory axon than the other. The AR under single-channel configuration 2B was found to be larger than 1A, as the stimulation source is farther from the point of interest. Stimulation under both multi-channel configurations with the CHIPS strategy according to embodiments (3AB and 4BA) resulted in activation regions with boundaries that overlapped with the sensory fiber at the point of interest, while delivering current amplitudes comparable to single-channel stimulation and only half of the pulse width from each of the stimulation channels.

Activation threshold values were computed for 500 μs long stimulation pulses (250 μs for each channel with CHIPS) across five POIs representing different possible locations for the median nerve (see FIG. 8B). The stimulation amplitudes required to activate a sensory axon under single-channel stimulation increased as the distance between the stimulation source and the POI increased. However, the activation performance of the CHIPS strategy according to embodiments was found to be relatively stable for the different points of interest tested. More detailed activation threshold computations were performed for multiple pulse durations to obtain the strength-duration (SD) profiles for each simulated configuration when activating a sensory axon located at the second POI. At this location, multi-channel stimulation with the CHIPS strategy according to embodiments (configurations 3AB and 4BA) resulted in threshold values comparable to single-channel stimulation (between configurations 1A and 2B), while delivering shorter pulses per channel (see FIG. 8C).

Activation thresholds were also obtained for both multi-channel configurations when triggering a sensory axon located at POI 2, with 500 μs long stimulation pulses (250 μs for each channel) under various trailing pulse delays. The activation performance of multi-channel stimulation appeared to decrease with the introduction of delays between interleaved pulses. Referring to FIG. 8E, percept threshold values for both configurations 3AB and 4BA increased gradually as delays were increased. Activation thresholds stop increasing as the temporal summation of the pulses appears to be fully attenuated as delay values approach 0.5 ms (dashed vertical line).

The computational study yielded strength-duration profiles and activation thresholds that were in general confirmed by the studies in human subjects (see Examples 1-3). The computational study predicted activation thresholds for multi-channel stimulation in between those found under single-channel stimulation when the target nerve is somewhere between the current paths of the two stimulating electrodes (FIGS. 8A-8E). It also predicted that implementation of the CHIPS strategy according to embodiments would result in activation areas that were smaller than the combined activation areas produced by each independent channel (FIG. 8A), suggesting that the CHIPS strategy could result in more focal activation than single-channel stimulation. Without being bound by theory, the introduction of delays between interleaved pulses seem to attenuate the effect of the leading pulse on the sensory axon at the time of arrival of the trailing pulse, resulting in increased percept thresholds (FIG. 8E). Delays resulted in a gradual threshold increase over the delay values tested, plateauing near the threshold level expected for a "no summation" scenario. This was also confirmed by Examples 1-3.

The main building blocks of the simplified wrist cross-section geometric structure used in the hybrid model included structures and parameters that have the largest influence on the potential distribution and neural activation, while those with a small influence were neglected or approximated as simpler or lumped structures. The model incorporated two homogeneous bony structures (ulna and radius), a large longitudinal muscle structure, and homogeneous fat and skin layers. While the electrical properties of the skin and fat layers have been shown to have little influence on nerve activation when using current-controlled stimulation, the electrical properties of muscle, as well as the location and diameter of the sensory axon do have a major influence. The influence of the sensory axon location implies that the thickness of the skin and fat layers seen in humans is a critical factor for predicting neural activation. Other tissues and inhomogeneities that are not included can affect the voltage distribution. For instance, blood vessels or interstitial fluids have low resistivity and could act as shunts, while tendons that connect muscles to bony structures have high resistivity. The close vicinity of these tissues to nerves may also have an influence on nerve activation during surface stimulation. Additionally, the FEM model of surface stimulation used time dependent simulations in an effort to include the effect of tissue capacitance which is known to affect the shape and amplitude of the stimulation pulses within the tissue. However, the model neglects the properties of electrode-skin interface components such as the hydrogel layer, which could have major effects on the potential distribution due to its capacitance. The specific contribution of the capacitive properties of this layer in this model needs further investigation.

Also, the nerve trunk was not included in the FEM model, and the neural response simulations only involved a single sensory axon at each point of interest. Because the axon was tested at many different locations, including the nerve tissue would have required solving several versions of the FEM model for every nerve location tested. Because the purpose of the model was to compare the performance of the different configurations, it was expected that the nerve tissue would have little impact on the differences in extracellular potential distribution from each configuration. Thus, simulation time was considerably reduced by not including the properties of the nerve tissue. The model could be further enhanced to investigate the effect of the different configurations and scheduling strategies on axonal population recruitment to determine whole nerve activation profiles under each condition. This could be done by including the nerve tissue at a fixed location in the FEM model, and expanding the NEURON model to include multiple fascicles within the median nerve, with each fascicle containing a realistic distribution of sensory axons with a random assignment of axon diameters following known axonal population proportions. Still further expansions could include the somatotopic targets such as the hand digits and palm. This would allow for the computational evaluation of activation region steering strategies with an electrode array.

While the hybrid model could be optimized to include additional tissue properties and simulate more realistic conditions, the overall effects of the missing structures on the extracellular potential distribution was expected to be the same for all stimulation configurations and sensory axons at the different points of interest. Therefore, the simulation results were used to compare the relative activation of the sensory axons based on their location and stimulation approach used, and to visualize the potential performance differences expected after implementation of these stimulation strategies in human subjects. The behaviors observed in the hybrid model thus served as the basis for designing the stimulation protocols used during human studies (Examples 1-3) and developing more streamlined fitting strategies. For example, simulation results showed lower activation thresholds for both independent channels when the sensory axon was located between both channels (FIG. 8B). This information can be used to guide selection of electrode pairs in an array in order to optimize the shape of the activation region. For instance, choosing the electrode pairs with the lowest single-channel thresholds assures that the target nerve would be in between the two stimulating electrodes when stimulating with the CHIPS strategy according to embodiments, thus avoiding unnecessarily larger activation regions for either of the channels. The model could also be used to guide the development of stimulation fitting algorithms that would allow for real-time adjustment of stimulation parameters such as stimulation amplitude and combination of electrodes within an array to achieve targeted activation of different parts of the nerve and steer the location of the evoked sensations. By making the appropriate adjustments, the model could potentially be used to explore different stimulation methods and predict neural activation responses when using cuff-like electrodes or delivering intraneural stimulation to target both sensory or motor axons.

Surface electrical neurostimulation (SENS) is a potential non-invasive alternative for providing somatotopically-matched sensory feedback according to embodiments of the subject invention. In this approach, surface electrodes applied on the skin are used to deliver transcutaneous electrical pulses to nearby peripheral nerves, activating afferent pathways. Earlier studies have shown that single-channel SENS can be used to elicit distally referred sensations when targeting the median and ulnar nerves at the forearm or at the elbow level. However, traditional methods for single-channel stimulation are hampered by inadequate electrode fitting, poor selectivity, motion dependency, and localized discomfort associated with large charge densities.

An enhanced surface electrical neurostimulation (eSENS) platform has been developed to overcome these drawbacks through the implementation of a Channel-hopping Interleaved Pulse Scheduling (CHIPS) strategy. CHIPS is a novel multi-channel approach designed to deliver interleaved current pulses from independent stimulation channels, hopping across multiple strategically distributed surface electrodes. By leveraging the combined influence of the interleaved current pulses, each independent channel can be set to stimulate at shorter pulse widths than single-channel stimulation, thus reducing the total charge per pulse delivered by any given electrode, while maintaining net charge delivery to the target nerve at functional levels. In other words, the stimulation is sub-threshold for cutaneous activation near each electrode, but supra-threshold at the level of the nerve due to the spatiotemporal summation of the interleaved pulses.

The CHIPS strategy in accordance with the subject invention was first developed and characterized in silico, where the sensory activation performance of this novel pulse scheduling scheme was evaluated using a computational model before implementation within the stimulation platform. Human studies were then performed to evaluate the performance of the CHIPS strategy and to determine whether this novel multi-channel approach could evoke distally referred sensations more efficiently and comfortably than single-channel stimulation. Able-bodied subjects received stimulation from either one-electrode pair at a time (single-channel) or interleaved between two-electrode pairs (multi-channel) placed around their right wrist. Percept thresholds were characterized for various pulse widths under each configuration, where the total duration was divided amongst the two active channels during multi-channel stimulation. We performed additional multi-channel stimulation threshold trials in which various delay values were introduced between the interleaved pulses to determine whether delays attenuate pulse summation and affect sensory activation performance. A psychophysical questionnaire was used to interrogate the perceived modality, quality and location (MQL) of the evoked sensations under each configuration. Summation of interleaved current pulses delivered from multiple, strategically distributed surface electrodes can result in selective activation of afferent pathways while avoiding the local sensations and skin discomfort associated with the large charge densities from traditional single-channel stimulation. The inventors have shown that the CHIPS strategy according to embodiments of the subject invention can evoke stronger, more comfortable, distally-referred sensations without local sensations in able-bodied subjects, maintaining activation thresholds comparable to single-channel stimulation, while delivering shorter pulses per channel. This novel strategy has the potential to address some of the issues that have precluded wide adoption of surface stimulation as a viable alternative for intuitive, somatotopically-matched sensory feedback.

Example 5—Computational Evaluation of the CHIPS Strategy

A finite element model (FEM) of the wrist was developed to predict extracellular potential changes due to stimulation from traditional single-channel stimulation and from stimulation using the CHIPS strategy according to embodiments. The model design included surface electrodes distributed around the ventral and dorsal surfaces and electrical properties for each tissue domain. The extracellular potential profiles were applied to a validated sensory axon model in NEURON (v7.3, (Hines and Carnevale, 1997)) to predict whether or not a sensory axon would fire at different locations within the wrist geometry. Several simulations were performed to assess the activation performance for different pulse durations and pulse delays to generate strength-duration profiles for each stimulation condition.

A simplified cross-section of the human wrist was assembled in a 2D drawing in SolidWorks to analyze potential field computation via a wrist FEM model. The geometry characteristics were based on published anthropometric data (and included the radius and ulna embedded within a 53 mm×41 mm oval-shaped muscle region, surrounded by a 2.5 mm fat layer and a 1 mm skin layer (FIG. 7A). Two pairs of surface electrodes were distributed around the ventral and dorsal surfaces. Two small stimulating (s) electrodes were placed on the ventral aspect of the wrist while two large return (r) electrodes were placed on the opposite (dorsal) side. Stimulating electrodes were 15 mm long arcs separated by 1 mm each. These represented the cross-section of neighboring electrodes with a surface area of 275 $mm^2$. The return electrodes were 20 mm long arcs separated by 1 mm each. These represented the cross-section of neighboring electrodes with a surface area of 460 $mm^2$.

The drawing was exported as a segmented 2D geometry and imported into COMSOL Multiphysics (COMSOL AB, Stockholm, Sweden). Electrical conductivity and relative permittivity values were applied to each tissue layer (Table 1) in order to compute the potential field distribution within the wrist generated by current-controlled stimulation by solving the Poisson's equation relating electric potential to source current density and the tissue electrical properties. In this simplified model, the skin and fat were assumed to be homogenous materials, and the different layers of the skin were combined and treated as one. Since this model only had one muscle component, it was assumed to be entirely longitudinal and transverse components were disregarded. Bone was assumed to be homogeneous and the properties for cortical bone were used. Each stimulating electrode on the ventral surface was assigned to a return electrode on the dorsal surface such that each "s-r" pair would be an independent stimulation channel (source and sink, respectively) configured such that their current paths would cross each other. Time dependent simulations were performed using the COMSOL Electric Currents (EC) physics on a finely meshed geometry with a minimum element size of 18.9 µm and a maximum element size of 1000 µm (FIG. 7B). These mesh characteristics were determined during convergence testing, ensuring that the calculations are consistent throughout the model. The EC module required a ground boundary condition to run the simulations. A ground point was placed within the ulna and radius in order to satisfy this requirement while using the poor conductivity of the bone to minimize the effect of the ground points on the stimulation currents.

Two stimulation configurations were simulated for different stimulation parameters (FIG. 7C). During traditional single-channel (SC) stimulation, a 500 µs long current regulated square pulse was delivered across a single stimulation channel (configuration pattern 1A or 2B), with a pulse amplitude PA at the source, and −PA at the sink. For the multi-channel (MC) configurations used to test the CHIPS strategy, two 250 µs long current regulated square pulses were interleaved from two independent stimulation channels (from 1A to 2B, or from 2B to 1A) so that the pulses were delivered from each channel consecutively, resulting in a total pulse duration of 500 µs. The extracellular potential distributions were calculated for each configuration and exported to MATLAB R2019b (Mathworks, Natick Mass.) with a 0.1 mm grid resolution.

The Neuron Response Computation (Sensory Axon Model) axon fiber model used in this study was based on a previously published sensory axon model (Gaines et al., 2018), derived from the McIntyre Richardson Grill (MRG) model (McIntyre et al., 2002) and implemented in a NEURON programming environment (Hines et al., 1997). The sensory axon model was a double-cable model consisting of nodes separated by internodal segments coated in myelin (FIGS. 9A-9B). Each internode was divided into ten segments: two paranodal myelin attachment segments (MYSA); two paranodal main segments (FLUT); and six internodal segments (STIN). The sensory axon parameters used are the same as described in the published model with ion channels modeled as voltage dependent resistors, including fast $K^+$, slow $K^+$ and hyperpolarization-activated cyclic-nucleotide gated (HCN) channels, with leak resistance and internodal capacitance within the internodal segments. Each node has fast $K^+$, slow $K^+$ fast $Na^+$, persistent $Na^+$, and leak channels, with nodal capacitance. For these simplified neuron response simulations, a single sensory axon (12 μm diameter, 21 nodes and 20 internodes) was used.

The calculated extracellular potential distribution over the stimulation time was used to generate a spatiotemporal matrix of voltages at 5 different points of interest (POI) within the wrist cross-section (FIG. 7C), depending on the distance between the stimulation source and the point of interest. These voltages were applied along the length of the sensory axon to determine its activation threshold at each POI. An activation region (AR) was derived to spatially describe where the axons are likely to be activated within the cross-section of the wrist. The AR was determined for each configuration from the 2D activation distribution that resulted in activation of a single sensory axon located each POI. The boundary of an AR represents the farthest point from the stimulation source that is above the sensory axon threshold. Performance for each of the stimulation configurations was assessed by comparing the stimulation amplitudes required to activate a sensory axon located at each of the 5 POIs near the stimulating electrodes. The activation thresholds were obtained for each configuration under 5 different pulse width values (300 μs to 700 μs, at 100 μs intervals) to compute their strength-duration (SD) curves.

Example 6—Non-Invasive Stimulation Applied to Able-Bodied Subjects

Written informed consent was obtained from 10 adult subjects (4 males, 6 females, mean age±SD: 34.9±15.3) in compliance with the Institutional Review Board of Florida International University which approved this study protocol. All prospective subjects were screened prior to the study to determine eligibility. Subjects were able-bodied, with no sensory disorders or any self-reported condition listed as a contraindication for surface stimulation (pregnancy, epilepsy, lymphedema, or cardiac pacemaker).

Subjects were seated on a chair with both arms on a table in front of them (FIG. 1A). Their right forearm was thoroughly cleaned with an alcohol wipe and placed on a support pad on the table, with their right hand's palmar surface parallel to the vertical plane. Subjects were encouraged to drink water before and during the experiment to increase skin hydration.

Each subject received electrical stimulation from a distributed set of surface electrodes around their right wrist to activate their median nerve sensory fibers, evoking distally referred sensations in their right hand. Median nerve stimulation was delivered by four self-adhesive hydrogel electrodes (Rhythmlink International LLC, Columbia, S.C.) placed around the subject's right wrist, allowing superficial access to the median nerve's sensory fibers from the index, middle, and part of the ring finger. Two small stimulating (s) electrodes (15×20 mm) were placed on the ventral aspect of the wrist (~3 cm from the distal radial crease) and two large return (r) electrodes (20×25 mm) on the opposite (dorsal) side (FIG. 1). Each "s-r" electrode pair was assigned to an independent channel and configured such that their current paths would cross each other and intersect the median nerve transversally (FIG. 1). Placement of each "s-r" pair was determined by exploring various locations around the median nerve while providing brief, is long stimulation bursts (500 μs biphasic, anode-first pulses at 30 Hz) at various amplitude levels between 1.5 mA and 3 mA, in increments of 0.1 mA, until a distinct referred sensation was reported by the subject.

A custom 3-button keyboard was placed on the table in front of the subject's left hand. Subjects used this keyboard to trigger the delivery of the electrical stimuli (Go) and provide percept responses (Yes/No). Subjects were fitted with a pair of noise cancelling headphones playing soft white noise to reduce distracting noises and deliver sound queues at various stages of the study. Subjects were instructed to relax and maintain a fixed arm position throughout the experiment but were encouraged to stretch and move their hand during periodic breaks to prevent discomfort. Subjects were asked about their comfort levels, or if additional breaks were needed after each task.

A multi-channel programmable, optically isolated benchtop bio-stimulator (TDT IZ2-16H, Tucker-Davis Technologies, Alachua Fla. USA) was used to deliver the electrical stimuli. A custom TDT Synapse stimulation control environment running on the TDT RZ5D base processor was used to schedule charge-balanced, current-controlled biphasic rectangular pulses with pulse amplitudes (PA) between ±3 mA per channel, with 1 μA/step resolution, and a pulse width (PW) resolution of 21 μs/step. Anode-first pulses were used throughout the study, as they have been shown to activate orthogonally oriented fibers more efficiently than cathode-first pulses (Sato and Tachi, 2010, Anderson et al., 2019). The TDT Synapse environment was interfaced to a custom MATLAB program (v2018b, MathWorks Inc, Natick, Mass.) designed to run and monitor the various study conditions and modulate the stimulation parameters based on subject responses.

Two stimulation configurations were used in this study (FIG. 1). During traditional single-channel (SC) stimulation, biphasic current pulses with a 100 μs inter-phase gap (IPG) and a given PW were delivered to the median nerve from only one channel at a time (configuration pattern 1A or 2B). For the multi-channel (MC) configurations used to test the CHIPS strategy, biphasic pulses were interleaved from two independent stimulation channels (from 1A to 2B, or from 2B to 1A) so that the anodic phases of each channel were delivered consecutively, followed by their respective charge-balancing phases after a 100 μs IPG. In this case, the pulse width for each channel was set to half of the pulse width used during single-channel stimulation. The pulses were interleaved to prevent channel interactions. During some experiments, various delays (Del) were tested between the first (leading) channel and the second (trailing) channel.

Performance for each of the stimulation configurations was assessed by comparing the percept threshold measurements and the results from the psychophysical evaluation of the elicited percepts. FIG. 2 summarizes the experimental protocols completed in this study.

Percept thresholds (PT) were obtained from all subjects for each SC (1A, 2B) and MC (3AB, 4BA) configuration under 5 different pulse width values (300 μs to 700 μs, at 100 μs intervals). Additional MC stimulation trials were completed by a subset of subjects (n=4) under various interleaved pulse delay values (0 μs, 20 μs, 40 μs, 60 μs, 200 μs, 500 μs). The order of the stimulation configuration, pulse width and delays was randomized across all subjects. All trials were completed twice under every condition. The PT determination procedure used was a combination of the Parameter Estimation by Sequential Testing (PEST) method (Taylor and Creelman, 1967) and a randomly alternating dual staircase method (Cornsweet, 1962). This combination was meant to reduce variability and user bias, allowing for fast and accurate estimation of percept thresholds. An example of a stimuli presentation sequence is shown in FIG. 3. A custom algorithm was designed and integrated into a MATLAB program that controlled the delivery of electrical stimuli and collected information about the subject's sensory responses. Subjects triggered the delivery of the stimuli by pressing the "Go" button on a keyboard, and then provided a positive or negative response by pressing the "Yes" or "No" button, depending on whether each stimulus was detected. Positive responses were followed by a decrease in PA while negative responses were followed by an increase in PA. The step size was halved after every positive response or doubled after two successive negative responses. The direction of the trials was always changed after a response reversal. The order of occurrence of the staircases was randomized in advance. The two sequences always started apart and eventually came together, crossing and re-crossing each other thereafter until 6 response reversals per sequence were reached.

The subject responses were analyzed for each sequence independently since they could be considered as two replicates of the same condition. Threshold values were computed by fitting the Wichmann and Hill psychometric function (Wichmann and Hill, 2001) and finding the stimulation amplitude value with a 50% probability of having a positive or negative response for each sequence. The final threshold amplitude for a given pulse width was computed by taking the average of the thresholds found from each sequence. The experimental PT measures (2 reps per pulse width) were fitted to the Lapicque-Weiss's theoretical model (Lapicque, 1909, Weiss, 1990) to compute individual strength-duration (SD) curves for each subject under each stimulation configuration.

For trials comparing the traditional single-channel (1A, 2B) and novel multi-channel (3AB, 4BA) configurations, each subject's SD curves were normalized to the rheobase (Weiss, 1990) of the best performing SC configuration (with the lowest overall threshold). To compare across configurations, the normalized threshold values for each tested pulse width were scaled to the % of the threshold from the best performing SC configuration. A theoretical "no summation" reference SD curve was calculated by assuming only half of the PW was delivered under the best performing SC configuration. For trials comparing MC stimulation under various interleaved pulse delays, each subject's SD curves under each delay were normalized to the rheobase of the tested MC configuration without any delay, and adjusted for PW. Furthermore, the performance of each of the configurations was assessed by comparing their effect on the normalized threshold measurements with a one-way ANOVA (SPSS 21, IBM, Armonk, N.Y.). Post-hoc multiple comparisons between configurations were made using the Tukey-Kramer test at an alpha level of 0.05 for significance.

To evaluate the characteristics of the sensations evoked by the stimulation and to assess elicited percepts, subjects were instructed to complete a multiple-choice psychophysics questionnaire (Q1-Q3 in FIG. 10) about the Modality, Quality, and Location (MQL) of the sensations under each configuration. The order of the configuration used during this assessment was randomized across all subjects.

While completing the questionnaire, subjects received 1 sec long bursts (30 Hz, 100 µs IPG) under each configuration tested. Subjects were allowed to trigger the stimulation burst as many times as they needed to answer all the questions. Stimulation amplitude was set to 25% above the percept threshold (1.25×PT) at a pulse width of 500 µs. This duration was chosen since it allowed for a wide range of amplitudes to be used. No pulse delays were used during multi-channel stimulation in this procedure.

The sensation modality was evaluated from a list of 16 pre-defined options (i.e. touch, pressure, needle prick, tingling, vibration, etc). The sensation quality was evaluated as comfortable or uncomfortable, as well as sharp, blunt, soft, mild or strong. The perceived location of the sensations was evaluated as local (at the stimulation site), spreading (from one site to another), or referred (in the hand). All options in the questionnaire were explained to the subjects before the experiment. Subjects were instructed to choose one or more options that best described the elicited sensation, or to report a different word if none of the options accurately described the sensation.

The subject reported the percept location by drawing the localized region of the sensation on standardized paper diagrams of the palmar and dorsal surfaces of the right hand (Q4 in FIG. 10). The subject completed a percept map for each configuration, under the same stimulation parameters used during the MQL questionnaires. Each percept map was scanned and loaded into individual layers in Adobe Photoshop CS2. The percept regions were digitized by tracing a solid shade within the area drawn by the subject with an Intuos Pro drawing tablet (Wacom Co., Ltd. Saitama, Japan). The same hand contour image provided to the subject was used as a base layer during the digitization process. All digitized percept areas from each configuration were stacked in MATLAB, and overlapping pixels were aggregated to calculate the frequency of location reports for all subjects.

A finite element model of the wrist was developed and used to predict extracellular potentials due to stimulation from the CHIPS strategy and traditional single-channel stimulation. These voltage distributions were applied to a validated sensory axon model in NEURON to determine activation of a sensory axon located at different points of interest that represented possible locations of the median nerve within the wrist cross-section.

Activation regions (AR) were obtained to spatially describe where the axons were likely to be activated within the cross-section of the wrist. FIG. 8A depicts the regions of activation generated by each configuration when triggering a sensory axon located closer to A than B (POI 2 in FIG. 7C) with 500 µs long stimulation pulses (250 µs for each channel with CHIPS). This point of interest was chosen to simulate a condition in which one channel is better positioned to activate the sensory axon than the other. The AR under single-channel configuration 2B was found to be larger than 1A, as the stimulation source is farther from the point of interest.

Stimulation under both multi-channel configurations with the CHIPS strategy according to embodiments (3AB and 4BA) resulted in activation regions that reach the sensory fiber at the point of interest while delivering current amplitudes comparable to single channel stimulation and only half of the pulse width from each of the stimulation channels.

Activation threshold values were computed for 500 µs long stimulation pulses (250 µs for each channel with CHIPS) across 5 POIs representing different possible locations for the median nerve (FIG. 8B). The stimulation amplitudes required to activate a sensory axon under single-channel stimulation increased as the distance between the stimulation source and the point of interest increased. However, the activation performance of the CHIPS strategy was found to be relatively stable for the different points of interest tested. More detailed activation threshold computations were performed for multiple pulse durations to obtain the strength-duration (SD) profiles for each simulated configuration when activating a sensory axon located at the second POI. At this location, multi-channel stimulation with the CHIPS strategy according to embodiments (configurations 3AB and 4BA) resulted in PT values comparable to single-channel stimulation (between configurations 1A and 2B), while delivering shorter pulses per channel (FIG. 8C).

Able-bodied subjects received electrical stimulation from a distributed set of surface electrodes around their right wrist, evoking distally referred sensations in the general area innervated by the sensory fibers in the median nerve (palmar surface, index, middle, and part of the ring finger). The sensory activation performance and elicited percept characteristics were evaluated and compared for all configurations tested. All surface electrodes had impedance values (mean±SD) of around 26.4±0.5 kΩ, which remained stable for all subjects throughout the study (FIG. 11). No side effects like irritation or redness of the skin were observed in any of the subjects.

Strength-duration profiles obtained from the percept threshold (PT) measures of an individual subject under each stimulation configuration were normalized to the rheobase of configuration 1A, which was the best performing (lowest PT) single-channel configuration, as compared to configuration 2B. FIG. 4A shows the mean SD curves across all participants, where multi-channel stimulation with the CHIPS strategy according to embodiments (configurations 3AB and 4BA) resulted in PT values comparable to single-channel stimulation (between configurations 1A and 2B), and far below the "no summation" (N-S) reference (dashed-line) while delivering shorter pulses per channel.

FIG. 4B compares the sensory activation performance of each configuration. Stimulation under configuration 1A resulted in significantly lower PT's than configurations 2B ($p<0.005$) and 3AB ($p<0.05$), while no significant differences were found between configurations 1A and 4BA, making 4BA the best-performing multi-channel configuration.

The sensory activation performance of multi-channel stimulation appeared to decrease with the introduction of delays between interleaved pulses, especially for large delays (i.e. 500 μs). As shown in FIG. 4D, PT values for both configurations 3AB and 4BA increased as delays were increased, suggesting an attenuation in the net charge delivery due to a reduction in pulse summation.

Results from the MQL questionnaire about percept modality of elicited percepts (FIG. 16A) show that all stimulation configurations evoked sensations that were mostly described as "Tingling", with only a few reports of "needle prick". Only SC stimulation resulted in numb, unnatural or painful sensations. In contrast, only MC stimulation evoked sensations of vibration, pressure or light touch. As shown in FIG. 16B, most subjects (n=9) reported comfortable sensations after MC stimulation, while three participants reported them as uncomfortable after SC. Percept location responses in FIG. 16C show that most participants felt referred sensations for all configurations, while local sensations (under the electrodes) were only reported after SC stimulation (n=7).

All participants reported percept location as distally referred sensations across the area of the hand including the ring, index, middle fingers and the thumb. As shown in FIGS. 17A-17B, local sensation under the electrodes were reported by seven participants for both SC configurations only. Only one subject reported a tingle-like sensation on the lateral surface of the wrist (between electrodes, not under) with configuration 3AB (FIG. 17C). Finally, FIG. 17D shows that stimulation under configuration 4BA resulted in the most consistent reports of distally-referred sensations on the ring and middle fingers as well as the palm of the hand, without local sensations.

The preceding paragraphs present an evaluation of the performance of a novel Channel-hopping Interleaved Pulse Scheduling (CHIPS) strategy for multi-channel surface stimulation to determine whether it could evoke distally referred sensations more efficiently and comfortably than single-channel stimulation. Able-bodied subjects received interleaved current pulses from surface electrodes strategically distributed around their right wrist, resulting in more comfortable, distally-referred tingle-like sensations in the areas of the hand that are innervated by the sensory fibers in the median nerve, with lower incidence of local sensations than single-channel stimulation. These results show that the CHIPS strategy according to embodiments is capable of enhancing the performance of surface electrical stimulation for delivering non-invasive sensory feedback.

One of the challenges of traditional surface electrical stimulation studies is obtaining consistent and reliable responses due to differences in electrode placement within and across subjects, skin movement, position dependency and physiological variables that effect the electrical properties of the tissue. Computational modeling can be used to avoid some of these challenges during the research and development phases to predict neural activation performance under different stimulation conditions before implementation in clinical applications. Before the CHIPS strategy according to embodiments was implemented and tested with able-bodied subjects, a simplified hybrid computational model of neural activation within the human wrist was used to first predict extracellular voltage distributions in a simplified 2D anatomically-based finite element model, and axon activation within the human wrist due to surface stimulation using different electrode configurations and pulse scheduling strategies. Implementation of this model resulted in strength-duration profiles and activation thresholds comparable to experimental results with human subjects. The model predicted activation thresholds for multi-channel stimulation in between those found under single-channel stimulation when the target nerve is somewhere between the current paths of the two stimulating electrodes (e.g., as shown for POI-2 in FIG. 8A). The model also predicted that implementation of the CHIPS strategy would result in activation areas that were smaller than the combined activation areas produced by each independent channel (as shown in the solid-line shaded area in FIG. 8A), suggesting that the CHIPS strategy according to embodiments could result in more focal activation than single-channel stimulation.

The main building blocks of this simplified wrist cross-section geometric structure used in this model include structures and parameters that have the largest influence on the potential distribution and neural activation, while those with a small influence were neglected or approximated as simpler or lumped structures. As with any computational model, it may be helpful to understand the underlying assumptions and potential limitations inherent in the model design. This model incorporates two homogeneous cortical bony structures (ulna and radius), a large longitudinal muscle structure, and homogeneous fat and skin layers. While the electrical properties of the skin and fat layers have been shown to have little influence on nerve activation when using current-controlled stimulation, the electrical properties of muscle, as well as the location and diameter of the sensory axon do have a major influence. The influence of the sensory axon location implies that the thickness of the skin and fat layers seen in humans is a critical factor for predicting neural activation. Other tissues and inhomogeneities not included in this model can affect the voltage distribution. For instance, blood vessels or interstitial fluids have low resistivity and could act as shunts, while tendons that connect muscles to bony structures have high resistivity. The close vicinity of these tissues to nerves may also have an influence on nerve activation during surface stimulation. Additionally, the FEM model of surface stimulation used time dependent simulations in an effort to include the effect of tissue capacitance which is known to affect the shape and amplitude of the stimulation pulses within the tissue. However, this model neglects the properties of electrode-skin interface components such as the hydrogel layer, which could have major effects on the potential distribution due to its capacitance.

Another limitation of this model is that the neural response simulations only involved a single sensory axon at each point of interest. This was done to reduce simulation time. More complex simulations could be performed and are contemplated within the scope of the subject invention to further inform the effect of the different configurations and scheduling strategies on axonal population recruitment to determine whole nerve activation profiles under each condition. Embodiments provide expansion of the NEURON model to include multiple fascicles within the median nerve, with each fascicle containing a distribution of sensory axons with a random assignment of axon diameters following known axonal population proportions. Embodiments include the somatotopic targets such as the hand digits and palm, providing computational evaluation of activation region steering strategies with an electrode array.

While the model used in this study could be optimized to simulate more realistic conditions, the overall effects of these limitations on the extracellular potential distribution should be the same for all stimulation configurations and sensory axons at the different points of interest. Therefore, the analysis and conclusions drawn about the relative activation of the sensory axon based on its location and approach used should provide some information about how the different stimulation configurations and pulse scheduling strategies would perform under those specific conditions. The behaviors observed in this model served as the basis for designing the stimulation protocols used during human studies and developing more streamlined fitting strategies. For example, simulation results showed lower activation thresholds for both independent channels when the sensory axon was located between both channels (FIG. 8B). This information can be used to guide selection of electrode pairs in an array in order to optimize the shape of the activation region. For instance, choosing the electrode pairs with the lowest single-channel thresholds assures that the target nerve would be in between the two stimulating electrodes when stimulating with the CHIPS strategy according to embodiments, thus avoiding unnecessarily larger activation regions for either of the channels. This model may also be used according to embodiments, to guide the development of stimulation fitting algorithms that would allow for real-time adjustment of stimulation parameters such as stimulation amplitude and combination of electrodes within an array to achieve targeted activation of different parts of the nerve and steer the location of the evoked sensations. By providing the appropriate adjustments, embodiments may explore different stimulation methods and predict neural activation responses when using cuff-like electrodes or delivering intraneural stimulation to target both sensory or motor axons.

Sensory activation performance in humans was observed as multi-channel stimulation with the CHIPS strategy according to embodiments resulted in percept thresholds that were within the range of thresholds found under both single-channel configurations (FIG. 10A), while delivering lower charges per pulse under any given electrode. While not being bound by theory, the inventors hypothesize this is the result of the summation of interleaved pulses during the "RC recovery time interval", in which the membrane still contains some of the charge of the leading pulse (bringing it close to the fibers' activation threshold), making it easier for the fiber to depolarize after the trailing pulse. Interestingly, the CHIPS strategy seemed to perform better when leading-trailing pulses were interleaved from high-threshold to low-threshold channels (worst-to-best), or from configuration 2B to 1A (4BA) as seen in FIG. 4B. It is possible that the summation of the leading and trailing pulses is not perfect. While the leading pulse's effect on the membrane potential could be momentarily sustained, it could decay slightly during the transition to the trailing pulse. Since the trailing pulse plays a more critical role in crossing the fiber's activation threshold, the most efficient sequence would be the one where the trailing pulse is delivered from the best configuration. Finally, we observed that while the introduction of small delays between interleaved pulses does not seem to compromise the performance of the CHIPS strategy, large delays resulted in increased threshold amplitudes (FIG. 4D), especially for the worst performing multi-channel configuration (3AB). This is consistent with the idea of pulse summation, since large delays would be expected to attenuate the effect of the leading pulse on the nerve membrane at the time of arrival of the trailing pulse.

The comfort and selectivity of surface stimulation are often associated with electrode size and charge density. Large electrodes help dissipate the charge over the skin to prevent discomfort, reducing selectivity. On the other hand, reducing the size of the electrode can help focalize the stimulation within a given region of tissue, while introducing charge densities that could cause skin discomfort. Surface stimulation of the median and ulnar nerves has resulted in distracting local sensations due to the activation of the tactile afferents in the skin close to the electrodes. These sensations can be hard to ignore, affecting the overall performance of the stimulation approach. In contrast, the novel strategy provided by embodiments of the subject invention allowed focal stimulation to the median nerve using small surface electrodes while avoiding the large charge densities associated with local sensations and skin discomfort. Analysis of the MQL questionnaire responses revealed that stimulation under configuration 4BA evoked the most consistent reports of stronger, more comfortable distally-referred sensations (FIGS. 16A-16C) on the ring and middle fingers as well as the palm of the hand (FIGS. 17A-17D), without local sensations. These results suggest that implementation of the CHIPS strategy according to embodiments allowed for focal activation of a specific parts of the nerve (e.g., partial recruitment) resulting in sensations on the areas of the hand innervated by sensory fibers within the recruited section. More specifically, since the electrodes were placed so their current paths would interfere near the center of the wrist ventral surface, the median nerve would be expected to receive stimulation mostly near its ventral and medial aspect (the side closest to the ulna). Because of this, percepts are evoked more predominantly on the ring and middle fingers as well as the palm of the hand, matching the expected somatotopy of the median nerve at this location.

One of the limitations inherent in surface electrode stimulation (and especially single channel surface electrode stimulation) is that the initial electrode fitting parameters often must be determined through trial and error, and the electrode placement may have to be adjusted until each individual channel elicits the desired sensations. Because of this, it is possible that each individual channel's alignment with the median nerve is less than optimal. This would, for example, explain the significant differences in percept thresholds found between the two single-channel configurations (e.g., as shown in FIG. 4B). To overcome this issue, the stimulation fitting process may be enhanced in certain embodiments by implementing a spatially distributed set of electrodes (e.g., an electrode array) in which subsets of electrodes are selected to optimize the stimulation effectiveness and comfort. The combinations and location of active electrodes, as well as the characteristics of the stimulation pulses can be adjusted to reshape the spatiotemporal distribution of charge within the array. Embodiments provide for spatial steering of the stimulation focus to target specific tissue regions to modulate percept areas and intensity and help reduce or mitigate the effect of arm motion on the stimulation. Another limiting aspect of surface electrode stimulation is the long duration of the iterative processes used to determine percept thresholds. For example, on average, it took about an hour for subjects to complete all basic threshold determination blocks using the modified dual staircase. While these procedures are designed to determine percept thresholds accurately for research objectives, they are not sustainable for stimulation parameter fitting in the real world. Accurate and efficient stimulation fitting may be achieved through embodiments which provide interactive user-controlled fitting paradigms (user-in-the-loop) to help determine and optimize the stimulation parameter ranges, accelerate identification of the target nerve branches, and create user-specific stimulation profiles. These embodiments may further improve the efficiency and efficacy of this stimulation platform compared to traditional methods.

Other factors to consider in percept assessment results are the technical constraints of the stimulation system. For instance, MQL questionnaires were completed with pulse amplitudes set to 25% above the mean percept threshold at 500 μs. The wide range of amplitudes at this pulse width helped keep the stimulation from reaching the maximum current output of 3 mA while avoiding some of the uncomfortable sensations associated with long pulse widths. In contrast, shorter pulse widths would have required pulse amplitudes much higher than the output limit. An additional constraint within the pulse sequencing algorithm used during percept assessment procedures limited the stimulation frequency to 30 Hz. As a consequence, the specific percept characteristics reported should be viewed in the context of these specific stimulation parameters, although embodiments may provide stimulation approaches at various pulse widths and frequencies to deliver modulation of different stimulation parameters.

Examples discussed above evaluated the performance of embodiments in able-bodied subjects at the wrist level. Embodiments also provide stimulation in people with wrist disarticulation or transradial amputations, as well as to the general population of individuals with upper-limb amputation via an electrode array designed to fit, for example, around or above the elbow joint, where some nerve branches are more superficial. Conditions for implementing this stimulation approach are further improved in certain embodiments for patients undergoing pre-planned amputations, incorporating, for example, nerve reassignment procedures and relocating residual nerve branches to make them more accessible via surface electrodes.

Embodiments selectively elicit referred sensations that are comfortable, thus addressing some of the issues hampering traditional non-invasive neuromodulation approaches, making it a viable alternative for individuals who may not be eligible, or chose not to undergo, surgical procedures for invasive neuromodulation, as the latter carries risks of adverse effects such as infection and persistent implant site pain. Another innovative aspect of this invention is the potential to deliver targeted neuromodulation therapies for peripheral neuropathies. Surface stimulation has been previously explored as a non-pharmacological alternative for patients with neuropathic pain symptoms secondary to nerve injury or amputation. Although the neural mechanisms underlying the analgesic effects of conventional surface stimulation are complex and incompletely understood, they are generally consistent with the gate control theory. In this context, embodiments may deliver focal stimulation to non-pain-related sensory fibers to prevent, or "gate," nociceptive signals from being relayed from the spinal cord or brainstem to the brain.

Embodiments provide a novel multi-channel neurostimulation approach with advantages over traditional single-channel stimulation. Able-bodied subjects reported enhanced distally-referred percepts when receiving interleaved current pulses from multiple channels strategically distributed around the wrist. The performance of this approach was characterized for various interleaved pulse orders and delays to identify the most optimal configuration and to inform the development of advanced fitting procedures. The results presented here demonstrate that embodiments addresses some of the primary issues that have hindered the use of non-invasive neural stimulation to elicit meaningful sensations. This invention offers a potential alternative not only for delivering enhanced tactile feedback, but also for stimulation therapies to treat various pain conditions.

For individuals with upper-limb amputation, the functionality of commercially available prosthetic technology is limited, which impacts quality of life and often leads to prosthesis abandonment. The lack of sensory feedback from the prosthesis necessitates a high level of visual attention and limits the quality of control. It has been demonstrated that electrical stimulation of residual nerves with implantable electrodes can evoke distally referred sensations in the phantom hand. This has been used to provide amputees with intuitive sensory feedback, resulting in functional and psychological benefits. However, the invasive nature of the device implantation procedures is not acceptable to all.

Surface electrical neurostimulation is a potential non-invasive alternative for providing somatotopically-matched sensory feedback. In this approach, surface electrodes applied on the skin are used to deliver electrical pulses to nearby peripheral nerves, activating afferent pathways. Earlier studies have shown that transcutaneous stimulation can be used to elicit distally referred sensations when targeting the median and ulnar nerves at the forearm or at the elbow level. However, localized discomfort, poor selectivity, inadequate electrode and stimulation parameter fitting, and limited percept modulation have precluded wide adoption of traditional methods for surface stimulation as a viable sensory feedback approach.

An enhanced surface electrical neurostimulation (eSENS) platform according to embodiments of the subject invention is able to selectively elicit comfortable, distally referred percepts as described above. The eSENS platform utilizes a novel Channel-hopping Interleaved Pulse Scheduling (CHIPS) strategy to address some of the primary issues that have hindered the use of transcutaneous stimulation to deliver intuitive sensory feedback. Embodiments leverage the combined influence of short, sub-threshold current pulses from independent channels, interleaved across a set of distributed electrodes, to deliver functional (e.g., supra-threshold) stimulation levels within the tissue while reducing (e.g., sub-threshold) the total charge per pulse delivered by any given electrode. This novel approach has been shown to elicit enhanced tactile percepts while avoiding the local sensations and skin discomfort associated with the large charge densities in traditional methods. In addition to comfort and selectively, another important requirement for an intuitive artificial sensory feedback platform is the ability to convey discriminable levels of tactile intensities. The intensity of a tactile stimulus is one of its most basic sensory dimensions. It can be used to provide relevant sensory information such as grasping force when manipulating an object.

Thus, it is beneficial for certain embodiments to convey a wide range of discriminable percept intensities in order to provide intuitive sensory feedback during functional tasks.

Tactile sensations in neurologically intact individuals involve the integration of more than one kind of stimulus and more than one kind of tactile mechanoreceptor to form a coherent percept. The dynamics of the receptor output convey important information about the properties of the stimulus through rate coding and population coding. In rate coding, the frequency of the action potentials generated by the sensory receptors is proportional to the intensity of the stimulus. In population coding, changes in stimuli intensity is conveyed by the total number of active neurons in the receptor population. When the stimulus intensity increases, receptors with lower thresholds are first recruited, followed by receptors with higher thresholds. The contributions of firing rate and population recruitment to percept intensity are believed to be closely intertwined.

In electrical stimulation embodiments, firing rate and fiber population recruitment can be influenced by varying the stimulation Pulse Frequency (PF) and Pulse Charge (Q), respectively. When the stimulation pulses are square, the pulse charge can be expressed as the product of Pulse Amplitude (PA) and the Pulse Width (PW). Previous studies with electrical stimulation of residual nerves in amputees have modulated PF or Q independently to elicit changes in percept intensity. However, since rate and recruitment are both linked to percept intensity, modulation of only one of these two parameters could have resulted in a narrow range of discriminable levels of intensity that could be provided. In studying the effect of these two parameters on percept intensity gradation in amputees receiving direct electrical stimulation around their residual nerves it has been shown that PF and Q had systematic, cooperative effects on perceived tactile intensity, which supports the idea that the intensity of the perceived sensation is in part determined by the activation rate across the entire population of activated afferent neurons, weighted by fiber type. An activation charge-rate (AQR) model unifies these two parameters into a single quantity that predicts percept intensity when delivering direct peripheral nerve stimulation.

The inventors hypothesized the ability to convey a wide range of discriminable levels of intensity could be achieved with embodiments according to the subject invention by combining these two aspects of neural response, PF and Q. However, it was not known whether the AQR model would predict intensity perception for transcutaneous neurostimulation in the same way as reported for direct peripheral nerve stimulation. To answer this, classical psychophysical methods were applied to investigate the effect of these stimulation parameters on percept intensity gradation in able-bodied subjects receiving non-invasive stimulation from the eSENS platform, and in a subject with a transradial amputation receiving direct peripheral nerve stimulation with implanted intrafascicular electrodes. This characterization of the influence of charge and frequency on percept intensity requires careful exploration of the parameter space and accurate stimulation parameter fitting, which includes the determination of optimal stimulation amplitudes and selection of the operating ranges for each modulated parameter. Stimulation parameter fitting has been traditionally done over iterative procedures involving psychophysics measures or verbal reports from subjects. These procedures are time-consuming and can take a large portion of an experimental session. To address this bottleneck, the inventors implemented subject-controlled calibration routines according to an aspect of the subject invention that were developed to streamline the determination of stimulation amplitude thresholds and selection of the operating ranges for stimulation parameters such as pulse charge and pulse frequency, based on real-time input from the subjects.

A series of forced-choice tasks probed the subjects' ability to discriminate changes in percept intensity, while percept intensity rating tasks were used to assess how the range of percept intensities vary as stimulation parameters change. All experiments were completed across three parameter mapping schemes: modulation of pulse frequency alone, charge alone, and modulation of charge-rate (QR) in which both PF and Q are adjusted simultaneously. This newly acquired understanding may serve as the foundation for establishing a streamlined parameter fitting strategy to enable the eSENS platform to convey a wide range of graded percept intensities during functional tasks.

Example 7—Charge Rate Modulation for Non-Invasive and Intrafascicular Stimulation This study examines the dependency of percept intensity range and gradation on stimulation pulse frequency and pulse charge in able-bodied subjects with non-invasive median nerve stimulation, and in a subject with a transradial amputation receiving intrafascicular ulnar nerve stimulation. The discriminability and dynamic range of percept intensity were assessed for all subjects in a series of forced-choice tasks and open-ended intensity estimation tasks. All experiments were double-blinded with a randomized stimulus presentation order.

Written informed consent was obtained from 10 adult subjects (7 males, 3 females, mean age±SD: 29±3.5) in compliance with the Institutional Review Board of Florida International University. All prospective subjects were screened prior to the study to determine eligibility. Subjects were able-bodied, with no sensory disorders or any self-reported condition listed as a contraindication for transcutaneous electrical stimulation (pregnancy, epilepsy, lymphedema, or cardiac pacemaker) (Rennie, 2010).

Written informed consent was obtained from an individual with a unilateral left-arm transradial amputation (40-year-old male, 7-years post traumatic amputation) and was enrolled in an early feasibility clinical trial, Neural Enabled Prosthesis for Upper Limb Amputees (ClinicalTrials.gov: NCT03432325). Briefly, in March 2018 an investigational neural stimulator with a distributed intrafascicular multi-electrode (DIME) (Thota et al., 2015, Pena et al., 2017), comprising 15 longitudinal intrafascicular electrodes (LIFEs) (Dhillon and Horch, 2005) that are arranged in three bundles of five electrodes was implanted subcutaneously in the deltoid region of the left upper-arm of the subject. Ten LIFEs were implanted in the median nerve (two sets of five at each of two sites along the nerve) and five were implanted in the ulnar nerve.

Subjects were seated in front of a table with a computer screen, a custom 3-button keyboard and a control knob (FIG. 13 and FIG. 14). The screen displayed instructions for the subject at different stages of the study. The subjects used the keyboard to provide percept responses, and the knob to adjust various stimulation parameters at different stages of the study. The knob was set to control stimulation parameter values within safe levels. Subjects were instructed to concentrate throughout the experiment but were encouraged to stretch and move their hand during periodic breaks to prevent discomfort. Subjects were asked about their comfort levels, or if additional breaks were needed after each task.

For surface electrical neurostimulation in able-bodied subjects, each subject received transcutaneous electrical stimuli from four self-adhesive hydrogel electrodes (Rhythmlink International LLC, Columbia, S.C.) placed around the right wrist. This location allowed superficial access to the median nerve, which contains afferent fibers innervating the radial aspect of the palm, and the tips of the thumb, index and middle fingers.

Each subject's right forearm was thoroughly cleaned with a wet wipe and placed on a support pad on the table, with their right hand's palmar surface parallel to the vertical plane. Two small stimulating (s) electrodes (15×20 mm) were placed on the ventral aspect of the wrist (~3 cm from the distal radial crease) and two large return (r) electrodes (20×25 mm) placed on the opposite (dorsal) side. Each "s-r" electrode pair was assigned to an independent stimulation channel (A and B) and configured such that their current paths would cross each other and intersect the median nerve transversally (FIG. 12B). Placement of each "s-r" pair was determined by exploring different locations around the median nerve while providing brief, is long stimulation bursts (500 μs biphasic, anode-first pulses at 30 Hz) at different amplitude levels between 1.5 mA and 3 mA, in increments of 0.1 mA, until a distinct referred sensation was reported by the subject.

A multi-channel programmable, optically isolated benchtop bio-stimulator (TDT IZ2-16H, Tucker-Davis Technologies, Alachua Fla. USA) was used to deliver charge-balanced, current-controlled biphasic rectangular pulses. The stimulator was controlled by a custom TDT Synapse stimulation control environment interfaced to a custom MATLAB (v2019b, MathWorks Inc, Natick, Mass.) program designed to run and monitor the different study conditions and adjust the stimulation parameters based on subject responses.

The stimulation was delivered to the median nerve following the CHIPS strategy according to embodiments (FIG. 12B), in which two short biphasic anode-first pulses were interleaved from two independent stimulation channels (hopping from A to B) so that the anodic phases of each channel were delivered consecutively, followed by their respective balancing phases after a 100 μs inter-phase gap (IPG). The stimulation PW was defined as the sum of the individual interleaved phase durations (FIG. 12B). The interleaved pulses did not overlap in time to prevent channel interactions. Additional information regarding the transcutaneous stimulation procedure can be found in EXAMPLE 6.

Pulse Amplitude thresholds were obtained from all ablebodied subjects under 5 different Pulse Width values (300 μs to 700 μs, at 100 μs intervals). The order of the pulse widths was randomized across all subjects. During the PA threshold determination procedure, subjects interacted with a custom MATLAB algorithm designed to control the delivery of electrical stimuli and collect the subject's responses. Subjects triggered the delivery of a constant 5 Hz pulse train by pressing the "Go" button on a keyboard, and then used a custom control knob to adjust the PA (from 0 μA to 3000 μA) to find the lowest possible level that evoked a percept. This procedure was performed twice, and the PA was averaged for each PW. The subject responses were fitted to the Lapicque-Weiss's theoretical model (Lapicque L 1909 Definition experimentale de l'excitabilite Soc Biol 77 280-3; and Weiss G 1990 Sur la possibilite de rendre comparables entre eux les appareils servant a lexcitation electrique Archives italiennes de biologie 35 413-45; each of which, respectively, is hereby incorporated by reference herein in its entirety) to derive the strength-duration (SD) profile. The stimulation pulse amplitude used throughout this study was set to 50% above the percept threshold (1.5×PAth) at a PW of 500 μs. This duration was chosen since it lay beyond the nonlinear region of the SD profile, thus allowing for a wide range of PW to be used at this PA.

A similar subject-controlled calibration routine was used to determine the operating ranges for Q and PF that would be used throughout the study. For able-bodied subjects, modulation of Q was achieved by fixing PA and adjusting PW. First, stimulation was delivered at a fixed PF of 100 Hz while instructing the subjects to use the knob to explore a wide range of PW (from 100 μs to 800 μs) to find the lowest possible level that evoked a reliable percept, and the highest possible level that did not cause discomfort. Lastly, the stimulation PW was set to the midpoint of the recently obtained PW range, and the subjects were again instructed to use the knob to explore a wide range of PF (from 30 Hz to 300 Hz) to find the lowest possible frequency that was not perceived as pulsating (fusion), and the level at which the perceived stimulation intensity did not change (saturation).

Modulation of QR was achieved by adjusting both PF and Q simultaneously, along their operating ranges. The pulse charge at perception threshold (Qth) of each subject was derived from their SD profile and was used with the AQR model (AQR=(Q~Qth)×PF where Q=PA×PW) to calculate the equivalent QR range values that would result from each PF and Q adjustment.

The subject with the transradial amputation had a fully implantable, wireless multi-channel intrafascicular neurostimulator based on the design of the CI24RE (Cochlear Ltd., Sydney, Australia) with lead wires attached to 15 LIFE electrodes implanted longitudinally inside fascicles of the median and ulnar nerves (FIG. 13A). The stimulator received wireless transcutaneous communication of stimulation pulse parameters and power through an RF coil, from a custom stimulation control software and delivers charge-balanced biphasic stimulation pulses with pulse-by-pulse control of PA, PW, IPG and pulse timing, which provides control of PF. Additional information regarding the neurostimulator, electrodes, and implantation procedure used for this subject can be found in Thota, et al. (2015) (A system and method to interface with multiple groups of axons in several fascicles of peripheral nerves, J. Neurosci. Methods 244, 78-84, doi: 10.1016/j.jneumeth.2014.07.020) and Pena et al (2017) (J. Neural Eng. 14 066014), each of which, respectively, is hereby incorporated by reference herein in its entirety.

During this study, the implanted stimulator delivered biphasic, cathode-first rectangular pulses with a fixed PW of 300 μs and an IPG of 57 μs. The stimulation was delivered through an intrafascicular electrode located in the ulnar nerve. Stimulation on this electrode evoked a tingling sensation that was felt on the anterior side of pinky, from the distal interphalangeal crease to the distal palmar crease.

Pulse Amplitude (PA) thresholds were obtained from the subject under 10 different PW values (75 μs to 300 μs, at 25 μs intervals). During the PA threshold determination procedure, the subject used a custom control knob to adjust the PA (from 20.22 μA to 76.94 μA) to find the lowest possible level that evoked a percept. This procedure was performed three times, and the PA was averaged for each PW. The strength-duration (SD) profile was also derived for this subject by fitting the detection responses to the Lapicque-Weiss's model. The stimulation PW used throughout this study was set to 300 μs to allow for a wide range of PA values to be explored. A similar subject-controlled calibration routine was used to determine the operating ranges for Q and PF that would be used throughout the study. In this case, modulation of Q was achieved by fixing PW to 300 μs and adjusting PA. First, stimulation was delivered at a fixed PF of ~76 Hz while instructing the subject to use the knob to explore a wide range of PA (from 20.22 μA to 76.94 μA) to find the lowest possible level that evoked a reliable percept, and the highest possible level that did not cause discomfort. Lastly, the stimulation PA was set to the midpoint of the recently obtained PA range (~37.36 μA), and the subject was again instructed to use the knob to explore a wide range of PF (from 5 Hz to 333 Hz) to find the lowest possible frequency that was not perceived as pulsating (fusion), and the level at which the perceived stimulation intensity did not change (saturation).

Modulation of QR was achieved by adjusting both PF and Q simultaneously, along their operating ranges. The pulse charge at perception threshold (Qth) was derived from the subject's SD profile and was used with the AQR model to calculate the equivalent QR range values that would result from each PF and Q adjustment.

A series of forced-choice tasks were completed to assess the subject's ability to discriminate different stimulation intensity levels. On each trial, a pair of stimulation bursts were presented, and the subjects were instructed to report whether the second burst felt softer, same or stronger than the first burst by responding on a custom 3-button keyboard. Each burst lasted for 1 second, with a 0.5 second pause in between. Subjects were instructed to focus on the intensity or magnitude of the evoked sensation when deciding how to respond. A single experimental block consisted of 45 randomized burst pair presentations (9 unique stimulus pairs presented 5 times) with short breaks after every 10 presentations. All subjects completed 3 experimental blocks: modulating PF, Q, or both (QR). In each block, each burst pair differed in the parameter being tested. The first burst was always the reference, in which the tested parameter was set to the midpoint of its range. The reference burst was compared to 9 unique test bursts that included 4 equally spaced values below and above the reference, with a step size no larger than 25% from the reference value. The just noticeable difference (JND) was determined for each parameter tested by fitting the subject's responses to a cumulative normal distribution to obtain the psychometric function. The JND was calculated by averaging the 75% correct performance points for both ends of the psychometric function. To compare discriminability across conditions, the Weber ratios were computed by dividing the JND by the reference value for each parameter tested.

The discrimination performance under each stimulation conditions was assessed by comparing their effect on the weber ratios with a one-way ANOVA using GraphPad Prism 8 (v8.3.1 for Windows, GraphPad Software, San Diego, Calif. USA). Post-hoc multiple comparisons between stimulation conditions were made using the Tukey-Kramer test at an alpha level of 0.05 for significance. One sample t-tests were performed to compare discrimination performances between transcutaneous and intrafascicular stimulation.

Intensity estimation was recorded using a free magnitude scaling paradigm or open-ended scale to test the span of evoked percept intensities and allow relative comparison of the perceived strength levels. This method has been traditionally used in psychophysics to perform direct quantitative assessments of subjective magnitudes or intensities. For each intensity estimation trial, a 1-second-long stimulation burst was delivered, and the subject was asked to state a number that represented the perceived intensity or magnitude of the evoked sensation by comparing it with the previous burst. For instance, if one stimulus feels half or twice as intense as the previous one, it could be given a score that is half or twice as large. A score of 0 was used when no sensation is perceived. All subjects completed 3 experimental blocks, each consisting of up to 30 randomized trials (up to 10 equally spaced levels per test condition). Three test conditions were intermixed in each experimental block: During Q modulation, Q was changed while PF was fixed at its range midpoint. During PF modulation, PF was changed while Q was fixed at its range midpoint. Finally, during QR modulation, both Q and PF were changed simultaneously. Ratings were normalized by dividing the values by the grand mean rating on their respective blocks.

Simple linear regressions were performed to assess the relationship between percept intensity ratings and each stimulation condition used. The perceived intensity ranges under the different stimulation condition were compared with a one-way ANOVA (GraphPad Prism 8). Post-hoc multiple comparisons of the intensity ranges between stimulation condition were made using the Tukey-Kramer test at an alpha level of 0.05 for significance.

Ten able-bodied subjects received transcutaneous stimulation from the eSENS platform enhanced by the novel CHIPS strategy. This approach evoked comfortable distally referred sensations of tingle, pressure and light touch in the general area innervated by the sensory fibers in the median nerve (palmar surface, index, middle, and part of the ring finger). A subject with a transradial amputation received intrafascicular stimulation through an electrode located in the ulnar nerve. Stimulation on this electrode evoked comfortable distally referred tingling sensations that were felt on the anterior side of little finger, from the distal interphalangeal crease to the distal palmar crease. The discriminability and dynamic range of percept intensity were assessed for all subjects across three parameter mapping schemes. No uncomfortable or local sensations, and no side effects like irritation or redness of the skin were observed in any of the able-bodied subjects.

All subjects were able use a control knob to determine percept threshold values and define an operating range for both PF and Q from a wide range of parameter values. In average, these calibration routines were completed in less than 10 minutes. Able-bodied subjects reported an operating range for Q spanning from 0.77±0.19 μC to 1.42±0.32 μC with surface stimulation, while the operating range for PF spanned from 56.07±15.76 Hz (fusion) to 185.38±38.06 Hz (saturation). Simultaneous adjustment of PF and Q over these ranges resulted in a wide QR range spanning from 1.48±2.26 μA to 107.97±42.30 μA. The reference value used for discrimination tasks was 52.13±21.89 μA, averaged across all subjects. All values are reported as mean±SD.

The subject with the transradial amputation reported an operating range for Q between 9.88 nC and 11.83 nC with intrafascicular stimulation, and a PF range between 36.0 Hz and 91.0 Hz. Simultaneous adjustment of PF and Q over these ranges resulted in a wide QR range spanning from 91.0 nA to 490.8 nA. The reference values used for discrimination tasks were 348 nA, 305 nA, and 281 nA for PF, Q and QR modulation respectively.

All subjects performed intensity discrimination tasks to determine how much change in a given stimulation parameter was required for the subjects to report a change in the perceived intensity of the evoked percept. In general, all were able to perceive changes in percept intensity across stimulation conditions, as evidenced by the psychometric curves that were obtained (FIGS. 14A-14B). For consistency, and to compare across stimulation conditions, all references and JND values are reported in terms of QR, defined as the total charge per second (μA). All results from able-bodied subjects are reported as mean±SD.

For able-bodied subjects (FIG. 14A), the JND during PF modulation was 9.71±4.04 μA, and the Weber ratio was 0.21±0.1. The JND for Q modulation was 6.70±4.31 μA, with a Weber ratio of 0.13±0.07. Simultaneous modulation of both PF and Q resulted in intensity discrimination performance that was between that found when either was adjusted in isolation. The JND during QR modulation was 9.74±6.55 μA, with a Weber ratio of 0.19±0.11. While the Weber ratio for Q modulation was visibly lower than PF and QR, they were all statistically indistinguishable (one-way ANOVA, $F(2,27)=1.935$, $p=0.1639$).

The subject with the amputation was able to discriminate intensity changes in percepts evoked by intraneural stimulation, with a performance comparable to that of able-bodied subjects (FIG. 14B). The JND for PF modulation was 36.33 nA, and the Weber ratio was 0.27. The JND for Q modulation was 36.34 nA, with a Weber ratio of 0.12. The JND during QR modulation was 47.03 nA, with a Weber ratio of 0.17.

It was observed that subjects perceived a wider range of intensities with QR modulation. While discrimination performance provides the minimum required change in stimulation parameter to produce a noticeable change in percept intensity, it does not elucidate the actual range of intensities that are possible with a given stimulation parameter range. To address this, the dynamic ranges of percept intensity for each stimulation condition were assessed for all able-bodied subjects and the subject with the transradial amputation over a series of intensity estimation trials. Intensity ratings given by the subjects were normalized for comparison. As expected, the perceived intensity increased when Q or PF were increased over their operational range. Modulation of QR was strongly correlated to percept intensity during non-invasive stimulation in able-bodied subjects: $r=0.87$; $p<0.0001$, and during intraneural stimulation in the subject with the amputation: $r=0.85$; $p<0.0001$. In both cases, the range of intensities that were perceived during QR modulation spanned wider than for the other parameters (FIGS. 15A and 15C).

Linear regressions were performed to predict perceived intensity as a function of charge-rate for all subjects. A one-way analysis of variance (ANOVA) on the perceived intensity ranges found for able-bodied subjects revealed significant differences between the stimulation conditions, $F(2,27)=101.8$, $p<0.0001$ (FIG. 15B; inset). A post hoc Tukey test showed that the perceived intensity ranges found for PF modulation spanned significantly narrower than for Q and QR modulation (both $p<0.0001$), but no significant differences in intensity ranges were found between Q and QR modulation ($p=0.13$). The regression slopes however were significantly different depending on which parameter was modulated ($F(2,23)=6.584$, $p=0.0055$). The slopes were steepest for Q, shallowest for PF, and intermediate for QR (FIG. 15B).

Responses from the subject with the amputation showed a similar trend where the intensity range found during QR was about 3.5 times the range of PF modulation, and about 1.3 times the range of Q modulation (FIG. 15C; inset). The regression slopes were significantly different from each other, $F(2,20)=4.202$, $p=0.03$. In this case, Q and QR modulation also showed the steepest and intermediate regression slopes, respectively. Also, the slope for PF modulation was the shallowest, to the point where it was not significantly different from zero ($F(1,6)=2.365$, $p=0.1750$).

An enhanced surface electrical neurostimulation (eSENS) platform according to an embodiment of the subject invention may selectively elicit comfortable, distally-referred percepts that could be used as sensory feedback. While comfort and selectively are important, the platform's ability to convey a wide range of discriminable levels of tactile intensities may be beneficial in some embodiments in order to provide a viable non-invasive option for intuitive sensory feedback during functional tasks. Embodiments of the subject invention the first evaluation of activation charge-rate (AQR) to enhance the percept intensity mapping with surface electrical neurostimulation. The charge-rate relationship was leveraged to develop subject-controlled calibration routines that streamlined the stimulation parameter fitting process.

A series of psychophysical tests were used to probe the effect of different parameter modulation strategies on the range and gradation of percept intensities elicited in able-bodied subjects with the eSENS platform, and in a subject with transradial amputation receiving intrafascicular neurostimulation. In both cases, simultaneous modulation of charge and frequency resulted in fine intensity discrimination and a wider dynamic range of intensities. This is consistent with the concept that percept intensity is driven by the total firing rate evoked in the recruited mechanoreceptive afferent population. While the intensity ranges obtained during modulation of charge and charge-rate were similar, charge-rate modulation provided a greater modulation resolution as the parameter map used implies changes in both frequency and charge values. Subjects also reported smoother transitions as charge-rate increased as compared to the more drastic step-wise changes from charge modulation alone. In contrast, frequency modulation alone resulted in lower discrimination performance and a significantly narrower intensity range. In this case, stimulation charge was fixed to the mid-point of its operating range while frequency was changed. Because of this, the stimulation was always supra-threshold, which explains why the lowest intensity value reported during frequency modulation never reached zero.

Implementation of this sensory encoding strategy within the eSENS platform showed that it is possible to artificially influence the intensity code transcutaneously with psychophysical responses comparable to more invasive methods. These results serve as the foundation for creating a parameter-percept mapping strategy that can be used for delivering graded sensory feedback during functional tasks.

Embodiments provide a streamlined parameter fitting strategy for wide range, graded sensation intensity mapping. Previous studies have performed percept characterization procedures in which stimulation parameters are varied to elicit a range of percept intensities and psychophysics measures or verbal reports are gathered from the subjects. Determination of activation thresholds, as well as lower and upper limits for different parameters is often done over lengthy iterative processes. While these procedures yield a detailed map between percept and stimulation parameter, they are time-consuming and can take a large portion of an experimental session. Therefore, more efficient stimulation parameter fitting procedures are provided by embodiments of the subject invention.

In this study, the activation charge-rate model was found to be a strong predictor for graded intensity perception during both transcutaneous and intrafascicular neurostimulation. This relationship was leveraged to enable fast and accurate stimulation parameter fitting with minimal intervention from the experimenter. Modulation of charge-rate was accomplished by adjusting pulse charge and pulse frequency simultaneously, along their operating ranges. These ranges were obtained through a subject-controlled calibration routine that was developed to simplify the exploration of the parameter-space. All subjects were able use a control knob to determine activation thresholds and define the operating range of pulse charges and pulse frequencies used throughout the study. The threshold determination procedures used in related studies implemented a modified dual staircase designed to determine percept thresholds accurately for research objectives. In this case, it took an average of 5 minutes for each subject to find the threshold amplitudes for a single strength-duration profile. In contrast, the subject-controlled calibration routine used in this study allowed subjects to determine up to four strength-duration profiles (one for each configuration) and define two operating ranges in less than 10 minutes. This calibration routine can be used to streamline the parameter fitting process for additional studies using the eSENS platform, and possibly other neurostimulation approaches. Implementation of the charge-rate encoding scheme could thus enhance the intensity mapping of functional information such as grasping force.

The intensity discrimination performance during frequency modulation, and by consequence during charge-rate modulation, could have been masked by potentially narrow operating ranges in pulse frequency due to the fusion-saturation limits. Other studies have shown that frequency discrimination performance is often better with low frequency references since subjects often use the timing of individual pulses as supplementary cues. However, as the intent of the study was to pay attention to the perceived intensity and not the frequency, subjects were instructed to pick the lower end of the operational frequency range as the point where individual pulses are no longer detectable (fusion). This helped avoid the presence of low frequency references and test bursts during the discrimination trials, which could have also increased the difficulty of the task.

This study focused on percept intensity. However, percept modality is also an important dimension of artificial feedback. While intensity is encoded by rate and population recruitment, modality seems to be encoded by the spatiotemporal patterning of this activity). Traditional surface stimulation methods have been shown to elicit sensations often reported as artificial or unnatural electrical tingling, or paresthesia. These sensations are believed to be the result of synchronous activation within a population of different fibers, which contrast with the more complex spatiotemporal patterns recognized during natural sensory perception. Previous studies with direct nerve stimulation and surface stimulation have implemented time-variant patterning strategies in which a sinusoidal or pseudorandom jitter is added to the charge and/or frequency. These strategies have shown some reports of more natural pressure and tapping percepts. In this study, subjects were asked to explore the full range of intensities available through charge-rate modulation before the end of the experimental session. When asked to describe the percept modality, most subjects reported feeling comfortable distally referred sensations of tingle, pressure, vibration and light touch. This could be due to the fact that subjects swept the range of intensities, causing changes in both temporal and spatial recruitment during charge-rate modulation. While this is not exactly the type of time-variant patterning used in other studies, the continuous changes in charge and rate may have resulted in more "natural" activation patterns than in traditional methods. Embodiments may include neuromorphic models that mimic healthy receptor behavior to generate time-variant patterns for both charge and frequency, to evoke more natural sensations.

Embodiments of the subject invention have implications for neuromodulation strategy development. Electrical stimulation of peripheral afferents has been used for decades to formulate an understanding of neural coding and to restore lost sensory function. Recently, deployment of implantable peripheral nerve interfaces has prompted multiple breakthroughs in artificial somatosensory feedback and the neural basis of touch. Although promising, these approaches have only been tested on a small number of subjects, and wide clinical applications are limited due to the required surgery procedure and long-term care, thus hindering development of advanced neuromodulation strategies for intuitive sensory feedback.

The percept intensity rating and discrimination performance of able-bodied subjects with the eSENS platform was comparable to the subject with transradial amputation receiving intrafascicular neurostimulation. Moreover, these results were consistent with studies of amputees with implanted cuff electrodes. One of the key differences between transcutaneous and intrafascicular stimulation was selectivity. This can be seen in the differences in charge threshold and comfort limits between able-bodied subjects and the subject with transradial amputation, which were consistent with the nature of the stimulation method used in each case. Transcutaneous activation of afferent fibers within a superficial nerve such as the median nerve in the wrist required ~1000 nC, which activated a larger portion of the nerve, evoking percepts on larger areas of the hand. In contrast, intrafascicular stimulation required lower charge (~10 nC) to activate smaller groups of axons within the fascicle. Although this difference may play a role in the location and span of the referred percept, it does not seem to affect the way intensity is encoded. This suggests that embodiments including the eSENS platform may be capable of influencing and modulating the sensory code and delivering information in a way that is comparable to implantable systems. Embodiments including the eSENS platform could thus serve as a testbed for studying the neural mechanisms of natural touch and developing advanced neuromodulation strategies for intuitive sensory feedback in able-bodied subjects before deployment in implantable systems.

It should be understood that the examples and embodiments described herein are for illustrative purposes only and that various modifications or changes in light thereof will be suggested to persons skilled in the art and are to be included within the spirit and purview of this application.

All patents, patent applications, provisional applications, and publications referred to or cited herein are incorporated by reference in their entirety, including all figures and tables, to the extent they are not inconsistent with the explicit teachings of this specification.

What is claimed is:

1. A system for delivering targeted focal neurostimulation with reduced charge density and increased selectivity to a target nerve, the system comprising:
    a first channel comprising a first alternating current (AC) source connected to a first stimulating electrode and a first receiving electrode, the first stimulating electrode radially spaced from the target nerve, and the first receiving electrode being in opposition to the first stimulating electrode such that a first signal path defined therebetween stimulates the target nerve;
    a second channel comprising a second AC source connected to a second stimulating electrode and a second receiving electrode, the second stimulating electrode radially spaced from the target nerve, and the second receiving electrode being in opposition to the second stimulating electrode such that a second signal path defined therebetween crosses the first signal path and stimulates the target nerve;
    a processor in operable communication with the first channel and the second channel; and
    a machine-readable medium in operable communication with the processor and having instructions stored thereon that, when executed by the processor, perform the following steps:
        delivering through the first channel a first stimulation pulse (SP1) having a first stimulation pulse width (SP1W);
        delivering through the second channel a second stimulation pulse (SP2) after delivery of the SP1, the SP2 having a second stimulation pulse width (SP2W), the SP1 and the SP2 each contributing to an effective net stimulation pulse (ESP) having an effective net stimulation pulse width (ESPW) sufficient to effectively stimulate the target nerve, the ESPW being greater than the SP1W and the ESPW being greater than the SP2W, thereby delivering the targeted focal neurostimulation with reduced charge density and increased selectivity to the target nerve;
        delivering through one of the first channel or the second channel a first charge-balancing pulse (BP1) after delivery of the SP2, the BP1 having a first balancing pulse width (BP1W); and
        delivering through the other of the first channel or the second channel a second charge-balancing pulse (BP2) after delivery of the BP1, the BP2 having a second balancing pulse width (BP2W), the BP1 and the BP2 each contributing to an effective net charge-balancing pulse (EBP) having an effective net charge-balancing pulse width (EBPW) sufficient to effectively reduce a residual local charge created by the ESP in or around the target nerve, the EBPW being greater than the BP1 W and the EBPW being greater than the BP2W.

2. The system according to claim 1, each of the SP1, the SP2, the BP1, and the BP2, respectively, having a start time and an end time, the start time of the BP1 being followed by an inter-phase gap (IPG) having a value between 0 microseconds and 500 microseconds after the end time of the SP2.

3. The system according to claim 2, the start time of the SP2 being followed by a first interleaved stimulation pulse delay (DS1) having a value between 0 microseconds and 500 microseconds after the end time of either (a) the SP1, or (b) an optional additional interleaved stimulation pulse (SP3), the SP3, if present, being delivered after delivery of the SP1, and before the delivery of the SP2.

4. The system according to claim 2, the start time of the BP2 being followed by a first interleaved charge-balancing pulse delay (DB1) having a value between 0 microseconds and 500 microseconds after the end time of either (a) the BP1, or (b) an optional additional interleaved charge-balancing pulse (BP3), the BP3, if present, being delivered after delivery of the BP1, and before the delivery of the BP2.

5. The system according to claim 1, the instructions when executed further performing the following additional steps:
    delivering through one of the first channel or the second channel a fourth stimulation pulse (SP4) after delivery of the BP2, the SP4 having a fourth stimulation pulse width (SP4W); and
    delivering through the other of the first channel or the second channel a fifth stimulation pulse (SP5) after delivery of the SP4, the SP5 having a fifth stimulation pulse width (SP5W), the SP4 and the SP5 each contributing to a second effective net stimulation pulse (ESP2) having a second effective net stimulation pulse width (ESP2W) sufficient to effectively stimulate the target nerve, the ESP2W being greater than the SP4W and the ESP2W being greater than the SP5W.

6. The system according to claim 5, each of the SP4 and the SP5, respectively, having a start time and an end time, the start time of the SP5 being followed by a second interleaved stimulation pulse delay (DS2) having a value between 0 microseconds and 500 microseconds after the end time of either (a) the SP4, or (b) an optional additional interleaved stimulation pulse (SP6), the SP6, if present, being delivered after delivery of the SP4, and before the delivery of the SP5.

7. The system according to claim 1, the first stimulating electrode and the first receiving electrode being positioned to stimulate the target nerve transversely.

8. The system according to claim 1, the second stimulating electrode and the second receiving electrode being positioned to stimulate the target nerve transversely and being generally aligned longitudinally with each other and with the first stimulating electrode and the first receiving electrode.

9. The system according to claim 1, the SP1 and the BP1 forming an anode-first biphasic pulse on the first channel, the SP2 and the BP2 forming an anode-first biphasic pulse on the second channel, and the SP1, the SP2, the BP1, and the BP2 each contributing to delivering an effective anode-first biphasic pulse to the target nerve.

10. A method for delivering targeted focal neurostimulation with reduced charge density and increased selectivity to a target nerve, the method comprising:
    providing a first channel comprising a first alternating current (AC) source connected to a first stimulating electrode and a first receiving electrode, the first stimulating electrode radially spaced from the target nerve, and the first receiving electrode being in opposition to the first stimulating electrode such that a first signal path defined therebetween stimulates the target nerve;

providing a second channel comprising a second AC source connected to a second stimulating electrode and a second receiving electrode, the second stimulating electrode radially spaced from the target nerve, and the second receiving electrode being in opposition to the second stimulating electrode such that a second signal path defined therebetween crosses the first signal path and stimulates the target nerve;

delivering through the first channel a first stimulation pulse (SP1) having a leading stimulation pulse width (SP1W);

delivering through the second channel a second stimulation pulse (SP2) after delivery of the SP1, the SP2 having a trailing stimulation pulse width (SP2W), the SP1 and the SP2 each contributing to an effective net stimulation pulse (ESP) having an effective net stimulation pulse width (ESPW) sufficient to effectively stimulate the target nerve, the ESPW being greater than the SP1W and the ESPW being greater than the SP2W, thereby delivering the targeted focal neurostimulation with reduced charge density and increased selectivity to the target nerve;

delivering through one of the first channel or the second channel a first charge-balancing pulse (BP1) after delivery of the SP2, the BP1 having a first balancing pulse width (BP1W); and delivering through the other of the first channel or the second channel a second charge-balancing pulse (BP2) after delivery of the BP1, the BP2 having a second balancing pulse width (BP2W), the BP1 and the BP2 each contributing to an effective net charge-balancing pulse (EBP) having an effective net charge-balancing pulse width (EBPW) sufficient to effectively reduce a residual local charge created by the ESP in or around the target nerve, the EBPW being greater than the BP1W and the EBPW being greater than the BP2W.

11. The method according to claim 10, each of the SP1, the SP2, the BP1, and the BP2, respectively, having a start time and an end time, the start time of the BP1 being followed by an inter-phase gap (IPG) having a value between 0 microseconds and 500 microseconds behind the end time of the SP2.

12. The method according to claim 11, the start time of the SP2 being followed by a first interleaved stimulation pulse delay (DS1) having a value between 0 microseconds and 500 microseconds after the end time of either (a) the SP1, or (b) an optional additional interleaved stimulation pulse (SP3), the SP3, if present, being delivered after delivery of the SP1, and before the delivery of the SP2.

13. The method according to claim 11, the start time of the BP2 being followed by a first interleaved charge-balancing pulse delay (DB1) having a value between 0 microseconds and 500 microseconds after the end time of either (a) the BP1, or (b) an optional additional interleaved charge-balancing pulse (BP3), the BP3, if present, being delivered after delivery of the BP1, and before the delivery of the BP2.

14. The method according to claim 10, further comprising:

delivering through one of the first channel or the second channel a fourth stimulation pulse (SP4) after delivery of the BP2, the SP4 having a fourth stimulation pulse width (SP4W); and delivering through the other of the first channel or the second channel a fifth stimulation pulse (SP5) after delivery of the SP4, the SP5 having a fifth stimulation pulse width (SP5W), the SP4 and the SP5 each contributing to a second effective net stimulation pulse (ESP2) having a second effective net stimulation pulse width (ESP2W) sufficient to effectively stimulate the target nerve, the ESP2W being greater than the SP4W and the ESP2W being greater than the SP5W.

15. The method according to claim 14, each of the SP4, and the SP5, respectively, having a start time and an end time, the start time of the SP5 being followed by a second interleaved stimulation pulse delay (DS2) having a value between 0 microseconds and 500 microseconds after the end time of either (a) the SP4, or (b) an optional additional interleaved stimulation pulse (SP6), the SP6, if present, being delivered after delivery of the SP4, and before the delivery of the SP5.

16. A system for delivering targeted focal neurostimulation with reduced charge density and increased selectivity to a target nerve, the system comprising:

a first channel comprising a first alternating current (AC) source connected to a first stimulating electrode and a first receiving electrode, the first stimulating electrode radially spaced from the target nerve, and the first receiving electrode being in opposition to the first stimulating electrode such that a first signal path defined therebetween stimulates the target nerve, and;

a second channel comprising a second AC source connected to a second stimulating electrode and a second receiving electrode, the second stimulating electrode radially spaced from the target nerve, and the second receiving electrode being in opposition to the second stimulating electrode such that a second signal path defined therebetween crosses the first signal path and stimulates the target nerve;

a processor in operable communication with the first channel and the second channel; and a machine-readable medium in operable communication with the processor and having instructions stored thereon that, when executed by the processor, perform the following steps:

delivering through the first channel a first stimulation pulse (SP1) having a first stimulation pulse width (SP1 W);

delivering through the second channel a second stimulation pulse (SP2) after delivery of the SP1, the SP2 having a second stimulation pulse width (SP2W), the SP1 and the SP2 each contributing to an effective net stimulation pulse (ESP) having an effective net stimulation pulse width (ESPW) sufficient to effectively stimulate the target nerve, the ESPW being greater than the SP1W and the ESPW being greater than the SP2W;

delivering through one of the first channel or the second channel a first charge-balancing pulse (BP1) after delivery of the SP2, the BP1 having a first balancing pulse width (BP1W);

delivering through the other of the first channel or the second channel a second charge-balancing pulse (BP2) after delivery of the BP1, the BP2 having a second balancing pulse width (BP2W), the BP1 and the BP2 each contributing to an effective net charge-balancing pulse (EBP) having an effective net charge-balancing pulse width (EBPW) sufficient to effectively reduce a residual local charge created by the ESP in or around the target nerve, the EBPW being greater than the BP1W and the EBPW being greater than the BP2W;

delivering through one of the first channel or the second channel a fourth stimulation pulse (SP4) after delivery of the BP2, the SP4 having a fourth stimulation pulse width (SP4W); and delivering through the other of the first channel or the second channel a fifth stimulation pulse (SP5) after delivery of the SP4, the SP5 having a fifth stimulation pulse width (SP5W), the SP4 and the SP5 each contributing to a second effective net stimulation pulse (ESP2) having a second effective net stimulation pulse width (ESP2W) sufficient to effectively stimulate the target nerve, the ESP2W being greater than the SP4W and the ESP2W being greater than the SP5W, thereby delivering the targeted focal neurostimulation with reduced charge density and increased selectivity to the target nerve.

17. The system according to claim 16, each of the SP1, the SP2, the SP4, the SP5 the BP1, and the BP2, respectively, having a start time and an end time, the start time of the BP1 being followed by an inter-phase gap (IPG) having a value between 0 microseconds and 500 microseconds behind the end time of the SP2, the start time of the SP2 being followed by a first interleaved stimulation pulse delay (DS1) having a value between 0 microseconds and 500 microseconds after the end time of either (a) the SP1, or (b) an optional additional interleaved stimulation pulse (SP3), the SP3, if present, being delivered after delivery of the SP1, and before the delivery of the SP2, the start time of the BP2 being followed by a first interleaved charge-balancing pulse delay (DB1) having a value between 0 microseconds and 500 microseconds after the end time of either (a) the BP1, or (b) an optional additional interleaved charge-balancing pulse (BP3), the BP3, if present, being delivered after delivery of the BP1, and before the delivery of the BP2, and the start time of the SP5 being followed by a second interleaved stimulation pulse delay (DS2) having a value between 0 microseconds and 500 microseconds after the end time of either (a) the SP4, or (b) an optional additional interleaved stimulation pulse (SP6), the SP6, if present, being delivered after delivery of the SP4, and before the delivery of the SP5.

18. The system according to claim 17, the first stimulating electrode and the first receiving electrode being positioned to stimulate the target nerve transversely, the second stimulating electrode and the second receiving electrode being positioned to stimulate the target nerve transversely and being generally aligned longitudinally with each other and with the first stimulating electrode and the first receiving electrode, the SP1 and the BP1 forming an anode-first biphasic pulse on the first channel, the SP2 and the BP2 forming an anode-first biphasic pulse on the second channel, and the SP1, the SP2, the BP1, and the BP2 each contributing to delivering an effective anode-first biphasic pulse to the target nerve.

* * * * *